US007875618B2

(12) United States Patent
Malamas et al.

(10) Patent No.: US 7,875,618 B2
(45) Date of Patent: Jan. 25, 2011

(54) SUBSTITUTED IMIDAZO[1,5-A]QUINOXALINES USEFUL AS INHIBITORS OF PHOSPHODIESTERASE 10 FOR THE TREATMENT OF NEUROLOGICAL AND OTHER DISORDERS

(75) Inventors: Michael S. Malamas, Jamison, PA (US); Yike Ni, Monmouth JCT, NJ (US); James Joseph Erdei, Flourtown, PA (US); Norbert Höfgen, Ottendorf-Okrilla (DE); Hans Stange, Riesa (DE); Rudolf Schindler, Dresden (DE); Ute Egerland, Radebeul (DE); Barbara Langen, Radebeul (DE)

(73) Assignees: Wyeth, Madison, NJ (US); elbion GmbH, Radebeul (DE)

( * ) Notice: Subject to any disclaimer, the term of this patent is extended or adjusted under 35 U.S.C. 154(b) by 0 days.

(21) Appl. No.: 12/277,844

(22) Filed: Nov. 25, 2008

(65) Prior Publication Data
US 2009/0143367 A1 Jun. 4, 2009

Related U.S. Application Data

(60) Provisional application No. 61/004,844, filed on Nov. 30, 2007.

(51) Int. Cl.
*A61K 31/4965* (2006.01)
(52) U.S. Cl. .................... 514/255.05; 544/11; 544/353; 546/167; 546/268.1; 548/202; 548/247; 548/373.1; 549/59
(58) Field of Classification Search ............ 514/255.05; 544/111, 353; 546/167, 268.1; 548/202, 548/247, 373.1; 549/59
See application file for complete search history.

(56) References Cited

U.S. PATENT DOCUMENTS

| 5,034,530 | A | * | 7/1991 | Hansen et al. ............... 544/346 |
|---|---|---|---|---|
| 5,055,465 | A | | 10/1991 | Davey |
| 6,235,740 | B1 | | 5/2001 | Barrish et al. |
| 6,239,133 | B1 | | 5/2001 | Barrish et al. |
| 6,326,375 | B1 | | 12/2001 | Fukami et al. |
| 6,335,345 | B1 | | 1/2002 | Fukami et al. |
| 6,566,367 | B2 | | 5/2003 | Bakthavatchalam et al. |
| 7,550,465 | B2 | | 6/2009 | Höefgen et al. |
| 2002/0151456 | A1 | | 10/2002 | Song et al. |
| 2003/0036652 | A1 | | 2/2003 | Bakthavatchalam et al. |
| 2003/0032579 | A1 | | 3/2003 | Lebel et al. |
| 2007/0032404 | A1 | | 2/2007 | Sweet |
| 2007/0299079 | A1 | | 12/2007 | Norbert et al. |
| 2008/0027064 | A1 | | 1/2008 | Hoefgen et al. |
| 2009/0143361 | A1 | | 6/2009 | Malamas et al. |
| 2009/0143391 | A1 | | 6/2009 | Hoefgen et al. |
| 2009/0143392 | A1 | | 6/2009 | Hoefgen et al. |
| 2009/0239874 | A1 | | 9/2009 | Hoefgen et al. |
| 2010/0120762 | A1 | | 5/2010 | Stange et al. |
| 2010/0120763 | A1 | | 5/2010 | Stange et al. |

FOREIGN PATENT DOCUMENTS

| EP | 0 347 094 | 12/1989 |
|---|---|---|
| EP | 0 736 532 | 9/1996 |
| EP | 0 400 583 | 5/1999 |
| WO | WO 92/22552 | 12/1992 |
| WO | WO 99/09845 | 3/1999 |
| WO | WO 99/45009 | 9/1999 |
| WO | WO 00/43392 | 7/2000 |
| WO | WO 00/56719 | 9/2000 |
| WO | WO 01/68097 | 9/2001 |
| WO | WO 03/010175 | 2/2003 |
| WO | WO 03/082190 | 10/2003 |
| WO | WO 2005/014595 | 2/2005 |
| WO | WO 2005/087919 | 9/2005 |
| WO | WO 2005/120514 | 12/2005 |
| WO | WO 2006/089815 | 8/2006 |
| WO | WO 2007/137819 | 12/2007 |
| WO | WO 2007/137820 | 12/2007 |
| WO | WO 2009/068246 | 6/2009 |
| WO | WO 2009/070583 | 6/2009 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Abi-Saab et al., *Pharmacopsychiatry* 31 Suppl 2: 104-109, 1998.
Alberti et al., *Diabetic Medicine*, 15, 539-553, 1998.
Berge, *Journal of Pharmaceutical Science*, 66, 2, 1977.
Capuano et al., *Curr Med Chem* 9: 521-548, 2002.
Castner et al., *Science* 287: 2020-2022, 2000.

(Continued)

*Primary Examiner*—James O Wilson
*Assistant Examiner*—Douglas M Willis
(74) *Attorney, Agent, or Firm*—Fish & Richardson P.C.

(57) ABSTRACT

The invention relates to imidazo[1,5-a]quinoxaline derivatives having Formula IIa:

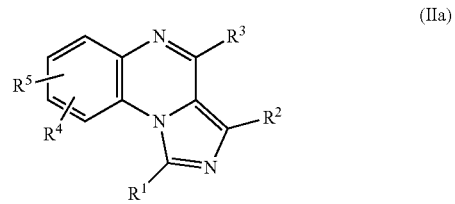

(IIa)

to processes for preparing them, to pharmaceutical preparations which comprise these compounds and to the pharmaceutical use of these compounds, which are inhibitors of phosphodiesterase 10 (PDE10), as active compounds for treating central nervous system diseases of mammals, including humans.

50 Claims, No Drawings

OTHER PUBLICATIONS

Chen et al., *Bioorg. Med. Chem. Lett.* 12, 1361-1364, 2002.
Chen et al., *Bioorg. Med. Chem. Lett.* 12, 3153-3156, 2002.
Chen et al., *J Med. Chem.* 47:4517-4545, 2004.
Colota et al., *Eur.J. Med Chem*, 30, 133-139, 1995.
Davey et al. *J Med. Chem.*, 34, 2671-2677, 1991.
Essayan, *J Allergy Clin Immunol* 108: 671-680, 2001.
Garver et al., *Life Sci* 31: 1987-1992, 1982.
Gattaz et al., *Biol Psychiatry* 19: 1229-1235, 1984.
Database CAPLUS on STN, No. 113:212016, 1990.
Database CAPLUS on STN, No. 113:115337, 1990.
Database CAPLUS on STN, No. 144:22920, 2005.
Database CAPLUS on STN, No. 141:277643, 2004.
Database CAPLUS on STN, No. 147:211834, 2007.
Database CAPLUS on STN, No. 122:305875, 1995.
Database CAPLUS on STN, No. 130:223296, 1999.
Database CAPLUS on STN, No. 99:22496, 1983.
Jentsch and Roth, *Neuropsychopharmacology* 20: 201-225, 1999.
Kaiya, *Prostaglandins Leukot Essent Fatty Acids* 46: 33-38, 1992.
Kehler, et al., Expert Opinion, pp. 47-158, 2007.
Kostowski et al. *Pharmacol Biochem Behav* 5: 15-17, 1976.
Kotera et al., *Biochem Biophys Res Commun* 261: 551-557, 1999.
Lahti et al., *Neuropsychopharmacology* 25: 455-467, 2001.
Lapiz et al., *Neurosci Behav Physiol* 33: 13-29, 2003.
Leveque et al., *J Neurosci* 20: 4011-4020, 2000.
Lindenmayer et al., *J Clin Psychiatry* 63: 931-935, 2002.
Millan, *Prog Neurobiol* 70: 83-244, 2005.
Muly, *Psychopharmacol Bull* 36: 92-105, 2002.
Mutschler et al., *Mutschler Arzneimittelwirkungen. 8th ed. Stuttgart: Wissenschaftliche Verlagsgesellschaft mbH*, 2001.
Norris, D. et al. (Tetrahedron Letters 42, 4297-4299, 2001.
Nyberg et al., *Psychopharmacology* 162: 37-41, 2002.
*Remington's Pharmaceutical Sciences*, 17th ed., Mack Publishing Company, Easton, Pa., p. 1418, 1985.
Rodefer et al. *Eur.J Neurosci* 21: 1070-1076, 2005.
Sawaguchi, *Parkinsonism Relat Disord* 7: 9-19, 2000.
Suzuki, *Pure & Appl. Chem.*, 57, 1749, 1985.
Soderling et al., *Curr. Opin. Cell Biol* 12: 174-179, 1999.
Soderling et al., *Proc Natl Acad USA* 96(12):7071-7076, 2000.
Sonogashira, *Synthesis*, 777, 1977.
Sundaram et al., *J Org. Chem.*, 72(13), 5020-5023, 2007.
The Evidence Report, Washington, DC:U.S. Department of Health and Human Services, NIH publication No. 98-4083,1998.
*William Harvey Research Conference, Porto*, Dec. 6th-8th, 2001.
Wong, G. et al., *European Journal of Pharmacology Molecular Pharmacology Section*, 289, 335-342, 1995.
Xie et al., *Neuroscience* 139: 597-607, 2006.
International Search Report and Written Opinion, dated Feb. 24, 2009, issued in International Application No. PCT/US2008/084688.
International Search Report and Written Opinion, dated Feb. 9, 2009, issued in International Application No. PCT/US2008/084689.
International Search Report and Written Opinion, dated Jun. 15, 2009, issued in International Application No. PCT/EP2008/009990.
Gupta et al., *Methods and Findings in Experimental and Clinical Pharmacology*, 27: 101-118, 2005.
Non-final office action received May 28, 2010 for U.S. Appl. No. 12/277,961, 16 pages.
Non-final office action received Jun. 16, 2010 for U.S. Appl. No. 12/323,188, 20 pages.
International Search Report and Written Opinion, dated Feb. 24, 2009, issued in International Application No. PCT/US2008/084688, 17 pages.
International Search Report and Written Opinion, dated Mar. 10, 2010, issued in International Application No. PCT/US2009/063633, 30 pages.
International Search Report and Written Opinion, dated Feb. 8, 2010, issued in International Application No. PCT/US2009/063642, 67 pages.
International Search Report and Written Opinion, dated Feb. 8, 2010, issued in International Application No. PCT/EP2008/009990, 382 pages.
Sonogashira, K. In Comprehensive Organic Synthesis; Trost, B.M.; Fleming, I.; Eds.; Pergamon Press: Oxford, 1991, vol. 3, Chapters 2,4; pp. 521-549.

* cited by examiner

SUBSTITUTED IMIDAZO[1,5-A]QUINOXALINES USEFUL AS INHIBITORS OF PHOSPHODIESTERASE 10 FOR THE TREATMENT OF NEUROLOGICAL AND OTHER DISORDERS

CROSS REFERENCE TO RELATED APPLICATIONS

This application claims the benefit of U.S. Provisional Patent Application Ser. No. 61/004,844, filed Nov. 30, 2007, the disclosure of which is incorporated herein by reference in its entirety.

FIELD OF THE INVENTION

The invention relates to imidazo[1,5-a]pyrazine derivatives, to processes for preparing them, to pharmaceutical preparations which comprise these compounds and to the pharmaceutical use of these compounds, which are inhibitors of phosphodiesterase 10, as active compounds for treating diseases of mammals including a human which can be influenced by using the compounds according to the invention to inhibit phosphodiesterase 10 activity in the central nervous system. More particularly, the invention relates to the treatment of neurologic and psychiatric disorders, for example psychosis and disorders comprising cognitive deficits as symptoms.

BACKGROUND

Psychotic disorders, especially schizophrenia, are severe mental disorders which extremely impair daily life. The symptoms of psychosis may be divided into two fractions. In the acute phase, it is predominated by hallucinations and delusions being called the positive symptoms. When the agitated phase abates the so called negative symptoms become obvious. They include cognitive deficits, social phobia, reduced vigilance, indifference and deficits in verbal learning and memory, verbal fluency and motor function.

Although several antipsychotics are available since, the present therapy of psychosis is not satisfactory. The classic antipsychotics, such as haloperidol, with a high affinity to dopamine D2 receptor show extreme side effects, such as extrapyramidal symptoms (=EPS) and do not improve the negative symptoms of schizophrenia so that they do not enable the patient to return to everyday life.

Clozapine which has emerged as a benchmark therapeutic ameliorating positive, negative and cognitive symptoms of schizophrenia and devoid of EPS shows agranulocytosis as a major, potential lethal side-effect (Capuano et al., *Curr Med Chem* 9: 521-548, 2002). Besides, there is still a high amount of therapy resistant cases (Lindenmayer et al., *J Clin Psychiatry* 63: 931-935, 2002).

In conclusion, there is still a need for developing new antipsychotics which ameliorate positive, negative and cognitive symptoms of psychosis and have a better side effect profile.

The exact pathomechanism of psychosis is not yet known. A dysfunction of several neurotransmitter systems has been shown. The two major neurotransmitter systems that are involved are the dopaminergic and the glutamatergic system. Acute psychotic symptoms may be stimulated by dopaminergic drugs (Capuano et al., *Curr Med Chem* 9: 521-548, 2002) and classical antipsychotics, like haloperidol, have a high affinity to the dopamine D2 receptor (Nyberg et al., *Psychopharmacology* 162: 37-41, 2002). Animal models based on a hyperactivity of the dopaminergic neurotransmitter system (amphetamine hyperactivity, apomorphine climbing) are used to mimic the positive symptoms of schizophrenia.

Additionally there is growing evidence that the glutamatergic neurotransmitter system plays an important role in the development of schizophrenia (Millan, *Prog Neurobiol* 70: 83-244, 2005). Thus, NMDA antagonists like phencyclidine and ketamine are able to stimulate schizophrenic symptoms in humans and rodents (Abi-Saab et al., *Pharmacopsychiatry* 31 Suppl 2: 104-109, 1998; Lahti et al., *Neuropsychopharmacology* 25: 455-467, 2001). Acute administration of phencyclidine and MK-801 induce hyperactivity, stereotypies and ataxia in rats mimicking psychotic symptoms. Moreover, in contrast to the dopaminergic models the animal models of psychosis based on NMDA antagonists do not only mimic the positive symptoms but also the negative and cognitive symptoms of psychosis (Abi-Saab et al., *Pharmacopsychiatry* 31 Suppl 2: 104-109, 1998; Jentsch and Roth, *Neuropsychopharmacology* 20: 201-225, 1999). Thus, NMDA antagonists, additionally induce cognitive deficits and social interaction deficits.

Eleven families of phosphodiesterases have been identified in mammals so far (Essayan, *J Allergy Clin Immunol* 108: 671-680, 2001). The role of PDEs in the cell signal cascade is to inactivate the cyclic nucleotides cAMP and/or cGMP (Soderling and Beavo, *Proc Natl Acad USA* 96(12):7071-7076, 2000). Since cAMP and cGMP are important second messengers in the signal cascade of G-protein-coupled receptors, PDEs are involved in a broad range of physiological mechanisms playing a role in the homeostasis of the organism.

The PDE families differ in their substrate specificity for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10 (PDE10A) is primarily expressed in the brain and here in the nucleus accumbens and the caudate putamen. Areas with moderate expression are the thalamus, hippocampus, frontal cortex and olfactory tubercle (Menniti et al., *William Harvey Research Conference*, Porto, Dec. 6-8, 2001). All these brain areas are described to participate in the pathomechanism of schizophrenia (Lapiz et al., *Neurosci Behav Physiol* 33: 13-29, 2003) so that the location of the enzyme indicates a predominate role in the pathomechanism of psychosis.

In the striatum PDE10A is predominately found in the medium spiny neurons and they are primarily associated to the postsynaptic membranes of these neurons (Xie et al., *Neuroscience* 139: 597-607, 2006). By this location PDE10A may have an important influence on the signal cascade induced by dopaminergic and glutamatergic input on the medium spiny neurons two neurotransmitter systems playing a predominate role in the pathomechanism of psychosis.

Phosphodiesterase (PDE) 10A, in particular, hydrolyses both cAMP and cGMP having a higher affinity for cAMP ($K_m$=0.05 µM) than for cGMP ($K_m$=3 µM) (Soderling et al., *Curr. Opin. Cell Biol* 12: 174-179, 1999).

Psychotic patients have been shown to have a dysfunction of cGMP and cAMP levels and its downstream substrates (Kaiya, *Prostaglandins Leukot Essent Fatty Acids* 46: 33-38, 1992; Muly, *Psychopharmacol Bull* 36: 92-105, 2002; Garver et al., *Life Sci* 31: 1987-1992, 1982). Additionally, haloperidol treatment has been associated with increased cAMP and cGMP levels in rats and patients, respectively (Leveque et al., *J Neurosci* 20: 4011-4020, 2000; Gattaz et al., *Biol Psychiatry* 19: 1229-1235, 1984). As PDE10A hydrolyses both cAMP and cGMP (Kotera et al., *Biochem Biophys Res Commun* 261: 551-557, 1999), an inhibition of PDE10A would also induce an increase of cAMP and cGMP and thereby have a similar effect on cyclic nucleotide levels as haloperidol.

The antipsychotic potential of PDE10A inhibitors is further supported by studies of Kostowski et al. (*Pharmacol Biochem Behav* 5: 15-17, 1976) who showed that papaverine, a moderate selective PDE10A inhibitor, reduces apomorphine-induced stereotypies in rats, an animal model of psychosis, and increases haloperidol-induced catalepsy in rats while concurrently reducing dopamine concentration in rat brain, activities that are also seen with classical antipsychotics. This is further supported by a patent application establishing papaverine as a PDE10A inhibitor for the treatment of psychosis (US Patent Application Pub. No. 2003/0032579).

In addition to classical antipsychotics which mainly ameliorate the positive symptoms of psychosis, PDE10A also bears the potential to improve the negative and cognitive symptoms of psychosis.

Focusing on the dopaminergic input on the medium spiny neurons, PDE10A inhibitors by up-regulating cAMP and cGMP levels act as D1 agonists and D2 antagonists because the activation of Gs-protein coupled dopamine D1 receptor increases intracellular cAMP, whereas the activation of the Gi-protein coupled dopamine D2 receptor decreases intracellular cAMP levels through inhibition of adenylyl cyclase activity (Mutschler et al., *Mutschler Arzneimittelwirkungen*. $8^{th}$ ed. Stuttgart: Wissenschaftliche Verlagsgesellschaft mbH, 2001).

Elevated intracellular cAMP levels mediated by D1 receptor signalling seems to modulate a series of neuronal processes responsible for working memory in the prefrontal cortex (Sawaguchi, *Parkinsonism Relat Disord* 7: 9-19, 2000), and it is reported that D1 receptor activation may improve working memory deficits in schizophrenic patients (Castner et al., *Science* 287: 2020-2022, 2000). Thus, it seems likely that a further enhancement of this pathway might also improve the cognitive symptoms of schizophrenia.

Further indication of an effect of PDE10A inhibition on negative symptoms of psychosis was given by Rodefer et al. (*Eur. J Neurosci* 21: 1070-1076, 2005) who could show that papaverine reverses attentional set-shifting deficits induced by subchronic administration of phencyclidine, an NMDA antagonist, in rats. Attentional deficits including an impairment of shifting attention to novel stimuli belongs to the negative symptoms of schizophrenia. In the study the attentional deficits were induced by administering phencyclidine for 7 days followed by a washout period. The PDE10A inhibitor papaverine was able to reverse the enduring deficits induced by the subchronic treatment.

The synthesis of imidazo[1,5-a]pyrido[3,2-e]pyrazinones and some medical uses are well described in patents and the literature.

The documents EP 0 400 583 and U.S. Pat. No. 5,055,465 from Berlex Laboratories, Inc. report a group of imidazoquinoxalinones, their aza analogs and a process for their preparation. These compounds have been found to have inodilatory, vasodilatory and venodilatory effects. The therapeutic activity is based on the inhibition of phosphodiesterase 3 (PDE3).

EP 0 736 532 reports pyrido[3,2-e]pyrazinones and a process for their preparation. These compounds are described to have anti-asthmatic and anti-allergic properties. Examples of this invention are inhibitors of PDE4 and PDE5.

WO 00/43392 reports the use of imidazo[1,5-a]pyrido[3,2-e]pyrazinones which are inhibitors of PDE3 and PDE5 for the therapy of erectile dysfunction, heart failure, pulmonic hypertonia and vascular diseases which are accompanied by insufficient blood supply.

Another group of pyrido[3,2-e]pyrazinones, reported in WO 01/68097 are inhibitors of PDE5 and can be used for the treatment of erectile dysfunction.

Further methods for the preparation of imidazo[1,5-a]pyrido[3,2-e]pyrazinones are described also by D. Norris et al. (*Tetrahedron Letters* 42 (2001), 4297-4299).

WO 92/22552 refers to imidazo[1,5-a]quinoxalines which are generally substituted at position 3 with a carboxylic acid group and derivatives thereof. These compounds are described to be useful as anxiolytic and sedativelhypnotic agents.

In contrast, only a limited number of imidazo[1,5-a]pyrido[3,2-e]pyrazines and their medical use are already published.

WO 99/45009 describes a group of imidazopyrazines of formula (I)

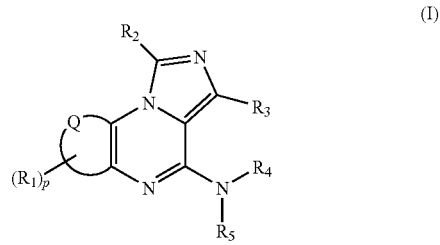

(I)

These compounds are described to be inhibitors of protein tyrosine kinases used in the treatment of protein tyrosine kinase-associated disorders such as immunologic disorders. SAR data is reported in P. Chen et al., Bioorg. Med. Chem. Lett. 12 (2002), 1361-1364 and P. Chen et al., Bioorg. Med. Chem. Lett. 12 (2002), 3153-3156.

Imidazoquinoxalines with similar substituents are claimed in U.S. Pat. No. 6,235,740 B1. Again these compounds are described to be tyrosine kinase inhibitors that can be used for the treatment of e.g. immunologic disorders.

Another group of imidazoquinoxalines is claimed in U.S. Pat. No. 6,239,133 B1 were the amino substitution (U.S. Pat. No. 6,235,740 B1) is replaced by a number of substituents linked via oxygen, sulfur or a single bond. It is claimed that these compounds would also be useful for the treatment of immunologic diseases based on kinase inhibition.

SUMMARY OF THE INVENTION

The present invention provides compounds of formula (II):

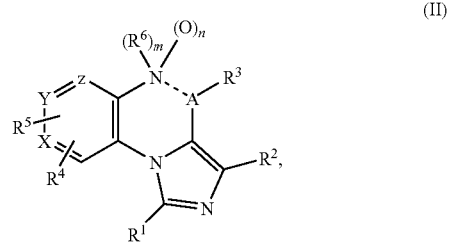

(II)

and pharmaceutically acceptable salts thereof, wherein variables $R^1$, $R^2$, $R^3$, $R^4$, $R^5$, $R^6$, X, Y, X, m, and n are as defined anywhere herein.

The present invention further provides compounds of formula (IIa)

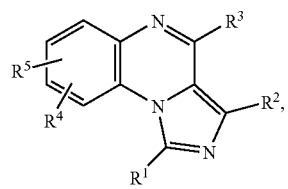

(IIa)

and pharmaceutically acceptable salts thereof, wherein variables $R^1$, $R^2$, $R^3$, $R^4$, and $R^5$ are as defined anywhere herein.

The present invention further provides methods of preparing compounds described herein.

The present invention further provides pharmaceutical compositions containing as an active agent one or more of the described compounds of the invention, or pharmaceutically acceptable salts thereof, optionally together with a pharmaceutically acceptable carrier.

The present invention further provides use of compounds of the invention, or pharmaceutically acceptable salts thereof, for the manufacture of a medicament for treating or preventing disorders associated with, accompanied by and/or caused by phosphodiesterase 10 hyperactivity and/or disorders.

The present invention further provides use of compounds of the invention, or pharmaceutically acceptable salts thereof, for the manufacture of a medicament for treating preventing central nervous system disorders.

The present invention further provides use of compounds of the invention, or pharmaceutically acceptable salts thereof, for the manufacture of a medicament for improvement of learning and memory capacities in a mammal.

The present invention further provides use of compounds of the invention, or pharmaceutically acceptable salts thereof, for the manufacture of a medicament for treating or preventing obesity, type 2 diabetes, metabolic syndrome, or glucose intolerance.

The present invention further provides use of compounds of the invention, or pharmaceutically acceptable salts thereof, for the manufacture of a medicament for reducing body fat or body weight in a patient.

The present invention further provides pharmaceutical compositions or kits which contain at least one compound of the invention, or a pharmaceutically acceptable salt thereof, in combination with at least one further pharmaceutically active compound.

The details of one or more embodiments of the invention are set forth in the accompanying the description below. Other features, objects, and advantages of the invention will be apparent from the description and drawings, and from the claims.

DETAILED DESCRIPTION

This invention relates to compounds of formula (II) and to pharmaceutically acceptable salts, solvates and derivatives such as prodrugs and metabolites thereof,

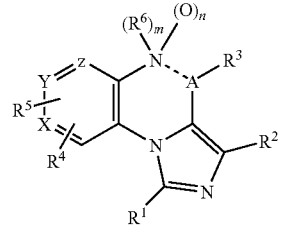

(II)

wherein the bond between A and N is a single bond or a double bond,
wherein A is C when the bond is a double bond and A is CH when the bond is a single bond,
wherein m is 0 or 1,
wherein n is 0 or 1,
wherein X, Y, and Z are independently selected from C and N, wherein not more than one of X, Y and Z can be N,
wherein $R^1$ and $R^2$ are independently selected from
H, halo,
a cyclic radical,
$C_{1-8}$ alkyl, optionally mono- or polysubstituted with halo, OH, O—$C_{1-3}$ alkyl and/or a cyclic radical,
$C_{2-8}$ alkenyl, optionally mono- or polysubstituted with halo, OH, O—$C_{1-3}$ alkyl and/or a cyclic radical,
$C_{2-8}$ alkynyl, optionally mono- or polysubstituted with halo, OH, O—$C_{1-3}$ alkyl and/or a cyclic radical,
O—$C_{1-6}$ alkyl optionally mono- or polysubstituted with halo, OH, O—$C_{1-3}$ alkyl, and/or a cyclic radical, and a saturated, monounsaturated or polyunsaturated carbocyclic ring system with 3 to 8 ring atoms, e.g. phenyl, or a heterocyclic ring system with 5 to 15 ring atoms containing at least one heteroatom selected from N including N-oxide, O and S, each optionally mono- or polysubstituted with halo, amino, $C_{1-3}$ alkylamino, di-$C_{1-3}$ alkylamino, nitro, $C_{1-3}$ alkyl, O—$C_{1-3}$ alkyl, $CF_3$, $OCF_3$, COOH, $CONH_2$, $CONHR^7$, CON$(R^7)_2$ and/or a cyclic radical, wherein $R^7$ is in each case independently $C_{1-6}$ alkyl, $C_{2-6}$ alkenyl, $C_{2-6}$ alkynyl, $C_{3-6}$ cycloalkyl, phenyl, or a heterocyclic ring system with 5 to 6 ring atoms containing at least one heteroatom selected from N,N-oxide, O and S, each optionally mono- or polysubstituted with halo, OH, O—$C_{1-3}$ alkyl and/or a cyclic radical, or two $R^7$ groups in $N(R^7)_2$ together with the N atom to which they are attached may form a saturated or unsaturated five-, six- or seven-membered ring which can contain up to 3 heteroatoms selected from N,N-oxide, S and O optionally mono- or polysubstituted with halo, $C_{1-3}$ alkyl, O—$C_{1-3}$ alkyl or aryl-$C_{1-5}$-alkyl, wherein aryl is phenyl, optionally mono- or polysubstituted with halo, nitro, $C_{1-3}$ alkyl, or O—$C_{1-3}$ alkyl, and/or a cyclic radical, wherein $R^3$ is selected from
$R^8$, $OR^8$, $SR^8$, $SOR^8$, $SO_2R^8$, $NH_2$, and $N(R^8)_2$
wherein $R^3$ is in each case independently selected from:
a cyclic radical,
$C_{1-5}$ alkyl, optionally mono- or polysubstituted with halo, OH, O—$C_{1-3}$ alkyl and/or a cyclic radical,
aryl-$C_{1-5}$-alkyl wherein aryl is phenyl, optionally mono- or polysubstituted with halo, nitro, $C_{1-3}$ alkyl, $OC_{1-3}$ alkyl, and/or a cyclic radical,
(C=O)—$C_{1-5}$ alkyl optionally mono- or polysubstituted with halo, OH, O—$C_{1-3}$ alkyl and/or a cyclic radical, or or N(R$^8$)$_2$ forms a saturated or unsaturated five-, six- or seven-membered ring which can contain up to 3 heteroatoms selected from N,N-oxide, S and O optionally mono- or polysubstituted with halo, C$_{1-3}$ alkyl, O—C$_{1-3}$ alkyl and/or aryl-C$_{1-5}$-alkyl, wherein aryl is phenyl, optionally mono- or polysubstituted with halo, nitro, C$_{1-3}$ alkyl, and/or O—C$_{1-3}$ alkyl, and/or a cyclic radical, and wherein R$^4$ and R$^5$ are in each case independently selected from:
  H,
  halo,
  a cyclic radical,
  R$^9$,
  OH or OR$^9$,
  NH(C=O)—C$_{1-3}$ alkyl, optionally mono- or polysubstituted with halo, OH, O—C$_{1-3}$ alkyl or a cyclic radical, or
  NH$_2$, NHR$^9$ and/or NR$^9$R$^{10}$, wherein R$^9$ and R$^{10}$ are independently selected from
  a cyclic radical,
  C$_{1-6}$ alkyl or C$_{3-6}$ cyclo(hetero)alkyl, optionally mono- or polysubstituted with halo, OH, O—C$_{1-3}$ alkyl and/or a cyclic radical,
  aryl-C$_{1-5}$-alkyl wherein aryl is phenyl, optionally mono- or polysubstituted with halo, amino, C$_{1-3}$ alkylamino, di-C$_{1-3}$ alkylamino, nitro, C$_{1-3}$ alkyl, OH, O—C$_{1-3}$ alkyl, NH(CO)NHCH$_3$, and/or a cyclic radical, or NR$^9$R$^{10}$ forms a saturated or unsaturated five-, six- or seven-membered ring which can contain up to 3 heteroatoms selected from N,N-oxide, S and O optionally mono- or polysubstituted with halo, amino, C$_{1-3}$ alkylamino, di-C$_{1-3}$ alkylamino, C$_{1-3}$ alkyl, O—C$_{1-3}$ alkyl and/or aryl-C$_{1-5}$-alkyl, wherein aryl is phenyl, optionally mono- or polysubstituted with halo, amino, C$_{1-3}$ alkylamino, di-C$_{1-3}$ alkylamino, nitro, C$_{1-3}$ alkyl, O—C$_{1-3}$ alkyl and/or a cyclic radical, and wherein R$^6$ is selected from:
  H, halo, C$_{1-5}$ alkyl, C$_{3-6}$ cycloalkyl and (CO)—C$_{1-5}$ alkyl, optionally mono or polysubstituted with halo, OH, O—C$_{1-3}$ alkyl and/or a cyclic radical,
  or pharmaceutically acceptable salts and derivatives thereof.

In some embodiments, compounds of the invention have formula (II)

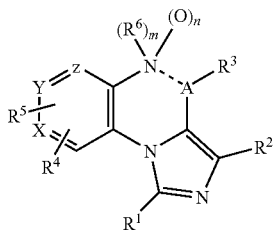

(II)

wherein the bond between A and N is a single bond or a double bond, wherein A is C when the bond is a double bond and CH when the bond is a single bond, wherein m is 0 or 1, wherein n is 0 or 1, wherein X, Y, and Z are independently selected from C and N, wherein not more than one of X, Y and Z can be N, wherein R$^1$ and R$^2$ are independently selected from:
  H, halo,
  a cyclic radical,
  C$_{1-8}$ alkyl optionally mono- or polysubstituted with halo, OH, O—C$_{1-3}$ alkyl, and/or a cyclic radical,
  C$_{2-8}$ alkenyl optionally mono- or polysubstituted with halo, OH, O—C$_{1-3}$ alkyl, and/or a cyclic radical,
  C$_{2-8}$ alkynyl optionally mono- or polysubstituted with halo, OH, O—C$_{1-3}$-alkyl, and/or a cyclic radical,
  a saturated, monounsaturated or polyunsaturated carbocyclic ring system with 3 to 8 ring atoms or a heterocyclic ring system with 5 to 15 ring atoms containing at least one heteroatom selected from N, N-oxide, O and S, wherein each ring system is optionally mono- or polysubstituted with halo, amino, C$_{1-3}$ alkylamino, di-C$_{1-3}$ alkylamino, nitro, C$_{1-3}$ alkyl, O—C$_{1-3}$ alkyl, CF$_3$, COOH, CONH$_2$, CONR$^7$, CON(R$^7$)$_2$, and/or a cyclic radical;

wherein R$^7$ is in each case independently C$_{1-6}$ alkyl, C$_{2-6}$ alkenyl, C$_{2-6}$ alkynyl, C$_{3-6}$ cycloalkyl, phenyl, or a heterocyclic ring system with 5 to 6 ring atoms containing at least one heteroatom selected from N including N-oxide, O and S, each optionally mono- or polysubstituted with halo, OH, O—C$_{1-3}$ alkyl and/or a cyclic radical, or N(R$^7$)$_2$ forms a saturated or unsaturated five-, six- or seven-membered ring which can contain up to 3 heteroatoms selected from N,N-oxide, S and O optionally mono- or polysubstituted with halo, C$_{1-3}$ alkyl, O—C$_{1-3}$ alkyl or aryl-C$_{1-5}$-alkyl, wherein aryl is phenyl, optionally mono- or polysubstituted with halo, nitro, C$_{1-3}$ alkyl, or O—C$_{1-3}$ alkyl, and/or a cyclic radical, wherein R$^3$ is selected from:
  R$^8$, OR$^8$, SR$^8$, SOR$^8$, SO$_2$R$^8$, NH$_2$, NHR$^8$ and N(R$^8$)$_2$
  wherein R$^8$ is in each case independently selected from:
  a cyclic radical,
  C$_{1-5}$ alkyl, optionally mono- or polysubstituted with halo, OH, O—C$_{1-3}$ alkyl and/or a cyclic radical,
  aryl-C$_{1-5}$-alkyl wherein aryl is phenyl, optionally mono- or polysubstituted with halo, nitro, C$_{1-3}$ alkyl, OC$_{1-3}$ alkyl, and/or a cyclic radical,
  (C=O)—C$_{1-5}$ alkyl optionally mono- or polysubstituted with halo, OH, O—C$_{1-3}$ alkyl and/or a cyclic radical, or N(R$^8$)$_2$ forms a saturated or unsaturated five-, six- or seven-membered ring which can contain up to 3 heteroatoms selected from N,N-oxide, S and O optionally mono- or polysubstituted with halo, C$_{1-3}$ alkyl, O—C$_{1-3}$ alkyl and/or aryl-C$_{1-5}$-alkyl, wherein aryl is phenyl, optionally mono- or polysubstituted with halo, nitro, C$_{1-3}$ alkyl, and/or O—C$_{1-3}$ alkyl, and/or a cyclic radical, and wherein R$^4$ and R$^5$ are in each case independently selected from:
  H,
  halo,
  a cyclic radical,
  R$^9$,
  OH or OR$^9$,
  NH(C=O)—C$_{1-3}$ alkyl optionally mono- or polysubstituted with halo, OH, O—C$_{1-3}$ alkyl, and/or a cyclic radical,
  NH$_2$, NHR$^9$, and NR$^9$R$^{10}$;

wherein R$^9$ and R$^{10}$ are independently selected from:
  a cyclic radical, $C_{1-6}$ alkyl or $C_{3-6}$ cyclo(hetero)alkyl, optionally mono- or polysubstituted with halo, OH, O—$C_{1-3}$ alkyl, and/or a cyclic radical, aryl-$C_{1-5}$ alkyl, wherein aryl is phenyl, optionally mono- or polysubstituted with halo, amino, $C_{1-3}$ alkylamino, di-$C_{1-3}$ alkylamino, nitro, $C_{1-3}$ alkyl, OH, O—$C_{1-3}$ alkyl, and/or a cyclic radical, or $R^9$ and $R^{10}$, together with the nitrogen atom to which they are attached, form a saturated or unsaturated five-, six- or seven-membered ring which contains up to 3 heteroatoms selected from N,N-oxide, S, and O optionally mono- or polysubstituted with halo, amino, $C_{1-3}$ alkylamino, di-$C_{1-3}$ alkylamino, $C_{1-3}$ alkyl, O—$C_{1-3}$ alkyl, and/or aryl-$C_{1-5}$ alkyl, wherein aryl is phenyl, optionally mono- or polysubstituted with halo, amino, $C_{1-3}$ alkylamino, di-$C_{1-3}$ alkylamino, nitro, $C_{1-3}$ alkyl, O—$C_{1-3}$ alkyl, and/or a cyclic radical; and wherein $R^6$ is selected from:
H, halo, $C_{1-5}$ alkyl, $C_{3-6}$ cycloalkyl and (CO)—$C_{1-5}$ alkyl, optionally mono or polysubstituted with halo, OH, O—$C_{1-3}$ alkyl and/or a cyclic radical, or pharmaceutically acceptable salts and derivatives thereof.

In some embodiments, the bond between A and N is a double bond.

In some embodiments, m is 0 or n is 0 or m and n both are 0.

In some embodiments, m is 0.

In some embodiments, n is 0.

In some embodiments, m and n both are 0.

In some embodiments, X and Y are C and Z is N, X and Z are C and Y is N, or Y and Z are C and X is N. In other embodiments, X, Y and Z are carbon atoms.

In some embodiments, $R^1$ is selected from:
H,
$C_{1-4}$ alkyl, particularly $C_{2-4}$ alkyl optionally mono- or polysubstituted with halo, OH, O—$C_{1-3}$ alkyl and/or a cyclic radical,
$C_3$-$C_8$ cycloalkyl, optionally mono- or polysubstituted with halo, OH, O—$C_{1-3}$ alkyl and/or a cyclic radical,
phenyl, optionally mono- or polysubstituted with halo, amino, $C_{1-3}$ alkylamino, di-$C_{1-3}$ alkylamino, nitro, $C_{1-3}$ alkyl, O—$C_{1-3}$ alkyl and/or a cyclic radical.

In some embodiments, $R^1$ is $C_{2-4}$-alkyl, cyclohexyl or phenyl, in which phenyl is optionally substituted, e.g. with $CONH_2$, $CONHR^7$ or $CON(R^7)_2$.

In some embodiments, $R^1$ is other than H.

In some embodiments, $R^2$ is H or $C_{1-4}$ alkyl, for example, methyl, optionally substituted.

In some embodiments, $R^2$ is H, $CF_3$, $CHF_2$, $CF_2H$ or a methyl group.

In some embodiments, $R^2$ is other than H.

In some embodiments, both $R^1$ and $R^2$ are other than H.

In some embodiments, $R^3$ is $C_{1-3}$ alkyl, e.g. methyl, $NH_2$, $NHR^8$ or $N(R^8)_2$.

In some embodiments, $R^3$ is $C_{1-3}$ alkyl, e.g. methyl, $NH_2$, or $N(R^8)_2$.

In some embodiments, $R^3$ is $NH_2$ or $N(R^8)_2$.

In some embodiments, $R^3$ is $R^8$, $OR^8$, or $SR^8$.

In some embodiments, $R^3$ is $C_{1-5}$ alkyl optionally mono- or polysubstituted with halo, OH, O—$C_{1-3}$ alkyl, and/or a cyclic radical.

In other embodiments, $R^3$ is $C_{1-3}$ alkyl.

In further embodiments, $R^3$ is methyl.

In some embodiments, $R^4$ and $R^5$ are independently selected from:

H, halo, such as F or Cl, $C_{1-3}$ alkyl, O—$C_{1-3}$ alkyl, $NH_2$, $NHC_{1-3}$ alkyl, wherein alkyl is optionally mono- or polysubstituted with halo, OH, O—$C_{1-3}$ alkyl, or a cyclic radical, NH(C=O)—$C_{1-3}$ alkyl, optionally mono- or polysubstituted with halo, OH, O—$C_{1-3}$ alkyl, and/or a cyclic radical, tetrahydropyrrolyl, pyrrolyl, pyrazolyl, imidazolyl, 1,2,3-triazolyl, 1,2,4-triazolyl, piperidinyl, morpholinyl, and piperazinyl, optionally mono- or polysubstituted with halo, OH, $C_{1-5}$ alkyl, or O—$C_{1-3}$ alkyl, and/or aryl-$C_{1-5}$-alkyl, wherein aryl is phenyl, optionally mono- or polysubstituted with halo, amino, $C_{1-3}$ alkylamino, di-$C_{1-3}$ alkylamino, nitro, $C_{1-3}$ alkyl, O—$C_{1-3}$ alkyl, and/or a cyclic radical, for example, any of the following:

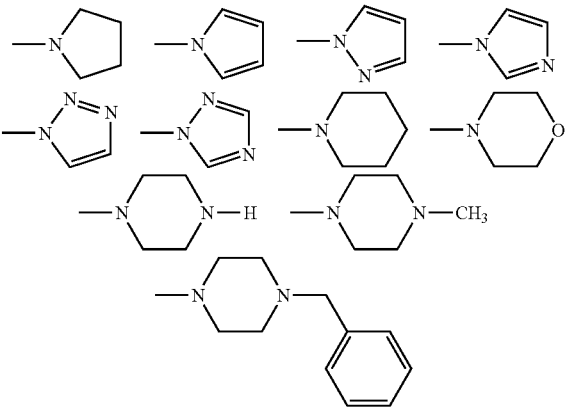

In some embodiments, $R^4$ and $R^5$ are selected from H, halo, $C_{1-3}$ alkyl, and O—$C_{1-3}$ alkyl, e.g. O-methyl, optionally substituted with a cyclic radical, e.g. $C_{3-8}$ cycloalkyl. For example, $R^4$ and/or $R^5$ may be H, F, Cl, $OCH_3$ or cyclopropylmethoxy(O—$CH_2$-cyclopropyl).

In some embodiments, a substituent $R^4$ or $R^5$ different from H is located at positions 6, 7 and/or 8 of the system, i.e. bound to Z, Y and/or position 8. In other embodiments, a substituent $R^4$ and/or $R^5$ different from H is bound to position 8 of the ring system, i.e. bound to X.

The present invention also includes compounds of formula (IIa)

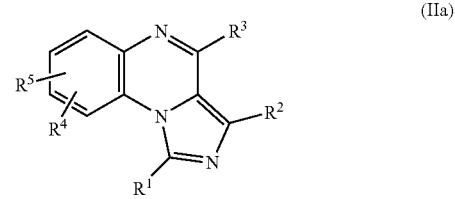

(IIa)

wherein $R^1$ and $R^2$ are independently selected from:
H, halo,
a cyclic radical,
$C_{1-8}$ alkyl optionally mono- or polysubstituted with halo, OH, O—$C_{1-3}$ alkyl, and/or a cyclic radical,
$C_{2-8}$ alkenyl optionally mono- or polysubstituted with halo, OH, O—$C_{1-3}$ alkyl, and/or a cyclic radical,
$C_{2-8}$ alkynyl optionally mono- or polysubstituted with halo, OH, O—$C_{1-3}$ alkyl, and/or a cyclic radical, O—$C_{1-6}$ alkyl optionally mono- or polysubstituted with halo, OH, O—$C_{1-3}$ alkyl, and/or a cyclic radical, and a saturated, monounsaturated or polyunsaturated carbocyclic ring system with 3 to 8 ring atoms or a heterocyclic ring system with 5 to 15 ring atoms containing at least one heteroatom selected from N,N-oxide, O and S, wherein each ring system is optionally mono- or polysubstituted with halo, amino, $C_{1-3}$ alkylamino, di-$C_{1-3}$ alkylamino, nitro, $C_{1-3}$ alkyl, O—$C_{1-3}$ alkyl, $CF_3$, $OCF_3$, COOH, $CONH_2$, $CONR^7$, CON$(R^7)_2$, and/or a cyclic radical;

wherein $R^7$ is in each case independently $C_{1-6}$ alkyl, $C_{2-6}$ alkenyl, $C_{2-6}$ alkynyl, $C_{3-6}$ cycloalkyl, phenyl, or a heterocyclic ring system with 5 to 6 ring atoms containing at least one heteroatom selected from N,N-oxide, O and S, each optionally mono- or polysubstituted with halo, OH, O—$C_{1-3}$ alkyl, and/or a cyclic radical, or two $R^7$ in group $CON(R^7)_2$, together with the nitrogen atom to which they are attached, form a saturated or unsaturated five-, six- or seven-membered ring which contains up to 3 heteroatoms selected from N,N-oxide, S, and O optionally mono- or polysubstituted with halo, $C_{1-3}$ alkyl, O—$C_{1-3}$ alkyl, and/or aryl-$C_{1-5}$ alkyl, wherein aryl is phenyl, optionally mono- or polysubstituted with halo, nitro, $C_{1-3}$ alkyl, O—$C_{1-3}$ alkyl, and/or a cyclic radical;

wherein $R^3$ is selected from $R^8$, $OR^8$, $SR^8$, $NH_2$, $NHR^8$, and $N(R^8)_2$;

wherein $R^8$ is in each case independently selected from:
 a cyclic radical,
 $C_{1-5}$ alkyl optionally mono- or polysubstituted with halo, OH, O—$C_{1-3}$ alkyl, and/or a cyclic radical,
 aryl-$C_{1-5}$ alkyl wherein aryl is phenyl, optionally mono- or polysubstituted with halo, nitro, $C_{1-3}$ alkyl, $OC_{1-3}$ alkyl, and/or a cyclic radical,
 (C=O)—$C_{1-5}$ alkyl optionally mono- or polysubstituted with halo, OH, O—$C_{1-3}$ alkyl, and/or a cyclic radical, or two $R^8$ in group $N(R^8)_2$, together with the nitrogen atom to which they are attached, form a saturated or unsaturated five-, six- or seven-membered ring which contains up to 3 heteroatoms selected from N,N-oxide, S, and O optionally mono- or polysubstituted with halo, $C_{1-3}$ alkyl, O—$C_{1-3}$ alkyl, and/or aryl-$C_{1-5}$-alkyl, wherein aryl is phenyl, optionally mono- or polysubstituted with halo, nitro, $C_{1-3}$ alkyl, O—$C_{1-3}$ alkyl, and/or a cyclic radical;

wherein $R^4$ and $R^5$ are in each case independently selected from:
 H,
 halo,
 a cyclic radical,
 $R^9$,
 OH or $OR^9$,
 NH(C=O)—$C_{1-3}$ alkyl optionally mono- or polysubstituted with halo, OH, O—$C_{1-3}$ alkyl, and/or a cyclic radical,
 $NH_2$, $NHR^9$, and $NR^9R^{10}$;

wherein $R^9$ and $R^{10}$ are independently selected from:
 a cyclic radical,
 $C_{1-6}$ alkyl or $C_{3-6}$ cyclo(hetero)alkyl, optionally mono- or polysubstituted with halo, OH, O—$C_{1-3}$ alkyl, and/or a cyclic radical,
 aryl-$C_{1-5}$ alkyl, wherein aryl is phenyl, optionally mono- or polysubstituted with halo, amino, $C_{1-3}$ alkylamino, di-$C_{1-3}$ alkylamino, nitro, $C_{1-3}$ alkyl, OH, O—$C_{1-3}$ alkyl, $NH(CO)NHCH_3$, and/or a cyclic radical, or $R^9$ and $R^{10}$, together with the nitrogen atom to which they are attached, form a saturated or unsaturated five-, six- or seven-membered ring which contains up to 3 heteroatoms selected from N,N-oxide, S, and O optionally mono- or polysubstituted with halo, amino, $C_{1-3}$ alkylamino, di-$C_{1-3}$ alkylamino, $C_{1-3}$ alkyl, O—$C_{1-3}$ alkyl, and/or aryl-$C_{1-5}$ alkyl, wherein aryl is phenyl, optionally mono- or polysubstituted with halo, amino, $C_{1-3}$ alkylamino, di-$C_{1-3}$ alkylamino, nitro, $C_{1-3}$ alkyl, O—$C_{1-3}$ alkyl, and/or a cyclic radical; pharmaceutically acceptable salts thereof.

In some embodiments, $R^1$ is $C_{1-8}$ alkyl.

In some embodiments, $R^1$ is methyl, ethyl, or propyl.

In some embodiments, $R^1$ is a saturated, monounsaturated or polyunsaturated carbocyclic ring system with 3 to 8 ring atoms, or a heterocyclic ring system with 5 to 15 ring atoms containing at least one heteroatom selected from N,N-oxide, O and S, wherein each ring system is optionally mono- or polysubstituted with halo, amino, $C_{1-3}$ alkylamino, di-$C_{1-3}$ alkylamino, nitro, $C_{1-3}$ alkyl O—$C_{1-3}$ alkyl $CF_3$, $OCF_3$, COOH, $CONH_2$, $CONR^7$, $CON(R^7)_2$, and/or a cyclic radical.

In some embodiments, $R^1$ is a saturated, monounsaturated or polyunsaturated carbocyclic ring system with 3 to 8 ring atoms, optionally mono- or polysubstituted with halo, amino, $C_{1-3}$ alkylamino, di-$C_{1-3}$ alkylamino, nitro, $C_{1-3}$ alkyl O—$C_{1-3}$ alkyl $CF_3$, $OCF_3$, COOH, $CONH_2$, $CONR^7$, CON$(R^7)_2$, and/or a cyclic radical.

In some embodiments, $R^1$ is a saturated carbocyclic ring system with 3 to 8 ring atoms.

In some embodiments, $R^1$ is cyclohexyl.

In some embodiments, $R^1$ is a polyunsaturated carbocyclic ring system with 3 to 8 ring atoms, optionally mono- or polysubstituted with halo, amino, $C_{1-3}$ alkylamino, di-$C_{1-3}$ alkylamino, nitro, $C_{1-3}$ alkyl O—$C_{1-3}$ alkyl $CF_3$, $OCF_3$, COOH, $CONH_2$, $CONR^7$, $CON(R^7)_2$, and/or a cyclic radical.

In some embodiments, $R^1$ is a polyunsaturated carbocyclic ring system with 3 to 8 ring atoms, optionally mono- or polysubstituted with halo, amino, $C_{1-3}$ alkylamino, di-$C_{1-3}$ alkylamino, nitro, $C_{1-3}$ alkyl O—$C_{1-3}$ alkyl $CF_3$, COOH, $CONH_2$, $CONR^7$, $CON(R^7)_2$, and/or a cyclic radical.

In some embodiments, $R^1$ is phenyl optionally mono- or polysubstituted with halo, $C_{1-3}$ alkyl O—$C_{1-3}$ alkyl $CF_3$, $OCF_3$, COOH, $CONH_2$, $CONR^7$, and/or $CON(R^7)_2$.

In some embodiments, $R^1$ is phenyl optionally mono- or polysubstituted with halo.

In some embodiments, $R^1$ is phenyl mono-substituted with chloro.

In some embodiments, $R^1$ is phenyl optionally mono- or polysubstituted with $C_{1-3}$ alkyl.

In some embodiments, $R^1$ is phenyl mono-substituted with methyl.

In some embodiments, $R^1$ is 2-methylphenyl.

In some embodiments, $R^1$ is a saturated, monounsaturated or polyunsaturated heterocyclic ring system with 5 to 15 ring atoms containing at least one heteroatom selected from N,N-oxide, O and S, optionally mono- or polysubstituted with halo, amino, $C_{1-3}$ alkylamino, di-$C_{1-3}$ alkylamino, nitro, $C_{1-3}$ alkyl O—$C_{1-3}$ alkyl $CF_3$, COOH, $CONH_2$, $CONR^7$, CON$(R^7)_2$, and/or a cyclic radical.

In some embodiments, $R^1$ is a polyunsaturated heterocyclic ring system with 5 to 7 ring atoms containing at least one heteroatom selected from N,N-oxide, O and S, optionally mono- or polysubstituted with halo, $C_{1-3}$ alkyl, O—$C_{1-3}$ alkyl, $CONH_2$, $CONR^7$, and/or $CON(R^7)_2$.

In some embodiments, $R^1$ is a polyunsaturated heterocyclic ring system with 5 ring atoms containing at least one heteroatom selected from N,N-oxide, O and S, optionally mono- or polysubstituted with halo, $C_{1-3}$ alkyl, $O-C_{1-3}$ alkyl, $CONH_2$, $CONR^7$, and/or $CON(R^7)_2$.

In some embodiments, $R^1$ is a polyunsaturated heterocyclic ring system with 5 ring atoms containing at least one heteroatom selected from N,N-oxide, O and S, optionally mono- or polysubstituted with $C_{1-3}$ alkyl.

In some embodiments, $R^1$ is thienyl or isoxazolyl optionally mono- or polysubstituted with $C_{1-3}$ alkyl.

In some embodiments, $R^1$ is a polyunsaturated heterocyclic ring system with 5 ring atoms containing 1 or 3 nitrogen atoms, optionally mono- or polysubstituted with $C_{1-3}$ alkyl.

In some embodiments, $R^1$ is a polyunsaturated heterocyclic ring system with 5 ring atoms containing 1 or 3 nitrogen atoms, optionally mono- or polysubstituted with methyl.

In some embodiments, $R^1$ is pyrazolyl, optionally mono- or polysubstituted with methyl.

In some embodiments, $R^1$ is pyrazolyl polysubstituted with methyl.

In some embodiments, $R^1$ is 1,3,5-trimethyl-1H-pyrazol-4-yl.

In some embodiments, $R^1$ is a polyunsaturated heterocyclic ring system with 6 ring atoms containing at least one heteroatom selected from N,N-oxide, O and S, optionally mono- or polysubstituted with halo, $C_{1-3}$ alkyl, $O-C_{1-3}$ alkyl, $CONH_2$, $CONR^7$, or $CON(R^7)_2$.

In some embodiments, $R^1$ is a polyunsaturated heterocyclic ring system with 6 ring atoms containing 1 or 3 nitrogen atoms, optionally mono- or polysubstituted with halo, $C_{1-3}$ alkyl, $O-C_{1-3}$ alkyl, $CONH_2$, $CONR^7$, or $CON(R^7)_2$.

In some embodiments, $R^1$ is a polyunsaturated heterocyclic ring system with 6 ring atoms containing 1 or 3 nitrogen atoms, optionally mono- or polysubstituted with $C_{1-3}$ alkyl.

In some embodiments, $R^1$ is a polyunsaturated heterocyclic ring system with 6 ring atoms containing 1 or 3 nitrogen atoms, optionally mono- or polysubstituted with methyl.

In some embodiments, $R^1$ is pyridinyl, optionally mono- or polysubstituted with methyl.

In some embodiments, $R^1$ is pyridinyl mono-substituted with methyl.

In some embodiments, $R^1$ is 3-methylpyridin-4-yl.

In some embodiments, $R^1$ is 2-methylpyridin-3-yl or 4-methylpyridin-3-yl.

In some embodiments, $R^2$ is $C_{1-8}$ alkyl, optionally mono- or polysubstituted with halo, $O-C_{1-3}$ alkyl or a cyclic radical.

In some embodiments, $R^2$ is $C_{1-6}$ alkyl.

In some embodiments, $R^2$ is methyl.

In some embodiments, $R^3$ is $NH_2$, $NHR^8$, or $N(R^8)_2$.

In some embodiments, $R^3$ is $NH_2$.

In some embodiments, $R^3$ is $R^8$, $OR^8$, or $SR^8$.

In some embodiments, $R^3$ is $C_{1-5}$ alkyl optionally mono- or polysubstituted with halo, OH, $O-C_{1-3}$ alkyl, or a cyclic radical.

In some embodiments, $R^3$ is $C_{1-5}$ alkyl.

In some embodiments, $R^3$ is methyl.

In some embodiments, $R^4$ and $R^5$ are independently selected from H, halo, a cyclic radical, $C_{1-6}$ alkyl, and $O-C_{1-6}$ alkyl, wherein $C_{1-6}$ alkyl and $O-C_{1-6}$ alkyl are optionally mono- or polysubstituted with halo, OH, $O-C_{1-3}$ alkyl, or a cyclic radical.

In some embodiments, $R^4$ and $R^5$ are independently selected from H, halo, a cyclic radical, $C_{1-3}$ alkyl, and $O-C_{1-3}$ alkyl, wherein $C_{1-3}$ alkyl and $O-C_{1-3}$ alkyl are optionally mono- or polysubstituted with halo or a cyclic radical.

In some embodiments, one of $R^4$ and $R^5$ is $O-C_{1-3}$ alkyl, and the other of $R^4$ and $R^5$ is H, halo, $C_{1-3}$ alkyl, or $O-C_{1-3}$ alkyl, wherein $O-C_{1-3}$ alkyl is optionally mono- or polysubstituted with a saturated carbocycle or an aromatic carbocycle. In further embodiments, the saturated carbocycle is cyclopropyl.

In some embodiments, one of $R^4$ and $R^5$ is $O-C_{1-3}$ alkyl, and the other of $R^4$ and $R^5$ is H, halo, $C_{1-3}$ alkyl or $O-C_{1-3}$ alkyl, wherein $O-C_{1-3}$ alkyl is optionally polysubstituted with halo.

In some embodiments, one of $R^4$ and $R^5$ is $OCF_3$, and the other of $R^4$ and $R^5$ is H.

In some embodiments, one of $R^4$ and $R^5$ is $C_{1-3}$ alkyl, and the other of $R^4$ and $R^5$ is H, halo, $C_{1-3}$ alkyl or $O-C_{1-3}$ alkyl, wherein $C_{1-3}$ alkyl and $O-C_{1-3}$ alkyl are polysubstituted with halo.

In some embodiments, one of $R^4$ and $R^5$ is $CF_3$, and the other of $R^4$ and $R^5$ is H.

In some embodiments, one of $R^4$ and $R^5$ is $O-C_{1-3}$ alkyl, and the other of $R^4$ and $R^5$ is halo or $O-C_{1-3}$ alkyl.

In some embodiments, one of $R^4$ and $R^5$ is $OCH_3$, and the other of $R^4$ and $R^5$ is fluoro.

In some embodiments, both $R^4$ and $R^5$ are $OCH_3$.

In some embodiments, the compounds of the invention have formula (IIb)

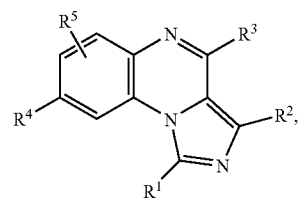

(IIb)

wherein $R^1$, $R^2$, $R^3$, $R^4$, and $R^5$ are as defined anywhere herein.

In some embodiments, the compounds of the invention have formula (IIc)

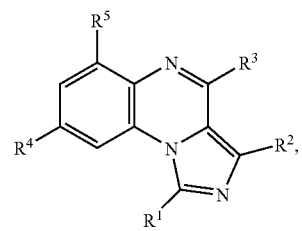

(IIc)

wherein $R^1$, $R^2$, $R^3$, $R^4$, and $R^5$ are as defined anywhere herein.

In some embodiments, $R^4$ is $OCF_3$ or $CF_3$, and $R^5$ is H.

In some embodiments, $R^4$ is $OCH_3$, and $R^5$ is fluoro or $OCH_3$.

In some embodiments, $R^4$ is F and $R^5$ is $OCH_3$.

In some embodiments, $R^4$ is F and $R^5$ is H.

In some embodiments, the compounds of the invention have formula (IIb)

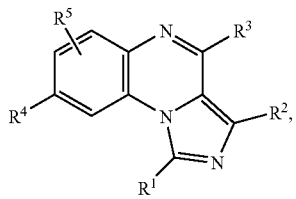

(IIb)

wherein
R¹ is selected from:
$C_{1-8}$ alkyl O—$C_{1-6}$ alkyl $C_{3-8}$ cycloalkyl, phenyl optionally mono- or polysubstituted with halo, $CF_3$, $OCF_3$, $C_{1-3}$ alkyl O—$C_{1-3}$ alkyl and/or $CONH_2$, and
a heterocyclic ring system with 5 to 6 ring atoms containing 1 to 3 nitrogen atoms, wherein the heterocyclic ring system is optionally mono- or polysubstituted with halo, $C_{1-3}$ alkyl and/or O—$C_{1-3}$ alkyl;
R³ is $C_{1-5}$ alkyl;
R⁴ and R⁵ are in each case independently selected from:
  H,
  halo,
  $C_{1-6}$ alkyl or $C_{3-6}$ cyclo(hetero)alkyl,
  OH or OR⁹,
    wherein R⁹ is:
      $C_{1-6}$ alkyl optionally mono- or polysubstituted with halo and/or a cyclic radical, or aryl-$C_{1-5}$ alkyl wherein aryl is phenyl, optionally mono- or polysubstituted with halo, amino, nitro, $C_{1-3}$ alkyl, OH, O—$C_{1-3}$ alkyl, $NH(CO)NHCH_3$, and/or a cyclic radical, or a pharmaceutically acceptable salt thereof.

Examples of specific compounds of the formula (II) include the following:
1-Ethyl-3-methyl-8-piperidin-1-yl-imidazo(1,5-a)quinoxalin-4-ylamine
1-Cyclohexyl-8-fluoro-3-methyl-imidazo(1,5-a)quinoxalin-4-ylamine
1-Ethyl-3-methyl-imidazo(1,5-a)quinoxalin-4-ylamine
3-Methyl-1-propyl-imidazo(1,5-a)quinoxalin-4-ylamine
1-Ethyl-8-fluoro-3-methyl-imidazo(1,5-a)quinoxalin-4-ylamine
8-Fluoro-3-methyl-1-propyl-imidazo(1,5-a)quinoxalin-4-ylamine
8-Methoxy-3-methyl-1-propyl-imidazo(1,5-a)quinoxalin-4-ylamine
1-(2-Chlorphenyl)-8-fluoro-3-methyl-imidazo(1,5-a)quinoxalin-4-ylamine
1-Cyclohexyl-8-methoxy-3-methyl-imidazo[1,5-a]quinoxalin-4-ylamine
8-Cyclopropylmethoxy-3-methyl-1-propyl-imidazo[1,5-a]quinoxalin-4-ylamine
1-Cyclohexyl-8-cyclopropylmethoxy-3-methyl-imidazo[1,5-a]quinoxalin-4-ylamine
7-Methoxy-3-methyl-1-propyl-imidazo[1,5-a]quinoxalin-4-ylamine
3,4-Dimethyl-1-propyl-imidazo(1,5-a)quinoxaline
8-Chloro-1-cyclohexyl-3,4-dimethyl-imidazo(1,5-a)quinoxaline
3,4-Dimethyl-1-ethyl-imidazo(1,5-a)quinoxaline
3,4-Dimethyl-1-ethyl-8-fluoro-imidazo(1,5-a)quinoxaline
3,4-Dimethyl-8-fluoro-1-propyl-imidazo(1,5-a)quinoxaline
1-Cyclohexyl-3,4-dimethyl-8-fluoro-imidazo(1,5-a)quinoxaline
1-(2-Chlorphenyl)-3,4-dimethyl-8-fluoro-imidazo(1,5-a)quinoxaline
3,4-Dimethyl-8-methoxy-1-propyl-imidazo(1,5-a)quinoxaline
3,4-Dimethyl-1-ethyl-8-(piperidin-1-yl)-imidazo(1,5-a)quinoxaline
8-Fluoro-4-methoxy-3-methyl-1-propyl-imidazo(1,5-a)quinoxaline
1-(2,5-Dichlorophenyl)-8-fluoro-3,4-dimethylimidazo[1,5-a]quinoxaline
1-(3,5-Dichlorophenyl)-8-fluoro-3,4-dimethylimidazo[1,5-a]quinoxaline
1-(3-Chlorophenyl)-8-fluoro-3,4-dimethylimidazo[1,5-a]quinoxaline
1-(2,4-Difluorophenyl)-8-fluoro-3,4-dimethylimidazo[1,5-a]quinoxaline
8-Fluoro-1-(2-methoxyphenyl)-3,4-dimethylimidazo[1,5-a]quinoxaline
8-Fluoro-1-(3-methoxyphenyl)-3,4-dimethylimidazo[1,5-a]quinoxaline
8-Fluoro-3,4-dimethyl-1-(2-methylphenyl)imidazo[1,5-a]quinoxaline
8-Fluoro-3,4-dimethyl-1-(3-methylphenyl)imidazo[1,5-a]quinoxaline
8-Fluoro-3,4-dimethyl-1-[2-(trifluoromethyl)phenyl]imidazo[1,5-a]quinoxaline
8-Fluoro-3,4-dimethyl-1-[2-(trifluoromethoxy)phenyl]imidazo[1,5-a]quinoxaline
8-Fluoro-3,4-dimethyl-1-(3-methyl-2-thienyl)imidazo[1,5-a]quinoxaline
1-(3,5-Dimethylisoxazol-4-yl)-8-fluoro-3,4-dimethylimidazo[1,5-a]quinoxaline
6-Fluoro-8-methoxy-3,4-dimethyl-1-(2-methylphenyl)-imidazo[1,5-a]quinoxaline
6-Fluoro-1-(3-fluoro-2-methylphenyl)-8-methoxy-3,4-dimethylimidazo[1,5-a]quinoxaline
1-(2-Chloro-4-fluorophenyl)-6-fluoro-8-methoxy-3,4-dimethylimidazo[1,5-a]quinoxaline
4-Fluoro-3-(6-fluoro-8-methoxy-3,4-dimethylimidazo[1,5-a]quinoxalin-1-yl)benzamide
1-(2,5-Dichlorophenyl)-3,4-dimethylimidazo[1,5-a]quinoxaline
3,4-Dimethyl-1-(2-methylphenyl)imidazo[1,5-a]quinoxaline
1-(4-Methoxypyridin-3-yl)-3,4-dimethylimidazo[1,5-a]quinoxaline
8-Cyclopropylmethoxy-3,4-dimethyl-1-propyl-imidazo[1,5-a]quinoxaline
1-Cyclohexyl-8-methoxy-3,4-dimethyl-imidazo[1,5-a]quinoxaline
1-Cyclohexyl-8-cyclopropylmethoxy-3,4-dimethyl-imidazo[1,5-a]quinoxaline
6,8-Dimethoxy-3,4-dimethyl-1-propyl-imidazo[1,5-a]quinoxaline
3,4-Dimethyl-1-propyl-6,8-bis-(2,2,2-trifluoro-ethoxy)-imidazo[1,5-a]quinoxaline
1-(2-Chloro-phenyl)-7-methoxy-3,4-dimethyl-imidazo[1,5-a]quinoxaline
7-Methoxy-3,4-dimethyl-1-propyl-imidazo[1,5-a]quinoxaline
3,4-Dimethyl-1-propyl-7-(quinolin-2-ylmethoxy)-imidazo[1,5-a]quinoxaline
1-(2-Chloro-phenyl)-6,8-bis-cyclopropylmethoxy-3,4-dimethyl-imidazo[1,5-a]quinoxaline
1-Cyclohexyl-6,8-dimethoxy-3,4-dimethyl-imidazo[1,5-a]quinoxaline 6,8-Dimethoxy-3,4-dimethyl-1-o-tolyl-imidazo[1,5-a]quinoxaline
1-(2-Chloro-phenyl)-6,8-dimethoxy-3,4-dimethyl-imidazo[1,5-a]quinoxaline
3,4-Dimethyl-1-o-tolyl-imidazo[1,5-a]quinoxaline-6,8-diol
1-(2-Chloro-phenyl)-3,4-dimethyl-imidazo[1,5-a]quinoxalin-7-ol
6,8-Bis-difluoromethoxy-3,4-dimethyl-1-o-tolyl-imidazo[1,5-a]quinoxaline
1-(2-Chloro-phenyl)-7-(2,6-difluoro-benzyloxy)-3,4-dimethyl-imidazo[1,5-a]quinoxaline
1-(2-Chloro-phenyl)-3,4-dimethyl-7-(quinolin-2-yl-methoxy)-imidazo[1,5-a]quinoxaline
1-(2-Chloro-phenyl)-3,4-dimethyl-7-(3-nitro-benzyloxy)-imidazo[1,5-a]quinoxaline
3-[1-(2-Chloro-phenyl)-3,4-dimethyl-imidazo[1,5-a]quinoxalin-7-yloxymethyl]-phenylamine
1-{3-[1-(2-Chloro-phenyl)-3,4-dimethyl-imidazo[1,5-a]quinoxalin-7-yloxymethyl]-phenyl}-3-methyl-urea
8-chloro-1-(6-fluoro-2-methylpyridin-3-yl)-3,4-dimethylimidazo[1,5-a]quinoxaline
8-chloro-3,4-dimethyl-1-(2-methylphenyl)imidazo[1,5-a]quinoxaline
3-(8-chloro-3,4-dimethylimidazo[1,5-a]quinoxalin-1-yl)benzamide
8-chloro-3,4-dimethyl-1-(4-methylpyridin-3-yl)imidazo[1,5-a]quinoxaline
8-chloro-3,4-dimethyl-1-(3-methylpyridin-4-yl)imidazo[1,5-a]quinoxaline
8-chloro-1-(2-chlorophenyl)-3,4-dimethylimidazo[1,5-a]quinoxaline
5-(8-chloro-3,4-dimethylimidazo[1,5-a]quinoxalin-1-yl)-2-fluorobenzamide
8-chloro-3,4-dimethyl-1-(1,3,5-trimethyl-1H-pyrazol-4-yl)imidazo[1,5-a]quinoxaline
6,8-difluoro-3,4-dimethyl-1-(2-methylphenyl)imidazo[1,5-a]quinoxaline
6,8-difluoro-3,4-dimethyl-1-(4-methylpyridin-3-yl)imidazo[1,5-a]quinoxaline
6,8-difluoro-3,4-dimethyl-1-(3-methylpyridin-4-yl)imidazo[1,5-a]quinoxaline
6,8-difluoro-1-methoxy-3,4-dimethylimidazo[1,5-a]quinoxaline
6-fluoro-8-methoxy-3,4-dimethyl-1-(3-methylpyridin-4-yl)imidazo[1,5-a]quinoxaline
6-fluoro-8-methoxy-3,4-dimethyl-1-(4-methylpyridin-3-yl)imidazo[1,5-a]quinoxaline
6-fluoro-8-methoxy-3,4-dimethyl-1-(2-methylpyridin-3-yl)imidazo[1,5-a]quinoxaline
1-(2-chlorophenyl)-6-fluoro-8-methoxy-3,4-dimethylimidazo[1,5-a]quinoxaline
2-fluoro-5-(6-fluoro-8-methoxy-3,4-dimethylimidazo[1,5-a]quinoxalin-1-yl)benzamide
6-fluoro-8-methoxy-3,4-dimethyl-1-(1,3,5-trimethyl-1H-pyrazol-4-yl)imidazo[1,5-a]quinoxaline
8-fluoro-6-methoxy-1-(4-methoxypyridin-3-yl)-3,4-dimethylimidazo[1,5-a]quinoxaline
8-fluoro-6-methoxy-3,4-dimethyl-1-(4-methylpyridin-3-yl)imidazo[1,5-a]quinoxaline
8-fluoro-6-methoxy-3,4-dimethyl-1-(3-methylpyridin-4-yl)imidazo[1,5-a]quinoxaline
8-fluoro-6-methoxy-3,4-dimethyl-1-(2-methylpyridin-3-yl)imidazo[1,5-a]quinoxaline
8-fluoro-6-methoxy-3,4-dimethyl-1-(2-methylphenyl)imidazo[1,5-a]quinoxaline
1-(2-chlorophenyl)-8-fluoro-6-methoxy-3,4-dimethylimidazo[1,5-a]quinoxaline
2-fluoro-5-(8-fluoro-6-methoxy-3,4-dimethylimidazo[1,5-a]quinoxalin-1-yl)benzamide
1-(2,4-dimethyl-1,3-thiazol-5-yl)-8-fluoro-6-methoxy-3,4-dimethylimidazo[1,5-a]quinoxaline
8-fluoro-6-methoxy-3,4-dimethyl-1-(1,3,5-trimethyl-1H-pyrazol-4-yl)imidazo[1,5-a]quinoxaline
8-fluoro-3,4-dimethyl-1-(2-methylphenyl)imidazo[1,5-a]quinoxalin-6-ol
6-(cyclopropylmethoxy)-8-fluoro-3,4-dimethyl-1-(2-methylphenyl)imidazo[1,5-a]quinoxaline
8-fluoro-3,4-dimethyl-1-(2-methylphenyl)-6-(2,2,2-trifluoroethoxy)imidazo[1,5-a]quinoxaline
6-ethoxy-8-fluoro-3,4-dimethyl-1-(2-methylphenyl)imidazo[1,5-a]quinoxaline
6-(difluoromethoxy)-8-fluoro-3,4-dimethyl-1-(2-methylphenyl)imidazo[1,5-a]quinoxaline
6,8-dimethoxy-3,4-dimethyl-1-(4-methylpyridin-3-yl)imidazo[1,5-a]quinoxaline
6,8-dimethoxy-3,4-dimethyl-1-(3-methylpyridin-4-yl)imidazo[1,5-a]quinoxaline
6,8-dimethoxy-3,4-dimethyl-1-(2-methylpyridin-3-yl)imidazo[1,5-a]quinoxaline
4-(6-methoxy-3,4-dimethyl-1-(3-methylpyridin-4-yl)imidazo[1,5-a]quinoxalin-8-yl)morpholine
4-(6-methoxy-3,4-dimethyl-1-(2-methylpyridin-3-yl)imidazo[1,5-a]quinoxalin-8-yl)morpholine
3,4-dimethyl-1-(3-methyl-2-thienyl)imidazo[1,5-a]quinoxaline
1-(3,5-dimethylisoxazol-4-yl)-3,4-dimethylimidazo[1,5-a]quinoxaline
3-(3,4-dimethylimidazo[1,5-a]quinoxalin-1-yl)benzamide
3-(3,4-dimethylimidazo[1,5-a]quinoxalin-1-yl)-4-fluorobenzamide
1-(6-fluoro-2-methylpyridin-3-yl)-3,4-dimethylimidazo[1,5-a]quinoxaline
3,4-dimethyl-1-(4-methylpyridin-3-yl)imidazo[1,5-a]quinoxaline
1-(2-chloro-4-fluorophenyl)-8-methoxy-3,4-dimethylimidazo[1,5-a]quinoxaline
1-[4-chloro-2-(trifluoromethyl)phenyl]-8-methoxy-3,4-dimethylimidazo[1,5-a]quinoxaline
1-(5-chloro-2-methylphenyl)-8-methoxy-3,4-dimethylimidazo[1,5-a]quinoxaline
1-(4-fluoro-2-methylphenyl)-8-methoxy-3,4-dimethylimidazo[1,5-a]quinoxaline
1-(3-fluoro-2-methylphenyl)-8-methoxy-3,4-dimethylimidazo[1,5-a]quinoxaline
8-methoxy-1-(4-methoxypyridin-3-yl)-3,4-dimethylimidazo[1,5-a]quinoxaline
8-methoxy-3,4-dimethyl-1-(4-methylpyridin-3-yl)imidazo[1,5-a]quinoxaline
3-(8-methoxy-3,4-dimethylimidazo[1,5-a]quinoxalin-1-yl)benzamide
1-(6-fluoro-2-methylpyridin-3-yl)-8-methoxy-3,4-dimethylimidazo[1,5-a]quinoxaline
4-fluoro-3-(8-methoxy-3,4-dimethylimidazo[1,5-a]quinoxalin-1-yl)benzamide
8-methoxy-3,4-dimethyl-1-(2-methylphenyl)imidazo[1,5-a]quinoxaline
3,4-dimethyl-1-(4-methylpyridin-3-yl)-8-(trifluoromethoxy)imidazo[1,5-a]quinoxaline
1-(6-fluoro-2-methylpyridin-3-yl)-3,4-dimethyl-8-(trifluoromethoxy)imidazo[1,5-a]quinoxaline
3,4-dimethyl-1-(2-methylphenyl)-8-(trifluoromethoxy)imidazo[1,5-a]quinoxaline
3,4-dimethyl-1-(3-methylpyridin-4-yl)-8-(trifluoromethoxy)imidazo[1,5-a]quinoxaline 3-[3,4-dimethyl-8-(trifluoromethoxy)imidazo[1,5-a]quinoxalin-1-yl]benzamide
3,4-dimethyl-1-(4-methylpyridin-3-yl)-8-(trifluoromethyl)imidazo[1,5-a]quinoxaline
3,4-dimethyl-1-(3-methylpyridin-4-yl)-8-(trifluoromethyl)imidazo[1,5-a]quinoxaline
1-(4-methoxypyridin-3-yl)-3,4-dimethyl-8-(trifluoromethyl)imidazo[1,5-a]quinoxaline
3,4-dimethyl-1-(2-methylpyridin-3-yl)-8-(trifluoromethyl)imidazo[1,5-a]quinoxaline
3,4-dimethyl-1-(2-methylphenyl)-8-(trifluoromethyl)imidazo[1,5-a]quinoxaline
8-chloro-7-methoxy-3,4-dimethyl-1-(2-methylphenyl)imidazo[1,5-a]quinoxaline
8-chloro-7-methoxy-3,4-dimethyl-1-(3-methylpyridin-4-yl)imidazo[1,5-a]quinoxaline
8-chloro-7-methoxy-3,4-dimethyl-1-(4-methylpyridin-3-yl)imidazo[1,5-a]quinoxaline
8-chloro-1-(2-chlorophenyl)-7-methoxy-3,4-dimethylimidazo[1,5-a]quinoxaline
8-chloro-7-methoxy-3,4-dimethyl-1-(2-methylpyridin-3-yl)imidazo[1,5-a]quinoxaline
8-chloro-7-methoxy-3,4-dimethyl-1-(1,3,5-trimethyl-1H-pyrazol-4-yl)imidazo[1,5-a]quinoxaline
8-chloro-7-ethoxy-3,4-dimethyl-1-(2-methylphenyl)imidazo[1,5-a]quinoxaline
6-methoxy-3,4-dimethyl-1-(2-methylphenyl)imidazo[1,5-a]quinoxaline
3-(8-fluoro-3,4-dimethylimidazo[1,5-a]quinoxalin-1-yl)-4-methylbenzamide
2-fluoro-5-(8-fluoro-3,4-dimethylimidazo[1,5-a]quinoxalin-1-yl)benzamide
3-fluoro-5-(8-fluoro-3,4-dimethylimidazo[1,5-a]quinoxalin-1-yl)benzamide
4-fluoro-3-(8-fluoro-3,4-dimethylimidazo[1,5-a]quinoxalin-1-yl)benzamide
8-fluoro-3,4-dimethyl-1-(2-methylphenyl)imidazo[1,5-a]quinoxaline
8-fluoro-1-(6-fluoro-2-methylpyridin-3-yl)-3,4-dimethylimidazo[1,5-a]quinoxaline
8-fluoro-1-(4-methoxypyridin-3-yl)-3,4-dimethylimidazo[1,5-a]quinoxaline
8-fluoro-3,4-dimethyl-1-(4-methylpyridin-3-yl)imidazo[1,5-a]quinoxaline
8-fluoro-3,4-dimethyl-1-(3-methylpyridin-4-yl)imidazo[1,5-a]quinoxaline
8-fluoro-3,4-dimethyl-1-pyridin-4-ylimidazo[1,5-a]quinoxaline
8-fluoro-3,4-dimethyl-1-pyridin-3-ylimidazo[1,5-a]quinoxaline and pharmaceutical salts and derivatives thereof.

The present invention also provides methods of preparing compounds of formula (II) comprising reacting an intermediate of formula (IV)

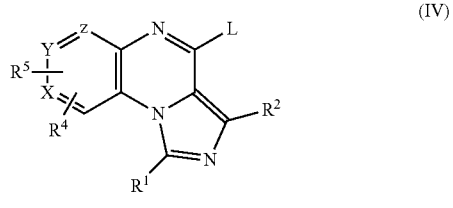

wherein L is Cl or Br and $R^1$, $R^2$, $R^4$ and $R^5$ are as defined anywhere herein; with an alkyl-, alkenyl- or alkynyl organometal reagent.

In some embodiments, the organometal reagent is alkyl magnesium bromide.

In some embodiments, the organometal reagent is ethyl magnesium bromide.

In some embodiments, the organometal reagent is methyl magnesium bromide.

DEFINITIONS

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "halo" refers to fluoro, chloro, bromo or iodo. The terms "alkyl", "alkenyl" and "alkynyl" refer to straight or branched hydrocarbon radicals with up to 8 carbon atoms preferably up to 6 carbon atoms and more preferably up to 5 carbon atoms such as methyl, ethyl, vinyl, ethynyl, propyl, isopropyl, allyl, propynyl, butyl, isobutyl, t-butyl, butenyl, butynyl etc. which may optionally be substituted as indicated above. "Alkyl" groups are saturated; an "alkenyl" group contains at least one double carbon-carbon bond; and an "alkynyl" group contains at least one triple carbon-carbon bond.

As used herein, "cyclic radical" refers to a saturated, unsaturated, or aromatic carbocycle or heterocycle, optionally mono- or polysubstituted with halo, amino, $C_{1-3}$ alkylamino, di-$C_{1-3}$ alkylamino, nitro, $C_{1-3}$ alkyl, OH, or O—$C_{1-3}$ alkyl. The cyclic radical can be a 3 to 24 membered mono- or polycyclic ring. In some embodiments, the cyclic radical is a 3-, 4-, 5-, 6-, or 7-membered ring. The cyclic radical can contain 3 to 20, or in some embodiments, 4 to 10 ring forming carbon atoms. The cyclic radical includes cyclo(hetero)alkyl, aryl and heteroaryl groups as defined below. "Cyclo(hetero)alkyl" refers to both cycloalkyl and cycloheteroalkyl groups. Cycloheteroalkyl and heteroaryl groups may, for example, contain 1 to 6, or in some embodiments, 1 to 3 ring forming heteroatoms, selected from O, N, S, and/or P. The cyclic radical can be bound via a carbon atom or optionally via a N, O, S, SO, or $SO_2$ group. An example of an aryl cyclic radical is phenyl. Examples of cycloalkyl cyclic radicals include cyclopropyl, cyclobutyl, cyclopentyl, cyclohexyl, and cycloheptyl. Examples of heteroaryl cyclic radicals include thienyl, furanyl, pyrroly, imidazolyl, triazolyl, oxazolyl, isoxazoly, pyrazolyl, thiazolyl, pyridinyl, pyrimidinyl, and the like. Examples of cycloheteroalkyl cyclic radicals include pyrrolidinyl, tetrahydrofuranyl, morpholino, thiomorpholino, piperazinyl, tetrahydrothienyl, 2,3-dihydrobenzofuryl, 1,3-benzodioxole, benzo-1,4-dioxane, piperidinyl, isoxazolidinyl, isothiazolidinyl, pyrazolidinyl, oxazolidinyl, thiazolidinyl, and imidazolidinyl. Additional examples of cyclic radicals are provided below.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, and the like. In some embodiments, an aryl group has from 6 to about 20 carbon atoms.

As used herein, "arylalkyl" refers to an alkyl group substituted by an aryl group. Example arylalkyl groups include benzyl and phenylethyl.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. A cycloalkyl group having one or more fused aromatic rings can be attached through either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

As used herein, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, a "heteroarylalkyl" group refers to an alkyl group substituted by a heteroaryl group. An example of a heteroarylalkyl group is pyridylmethyl.

As used herein, "cycloheteroalkyl" refers to a non-aromatic heterocycle where one or more of the ring-forming atoms is a heteroatom such as an O, N, or S atom. Cycloheteroalkyl groups can include mono- or polycyclic (e.g., having 2, 3 or 4 fused rings) ring systems as well as spirocycles. Example cycloheteroalkyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of cycloheteroalkyl are moieties that have one or more aromatic rings fused (i.e., having a bond in common with) to the non-aromatic heterocyclic ring, for example phthalimidyl, naphthalimidyl, and benzo derivatives of heterocycles. A cycloheteroalkyl group having one or more fused aromatic rings can be attached though either the aromatic or non-aromatic portion. Also included in the definition of cycloheteroalkyl are moieties where one or more ring-forming atoms is substituted by 1 or 2 oxo or sulfido groups. In some embodiments, the cycloheteroalkyl group has from 1 to about 20 carbon atoms, and in further embodiments from about 3 to about 20 carbon atoms. In some embodiments, the cycloheteroalkyl group contains 3 to about 20, 3 to about 14, 3 to about 7, or 5 to 6 ring-forming atoms. In some embodiments, the cycloheteroalkyl group has 1 to about 4, 1 to about 3, or 1 to 2 heteroatoms. In some embodiments, the cycloheteroalkyl group contains 0 to 3 double bonds. In some embodiments, the cycloheteroalkyl group contains 0 to 2 triple bonds.

As used herein, the term "substituted" refers to the replacement of a hydrogen moiety with a non-hydrogen moiety in a molecule or group. A molecule or group may be monosubstituted. A molecule or group may be also polysubstituted with the same or different substituents up to the valence of the molecule or group. In some embodiments, a polysubstituted molecule or group has 2, 3, 4 or 5 substituents. Where a list of substituent choices are provided, the polysubstituted molecule or group can be substituted with two or more substituents independently selected from the list The term "reacting" is meant to refer to the bringing together of the indicated reagents in such a way as to allow their molecular interaction and chemical transformation according to the thermodynamics and kinetics of the chemical system. Reacting can be facilitated, particularly for solid reagents, by using an appropriate solvent or mixture of solvents in which at least one of the reagents is at least partially soluble. Reacting is typically carried out for a suitable time and under conditions suitable to bring about the desired chemical transformation.

The invention furthermore relates to the physiologically acceptable salts, solvates and derivatives of the compounds of the invention. Derivatives of the compounds of the invention are, for example, amides, esters and ethers. Further, the term "derivative" also encompasses prodrugs and metabolites of compounds of the invention.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418 and *Journal of Pharmaceutical Science*, 66, 2 (1977), each of which is incorporated herein by reference in its entirety.

The physiologically acceptable salts may be obtained by neutralizing the bases with inorganic or organic acids or by neutralizing the acids with inorganic or organic bases. Examples of suitable inorganic acids are hydrochloric acid, sulphuric acid, phosphoric acid or hydrobromic acid, while examples of suitable organic acids are carboxylic acid, sulpho acid or sulphonic acid, such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, maleic acid, salicylic acid, 3-aminosalicylic acid, ascorbic acid, embonic acid, nicotinic acid, isonicotinic acid, oxalic acid, gluconic acid, amino acids, methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid. Examples of suitable inorganic bases are sodium hydroxide, potassium hydroxide and ammonia, while examples of suitable organic bases are amines, preferably, however, tertiary amines, such as trimethylamine, triethylamine, pyridine, N,N-dimethylaniline, quinoline, isoquinoline, α-picoline, β-picoline, γ-picoline, quinaldine and pyrimidine.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In addition, physiologically acceptable salts of the compounds of the invention can be obtained by converting derivatives which possess tertiary amino groups into the corresponding quaternary ammonium salts in a manner known per se using quaternizing agents. Examples of suitable quaternizing agents are alkyl halides, such as methyl iodide, ethyl bromide and n-propyl chloride, and also arylalkyl halides, such as benzyl chloride or 2-phenylethyl bromide.

Furthermore, in the case of the compounds of the invention which contain an asymmetric carbon atom, the invention relates to the D form, the L form and D,L mixtures and also, where more than one asymmetric carbon atom is present, to the diastereomeric forms. Those compounds of the invention which contain asymmetric carbon atoms, and which as a rule accrue as racemates, can be separated into the optically active isomers in a known manner, for example using an optically active acid. However, it is also possible to use an optically active starting substance from the outset, with a corresponding optically active or diastereomeric compound then being obtained as the end product.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Compounds of the invention can also include all isotopes of atoms occurring in the intermediates or final compounds. Isotopes include those atoms having the same atomic number but different mass numbers. For example, isotopes of hydrogen include tritium and deuterium.

The term "compound" as used herein is meant to include all stereoisomers, geometric iosomers, tautomers, and isotopes of the structures depicted.

All compounds, and pharmaceutically acceptable salts thereof, are also meant to include solvated or hydrated forms.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof.

Pharmaceutical Methods

The compounds according to the invention have been found to have pharmacologically important properties which can be used therapeutically. The compounds of the invention can be used alone, in combination with each other or in combination with other active compounds. The compounds according to the invention are inhibitors of phosphodiesterase 10. It is therefore a part of the subject-matter of this invention that the compounds of the invention and their salts and also pharmaceutical preparations which comprise these compounds or their salts, can be used for treating or preventing disorders associated with, accompanied by and/or covered by phosphodiesterase hyperactivity and/or disorders in which inhibiting phosphodiesterase 10 is of value.

Surprisingly, the compounds of the invention are potent inhibitors of the enzyme PDE10.

It is an embodiment of this invention, that compounds of the invention including their salts, solvates and prodrugs and also pharmaceutical compositions comprising an amount of a compound of the invention or one of its salts, solvates or prodrugs effective in inhibiting PDE10 can be used for the treatment of central nervous system disorders of mammals including a human.

More particularly, the invention relates to the treatment of neurological and psychiatric disorders including, but not limited to, (1) schizophrenia and other psychotic disorders; (2) mood [affective] disorders; (3) neurotic, stress-related and somatoform disorders including anxiety disorders; (4) eating disorders; sexual dysfunction comprising excessive sexual drive; (5) disorders of adult personality and behaviour; (6) disorders usually first diagnosed in infancy, childhood and adolescence; (7) mental retardation and (8) disorders of psychological development; (9) disorders comprising the symptom of cognitive deficiency in a mammal, including a human; (10) factitious disorders.

(1) Examples of schizophrenia and other psychotic disorders disorders that can be treated according to the present invention include, but are not limited to, continuous or episodic schizophrenia of different types (for instance paranoid, hebephrenic, catatonic, undifferentiated, residual, and schizophreniform disorders); schizotypal disorders (such as borderline, latent, prepsychotic, prodromal, pseudoneurotic pseudopsychopathic schizophrenia and schizotypal personality disorder); persistent delusional disorders; acute, transient and persistent psychotic disorders; induced delusional disorders; schizoaffective disorders of different type (for instance manic depressive or mixed type); puerperal psychosis and other and unspecified nonorganic psychosis.

(2) Examples of mood [affective] disorders that can be treated according to the present invention include, but are not limited to, manic episodes associated to bipolar disorder and single manic episodes, hypomania, mania with psychotic symptoms; bipolar affective disorders (including for instance bipolar affective disorders with current hypomanic and manic episodes with or without psychotic symptoms, bipolar I disorder or bipolar II disorder); depressive disorders, such as single episode or recurrent major depressive disorder of the mild moderate or severe type, depressive disorder with postpartum onset, depressive disorders with psychotic symptoms; persistent mood [affective] disorders, such as cyclothymia, dysthymia; premenstrual dysphoric disorder.

(3) Examples of disorders belonging to the neurotic, stress-related and somatoform disorders that can be treated according to the present invention include, but are not limited to, phobic anxiety disorders, for instance agoraphobia and social phobia primarily but not exclusively related to psychosis; other anxiety disorders such as panic disorders and general anxiety disorders; obsessive compulsive disorder; reaction to severe stress and adjustment disorders, such as post traumatic stress disorder; dissociative disorders and other neurotic disorders such as depersonalisation-derealisation syndrome.

(5) Examples of disorders of adult personality and behavior that can be treated according to the present invention include, but are not limited to, specific personality disorders of the paranoid, schizoid, schizotypal, antisocial, borderline, histrionic, narcissistic, avoidant, dissocial, emotionally unstable, anankastic, anxious and dependent type; mixed personality disorders; habit and impulse disorders (such as trichotillomania, pyromania, maladaptive aggression); disorders of sexual preference.

(6) Examples of disorders usually first diagnosed in infancy, childhood and adolescence that can be treated according to the present invention include, but are not limited to, hyperkinetic disorders, attentional deficit/hyperactivity disorder (AD/HD), conduct disorders; mixed disorders of conduct and emotional disorders; nonorganic enuresis, nonorganic encopresis; stereotyped movement disorder; and other specified behavioural emotional disorders, such as attention deficit disorder without hyperactivity, excessive masturbation nail-biting, nose-picking and thumb-sucking; disorders of psychological development particularly schizoid disorder of childhood and pervasive development disorders such as psychotic episodes associated to Asperger's syndrome.

Exemplary neurological disorders include neurodegenerative disorders including, without being limited to, Parkinson's disease, Huntington's disease, dementia (for example Alzheimer's disease, multi-infarct dementia, AIDS-related dementia, or fronto temperal dementia), neurodegeneration associated with cerebral trauma, neurodegeneration associated with stroke, neurodegeneration associated with cerebral infarct, hypoglycemia-induced neurodegeneration, neurodegeneration associated with epileptic seizure, neurodegeneration associated with neurotoxic poisoning or multi-system atrophy.

(8) Examples of disorders of psychological development include but are not limited to developmental disorders of speech and language, developmental disorders of scholastic skills, such as specific disorder of arithmetical skills, reading disorders and spelling disorders and other learning disorders. These disorders are predominantly diagnosed in infancy, childhood and adolescence.

(9) The phrase "cognitive deficiency" as used here in "disorder comprising as a symptom cognitive deficiency" refers to a subnormal functioning or a suboptimal functioning in one or more cognitive aspects such as memory, intellect, learning and logic ability, or attention in a particular individual comparative to other individuals within the same general age population.

Examples of disorders comprising as a symptom cognitive deficiency that can be treated according to the present invention include, but are not limited to, cognitive deficits primarily but not exclusively related to psychosis including schizophrenia, depression, age-associated memory impairment, autism, autistic spectrum disorders, fragile X syndrome, Parkinson's disease, Alzheimer's disease, multi infarct dementia, spinal cord injury, CNS hypoxia, Lewis body dementia, stroke, frontotemporal dementia, progressive supranuclear palsy Huntington's disease and in HIV disease, cerebral trauma, cardiovascular disease, drug abuse, diabetes associated cognitive impairment and mild cognitive disorder.

(11) Additionally, the invention relates to movement disorders with malfunction of basal ganglia. Examples of movement disorders with malfunction of basal ganglia that can be treated according to the present invention include, but are not limited to, different subtypes of dystonia, such as focal dystonias, multiple-focal or segmental dystonias, torsion dystonia, hemispheric, generalised and tardive dyskinesias (induced by psychopharmacological drugs), akathisias, dyskinesias such as Huntington's disease, Parkinson's disease, Lewis body disease, restless leg syndrome, PLMS.

(12) Furthermore the invention relates to the treatment of organic, including symptomatic mental disorders, especially to organic delusional (schizophrenia-like) disorders, presenil or senile psychosis associated to dementia, to psychosis in epilepsy and Parkinson's disease and other organic and symptomatic psychosis; delirium; infective psychosis; personality and behavioural disorders due to brain disease, damage and dysfunction.

(13) The invention relates to the treatment of mental and behavioural disorders due to psychoactive compounds, more particular to the treatment of psychotic disorders and residual and late-onset psychotic disorders induced by alcohol, opioids, cannabinoids, cocaine, hallucinogens, other stimulants, including caffeine, volatile solvents and other psychoactive compounds.

(14) The invention further relates to a general improvement of learning and memory capacities in a mammal, including a human.

Compounds currently used to treat schizophrenia have been associated with several undesirable side effects. These side effects include weight gain, hyperprolactinemia, elevated triglyceride levels, metabolic syndrome (markers: diabetes, hyperlipidemia, hypertension, and obesity), glucose abnormalities (such as hyperglycemia, elevated blood glucose and impaired glucose tolerance), and the exhibition of extrapyramidal symptoms. The weight gain observed with conventional atypical antipsychotics, such as risperidone and olanzapine, has been associated with an increased risk of cardiovascular disease and diabetes mellitus.

Compounds of the present invention are useful in treating schizophrenia to effect a clinically relevant improvement such as reduction of a PANSS total score in a patient, while maintaining body weight, maintaining or improving glucose levels and/or tolerance, maintaining and/or improving triglycerides levels and/or total cholesterol levels and/or maintaining an EPS profile similar to baseline measurements before administration.

The PDE10 inhibitors of the invention are further useful in the prevention and treatment of obesity, type 2 diabetes (non-insulin dependent diabetes), metabolic syndrome, glucose intolerance, and related health risks, symptoms or disorders. As such, the compounds can also be used to reduce body fat or body weight of an overweight or obese individual. In some embodiments, the PDE10 inhibitor is selective for PDE10, meaning that it is a better inhibitor of PDE10 than for any other PDE. In some embodiments, the selective PDE10 inhibitor can reduce PDE10 activity at least 10-fold or at least 100-fold compared to other PDE's.

As used herein, the terms "overweight" and "obese" are meant to refer to adult persons 18 years or older having a greater than ideal body weight (or body fat) measured by the body mass index (BMI). BMI is calculated by weight in kilograms divided by height in meters squared ($kg/m^2$) or, alternatively, by weight in pounds, multiplied by 703, divided by height in inches squared ($lbs \times 703/in^2$). Overweight individuals typically have a BMI of between 25 and 29, whereas obsess individuals typically have a BMI of 30 or more (see, e.g., National Heart, Lung, and Blood institute, Clinical Guidelines on the Identification, Evaluation, and Treatment of Overweight and Obesity in Adults, The Evidence Report, Washington, D.C.:U.S. Department of Health and Human Services, NIH publication no. 98-4083, 1998). Other means for indicating excess body weight, excess body fat, and obesity include direct measure of body fat and/or waist-to-hip ratio measurements.

The term "metabolic syndrome" is used according to its usual meaning in the art. The American Heart Association characterizes metabolic syndrome as having at least 3 of the 5 below symptoms: 1) Elevated waist circumference (>102 cm (40 inches) in men; >88 cm (35 inches) in women), 2) Elevated triglycerides (>150 mg/dL (>1.7 mmol/L) or drug treatment for elevated triglycerides), 3) Reduced HDL-C (<40 mg/dL (1.03 mmol/L) in men <50 mg/dL (1.3 mmol/L) in women or drug treatment for reduced HDL-C, 4) Elevated blood pressure (>130/85 mmHg or drug treatment for hypertension), and 5) Elevated fasting glucose (>100 mg/dL or drug treatment for elevated glucose). See, Grundy, S. M. et al., Circulation, 2005, 112 (17, e285 (online at circ.ahajournals.org/cgi/reprint/112/17/e285)). Metabolic syndrome according to the World Health Organization (See, Alberti et al., Diabet. Med. 15, 539-553, 1998) includes individuals suffering from diabetes, glucose intolerance, low fasting glucose, or insulin resistance plus two or more of 1) High blood pressure (>160/90 mmHg), 2) Hyperlipdemia (triglycerides ≧150 mg/dL or HDL cholesterol <35 mg/dL in men and <39 mg/dL in women), 3) Central obesity (waist-to-hip ratio of >0.90 for men and >0.85 for women or BMI>30 $kg/m^2$), and 4) Microalbuminuria (urinary albumin excretion rate ≧20 μg/min or an albumin-to-creatine ratio ≧20 μg/kg).

The present methods relating to reduction of body fat or body weight, as well as the treatment or prevention of obesity, type 2 diabetes (non-insulin dependent diabetes), metabolic syndrome, glucose intolerance, and related health risks, symptoms or disorders can be carried out by the administration of one or more compounds of the present invention. In some embodiments, one or more additional therapeutic agents can be administered such as anti-obesity agents. Example anti-obesity agents include apolipoprotein-B secretion/microsomal triglyceride transfer protein (apo-B/MTP) inhibitors, 11-beta-hydroxysteroid dehydrogenase-1 (11 beta-HSD type 1) inhibitors, peptide YY3-36 or analogs thereof, MCR-4 agonists, cholecystokinin-A (CCK-A) agonists, monoamine reuptake inhibitors (such as sibutramine), cannabinoid receptor-1 antagonists (such as rimona an, sympathomimetic agents, P3 adrenergic receptor agonists, 5 dopamine agonists; (such as bromocriptine), melanocyte-stimulating hormone receptor analogs, $5HT_{2C}$ agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), neuropeptide-Y receptor antagonists (e.g., NPY Y5 receptor antagonists, such as the compounds described in U.S. Pat. Nos. 6,566,367; 61649,624; 61638,942; 61605,720; 61495, 569; 61462,053; 61388,077; 6,335,345; and 6,326,375; US Pat. Appl. Publ. Nos. 2002/0151456 and 20031036652; and PCT Publication Nos. WO 031010175, WO 03/082190 and receptor agonists or antagonists, orexin receptor antagonists, glucagon-like peptide-1 receptor agonists, ciliary neurotrophic factors, human agouti-related proteins (AGRP), ghrelin receptor antagonists, histamine 3 receptor antagonists or inverse agonists, neuromedin U receptor agonists and the like. Other anti-obesity agents are readily apparent to one of ordinary skill in the art.

Representative methods for using PDE10 inhibitors for the reduction of body fat or body weight, as well as the treatment or prevention of obesity, type 2 diabetes (non-insulin dependent diabetes), metabolic syndrome, glucose intolerance, and related health risks, symptoms are reported in WO 2005/120514.

The present invention also includes method of treating pain conditions and disorders. Examples of such pain conditions and disorders include, but are not limited to, inflammatory pain, hyperalgesia, inflammatory hyperalgesia, migraine, cancer pain, osteoarthritis pain, post-surgical pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

In a further embodiment compounds of the present invention are administered in combination with one or more other agents effective for treating pain. Such agents include analgesics, non-steroidal anti-inflammatory drugs (NSAIDs), opiods and antidepressants. In various embodiments, one or more agents are selected from the group consisting of buprenorphine, naloxone, methadone, levomethadyl acetate, L-alpha acetylmethadol (LAAM), hydroxyzine, diphenoxylate, atropine, chlordiazepoxide, carbamazepine, mianserin, benzodiazepine, phenoziazine, disulfuram, acamprosate, topiramate, ondansetron, sertraline, bupropion, amantadine, amiloride, isradipine, tiagabine, baclofen, propranolol, tricyclic antidepressants, desipramine, carbamazepine, valproate, lamotrigine, doxepin, fluoxetine, imipramine, moclobemide, nortriptyline, paroxetine, sertraline, tryptophan, venlafaxine, trazodone, quetiapine, zolpidem, zopiclone, zaleplon, gabapentin, memantine, pregabalin, cannabinoids, tramadol, duloxetine, milnacipran, naltrexone, paracetamol, metoclopramide, loperamide, clonidine, lofexidine, and diazepam.

The present invention also includes methods of treating schizophrenia and other psychotic disorders, as described above, with a combination of compounds of the present invention with one or more antipsychotic agents. Examples of suitable antipsychotic agents for use in combination with the compounds of the present invention include, but are not limited to, the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), dipheyylbutylpiperidine (pimozide) and indolone (molindolone) classes of antipsychotic agents. Other antipsychotic agents with potential therapeutic value in combination with the compounds in the present invention include loxapine, sulpiride and risperidone.

The present invention further includes methods of treating depression or treatment-resistant depression with a combination of compounds of the present invention with one or more antidepressants. Examples of suitable anti-depressants for use in combination with the compounds of the present invention include, but are not limited to, norepinephrine reuptake inhibitors (tertiary and secondary amine tricyclics), selective serotonin reuptake inhibitors (SSRIs) (e.g., fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpah-adrenoreceptor antagonists, and atypical antidepressants (bupropion, lithium, nefazodone, trazodone and viloxazine).

Compositions and Administration

An effective dose of the compounds according to the invention, or their salts, is used, in addition to physiologically acceptable carriers, diluents and/or adjuvants for producing a pharmaceutical composition. The dose of the active compounds can vary depending on the route of administration, the age and weight of the patient, the nature and severity of the diseases to be treated, and similar factors. The daily dose can be given as a single dose, which is to be administered once, or be subdivided into two or more daily doses, and is as a rule 0.001-2000 mg. Particular preference is given to administering daily doses of 0.1-500 mg, e.g. 0.1-100 mg.

Suitable administration forms are oral, parenteral, intravenous, transdermal, topical, inhalative, intranasal and sublingual preparations. Particular preference is given to using oral, parenteral, e.g. intravenous or intramuscular, intranasal preparations, e.g. dry powder or sublingual, of the compounds according to the invention. The customary galenic preparation forms, such as tablets, sugar-coated tablets, capsules, dispersible powders, granulates, aqueous solutions, alcohol-containing aqueous solutions, aqueous or oily suspensions, syrups, juices or drops, are used.

Solid medicinal forms can comprise inert components and carrier substances, such as calcium carbonate, calcium phosphate, sodium phosphate, lactose, starch, mannitol, alginates, gelatine, guar gum, magnesium stearate, aluminium stearate, methyl cellulose, talc, highly dispersed silicic acids, silicone oil, higher molecular weight fatty acids, (such as stearic acid), gelatine, agar agar or vegetable or animal fats and oils, or solid high molecular weight polymers (such as polyethylene glycol); preparations which are suitable for oral administration can comprise additional flavourings and/or sweetening agents, if desired.

Liquid medicinal forms can be sterilized and/or, where appropriate, comprise auxiliary substances, such as preservatives, stabilizers, wetting agents, penetrating agents, emulsifiers, spreading agents, solubilizers, salts, sugars or sugar alcohols for regulating the osmotic pressure or for buffering, and/or viscosity regulators.

Examples of such additives are tartrate and citrate buffers, ethanol and sequestering agents (such as ethylenediaminetetraacetic acid and its non-toxic salts). High molecular weight polymers, such as liquid polyethylene oxides, microcrystalline celluloses, carboxymethyl celluloses, polyvinylpyrrolidones, dextrans or gelatine, are suitable for regulating the viscosity. Examples of solid carrier substances are starch, lactose, mannitol, methyl cellulose, talc, highly dispersed silicic acids, high molecular weight fatty acids (such as stearic acid), gelatine, agar agar, calcium phosphate, magnesium stearate, animal and vegetable fats, and solid high molecular weight polymers, such as polyethylene glycol.

Oily suspensions for parenteral or topical applications can be vegetable synthetic or semisynthetic oils, such as liquid fatty acid esters having in each case from 8 to 22 C atoms in the fatty acid chains, for example palmitic acid, lauric acid, tridecanoic acid, margaric acid, stearic acid, arachidic acid, myristic acid, behenic acid, pentadecanoic acid, linoleic acid, elaidic acid, brasidic acid, erucic acid or oleic acid, which are esterified with monohydric to trihydric alcohols having from 1 to 6 C atoms, such as methanol, ethanol, propanol, butanol, pentanol or their isomers, glycol or glycerol. Examples of such fatty acid esters are commercially available miglyols, isopropyl myristate, isopropyl palmitate, isopropyl stearate, PEG 6-capric acid, caprylic/capric acid esters of saturated fatty alcohols, polyoxyethylene glycerol trioleates, ethyl oleate, waxy fatty acid esters, such as artificial ducktail gland fat, coconut fatty acid isopropyl ester, oleyl oleate, decyl oleate, ethyl lactate, dibutyl phthalate, diisopropyl adipate, polyol fatty acid esters, inter alia. Silicone oils of differing viscosity, or fatty alcohols, such as isotridecyl alcohol, 2-octyldodecanol, cetylstearyl alcohol or oleyl alcohol, or fatty acids, such as oleic acid, are also suitable. It is furthermore possible to use vegetable oils, such as castor oil, almond oil, olive oil, sesame oil, cotton seed oil, groundnut oil or soybean oil.

Suitable solvents, gelatinizing agents and solubilizers are water or water-miscible solvents. Examples of suitable substances are alcohols, such as ethanol or isopropyl alcohol, benzyl alcohol, 2-octyldodecanol, polyethylene glycols, phthalates, adipates, propylene glycol, glycerol, di- or tripropylene glycol, waxes, methyl cellosolve, cellosolve, esters, morpholines, dioxane, dimethyl sulphoxide, dimethylformamide, tetrahydrofuran, cyclohexanone, etc.

Cellulose ethers which can dissolve or swell both in water or in organic solvents, such as hydroxypropylmethyl cellulose, methyl cellulose or ethyl cellulose, or soluble starches, can be used as film-forming agents.

Mixtures of gelatinizing agents and film-forming agents are also perfectly possible. In this case, use is made, in particular, of ionic macromolecules such as sodium carboxymethyl cellulose, polyacrylic acid, polymethacrylic acid and their salts, sodium amylopectin semiglycolate, alginic acid or propylene glycol alginate as the sodium salt, gum arabic, xanthan gum, guar gum or carrageenan. The following can be used as additional formulation aids: glycerol, paraffin of differing viscosity, triethanolamine, collagen, allantoin and novantisolic acid. Use of surfactants, emulsifiers or wetting agents, for example of Na lauryl sulphate, fatty alcohol ether sulphates, di-Na—N-lauryl-β-iminodipropionate, polyethoxylated castor oil or sorbitan monooleate, sorbitan monostearate, polysorbates (e.g. Tween), cetyl alcohol, lecithin, glycerol monostearate, polyoxyethylene stearate, alkylphenol polyglycol ethers, cetyltrimethylammonium chloride or mono-/dialkylpolyglycol ether orthophosphoric acid monoethanolamine salts can also be required for the formulation. Stabilizers, such as montmorillonites or colloidal silicic acids, for stabilizing emulsions or preventing the breakdown of active substances such as antioxidants, for example tocopherols or butylhydroxyanisole, or preservatives, such as p-hydroxybenzoic acid esters, can likewise be used for preparing the desired formulations.

Preparations for parenteral administration can be present in separate dose unit forms, such as ampoules or vials. Use is preferably made of solutions of the active compound, preferably aqueous solution and, in particular, isotonic solutions and also suspensions. These injection forms can be made available as ready-to-use preparations or only be prepared directly before use, by mixing the active compound, for example the lyophilisate, where appropriate containing other solid carrier substances, with the desired solvent or suspending agent.

Intranasal preparations can be present as aqueous or oily solutions or as aqueous or oily suspensions. They can also be present as lyophilisates which are prepared before use using the suitable solvent or suspending agent.

Inhalable preparations can present as powders, solutions or suspensions. Preferably, inhalable preparations are in the form of powders, e.g. as a mixture of the active ingredient with a suitable formulation aid such as lactose.

The preparations are produced, aliquoted and sealed under the customary antimicrobial and aseptic conditions.

As indicated above, the compounds of the invention may be administered as a combination therapy with further active agents, e.g. therapeutically active compounds useful in the treatment of central nervous system disorders. These further compounds may be PDE10 inhibitors or compounds which have an activity which is not based on PDE10 inhibition such as dopamine D2 receptor modulating agents or NMDA modulating agents.

For a combination therapy, the active ingredients may be formulated as compositions containing several active ingredients in a single dose form and/or as kits containing individual active ingredients in separate dose forms. The active ingredients used in combination therapy may be co-administered or administered separately.

EXAMPLES

The synthesis of compounds of formula (II) can start from imidazo[1,5-a]pyrazinones of formula (III):

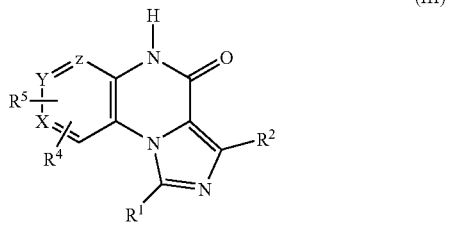

(III)

wherein X, Y, Z, $R^1$, $R^2$, $R^4$ and $R^5$ are as described above.

The preparation of compounds of formula (III) is described e.g. in J. Med. Chem. 1991, 34, 2671-2677.

According to standard procedures known from the literature and already used in WO 99/45009 compounds of formula (III) are halogenated by treatment with halogenating reagents like $POCl_3$, $PCl_3$, $PCl_5$ $SOCl_2$, $POBr_3$, $PBr_3$ or $PBr_5$, yielding e.g. 4-chloro or 4-bromo-imidazo[1,5-a]pyrazines of formula (IV).

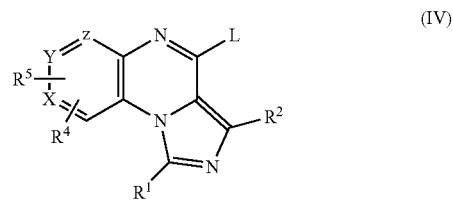

(IV)

wherein L is Cl or Br and $R^1$, $R^2$, $R^4$ and $R^5$ are as defined above.

Intermediate B1: 4-chloro-8-methoxy-3-methyl-1-propyl-imidazo[1,5-a]quinazoline

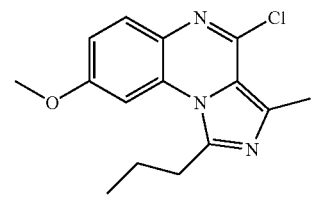

3.8 g of 8-methoxy-3-methyl-1-propyl-imidazo[1,5-a]quinazolin-4-one and 30 ml $POCl_3$ are mixed and heated up to reflux for 7 hours. After cooling to room temperature the reaction mixture is treated with 400 ml crushed ice/water and stirred for 1 hour. The product is extracted with 2×300 ml dichloromethane. The collected organic layer is washed with 300 ml water, 200 ml sodium carbonate solution (5%), 100 ml water, and dried with $Na_2SO_4$. The solvent is removed under reduced pressure.

Yield: 4.0 g m.p.: 137-140° C.

Intermediate B2: 4-Chloro-1-ethyl-3-methyl-8-piperidin-1-yl-imidazo(1,5-a)quinoxaline

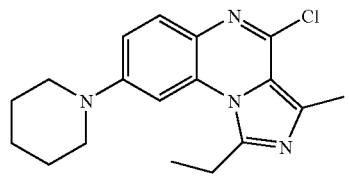

2-(2-Ethyl-4-methyl-imidazolyl)-4-piperidin-yl-nitrobenzene 5 g 2-(2-Ethyl-4-methyl-imidazolyl)-4-fluoro-nitrobenzene and 10 g piperidine were heated 30 minutes at 100° C. After cooling 150 ml ethylacetate were added. The solution was extracted three times with 50 ml water. The organic layer was evaporated to dryness. The residue is purified by chromatography (silica gel, dichloromethane/methanol=95/5).

Yield: 5.5 g

2-(2-Ethyl-4-methyl-imidazolyl)-4-piperidin-yl-aniline 5.0 g 2-(2-Ethyl-4-methyl-imidazolyl)-piperidin-yl-nitrobenzene were dissolved in 50 ml ethanol, and 0.5 g Pd/C$_5$% was added. The reaction was stirred 5 hours at 45° C. and 20 bar hydrogen. The catalyst was removed and the solution was evaporated to dryness.

Yield: 4.5 g

1-Ethyl-3-methyl-8-piperidin-yl-imidazo(1,5-a)quinoxalin-4-one 4.8 g 2-(2-Ethyl-4-methyl-imidazolyl)-4-piperidin-yl aniline and 16 g urea were heated 8 hours at 170° C. After cooling to 80° C. 80 ml water was added. After 1 hour stirring, the product is filtered off and dried at 60° C.

Yield: 4.2 g m.p.: 313-317° C.

4-Chloro-1-ethyl-3-methyl-8-piperidin-1-yl-imidazo(1,5-a)quinoxaline 3.5 g 1-Ethyl-3-methyl-8-piperidin-1-yl-imidazo(1,5-a)quinoxalin-4-one were refluxed with 25 ml phosphoroxychloride for 8 hours. 25 ml toluene were given two times and distilled to dryness. Then 100 ml ice water and 50 ml sodium carbonate solution (20%) were added.

The mixture was extracted two times with 100 ml dichloromethane. The organic layer is evaporated to dryness, the residue was purified over silica gel, dichloromethane/methanol=95/5.

Yield: 0.99 g m.p. 160-163° C.

Other intermediates B of formula (IV) can be prepared according to this procedure. Some examples are the following:

Example 1

1-Ethyl-3-methyl-8-piperidin-1-yl-imidazo(1,5-a)quinoxalin-4-ylamine

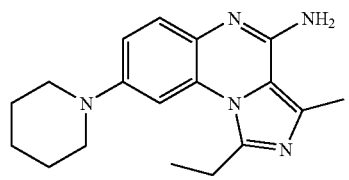

1.65 g 4-Chloro-1-ethyl-3-methyl-8-piperidin-1-yl-imidazo(1,5-a)quinoxaline and 40 ml aqueous ammonia (32%) were heated in a closed vessel for 10 hours at 135-140° C. After cooling 50 ml water and 100 ml dichloromethane were added. About 1.3 g starting material was filtered off. The organic layer is evaporated to dryness and the residue purified with silica gel, dichloromethane/methanol=9/1.

Yield: 0.52 g m.p. 199-203° C.

Example 2

1-Cyclohexyl-8-fluoro-3-methyl-imidazo(1,5-a)quinoxalin-4-yl-amine

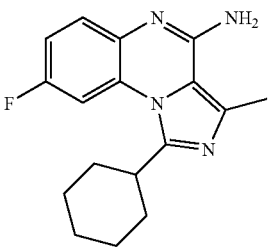

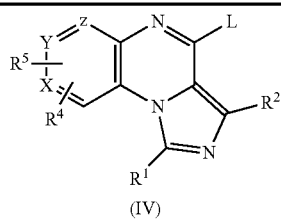

(IV)

X, Y, Z = C;

L = Cl;

R$^5$ = H

| Intermediate | R$^1$ | R$^2$ | R$^5$ | R$^4$ | m.p.[° C.] |
|---|---|---|---|---|---|
| B3 | —C$_2$H$_5$ | —CH$_3$ | H | 8-H | 125-128 |
| B4 | —C$_3$H$_7$ | —CH$_3$ | H | 8-H | 99-101 |
| B5 | —C$_2$H$_5$ | —CH$_3$ | H | 8-F | 157-160 |
| B6 | —C$_3$H$_7$ | —CH$_3$ | H | 8-F | 133-135 |
| B7 | -cyclohexyl | —CH$_3$ | H | 8-F | 205-210 |
| B8 | —C$_6$H$_4$(2-Cl) | —CH$_3$ | H | 8-F | 189-190 |
| B9 | -cyclohexyl | —CH$_3$ | H | 8-Cl | 244-248 |
| B10 | —C$_3$H$_7$ | —CH$_3$ | H | 8-piperidin-1-yl | 105-108 |
| B11 | -cyclohexyl | —CH$_3$ | H | 8-OCH$_3$ | 212-215 |
| B12 | —C$_3$H$_7$ | —CH$_3$ | H | 8-cyclopropylmethoxy | 103-105 |
| B13 | -cyclohexyl | —CH$_3$ | H | 8-cyclopropylmethoxy | 165-168 |
| B14 | —C$_3$H$_7$ | —CH$_3$ | 6-(2,3,4-trifluoroethoxy) | 8-(2,3,4-trifluoroethoxy) | 95-96 |
| B15 | —C$_3$H$_7$ | —CH$_3$ | H | 7-OCH$_3$ | 154-159 |
| B16 | —C$_2$H$_5$ | H | H | 8-Cl | 157-159 |

2-(2-Cyclohexyl-4-methyl-imidazol-1-yl)-4-fluoro-nitrobenzene 15.9 g (0.1 mol) 2,4-Difluoro-nitrobenzene, 16.5 g 2-Cyclohexyl-4-methylimidazole, 30 g potassium carbonate, and 150 ml acetonitrile were heated 24 hours at 60° C. After cooling the product was filtered off, washed with 100 ml acetonitrile, evaporated to dryness and chromatographed on silica gel with 5% MeOH/$CH_2Cl_2$.

Yield: 15.25 g m.p.: 275-280° C.

2-(2-Cyclohexyl-4-methyl-imidazol-1-yl)-4-fluoro-aniline 3.03 g 2-(2-Cyclohexyl-4-methyl-imidazol-1-yl)-4-fluoro-nitrobenzene (10 mmol) were dissolved in 50 ml ethanol, 0.5 g Raney-Nickel was added and the mixture was heated 5 hours in a closed vessel at 40-45° C. and 10 bar hydrogen. After cooling the catalyst was removed and the filtrate was distilled to dryness.

Yield: 2.61 g

1-Cyclohexyl-8-fluoro-3-methyl-imidazo(1,5-a)quinoxalin-4-one 2.73 g 2-(2-Cyclohexyl-4-methyl-imidazol-1-yl)-4-fluoro-aniline (10 mmol) and 9 g urea were heated 7 hours at 180° C. After cooling to 80° C. 50 ml water was given, the reaction was stirred 1 hour and the product was filtered off.

Yield: 2.1 g

4-Chloro-1-cyclohexyl-8-fluoro-3-methyl-imidazo(1,5-a)quinoxaline 2.1 g 1-Cyclohexyl-8-fluoro-3-methyl-imidazo(1,5-a)quinoxaline-4-one (7 mmol) and 15 ml phosphoroxychloride were refluxed for 7 hours. The cooled solution was given into 300 ml ice water stirred for 1 hour, and extracted two times with 100 ml dichloromethane. The combined organic layer was washed with 50 ml water, 50 ml 5% aqueous sodium carbonate, and 50 ml water. The organic layer was dried over sodium sulphate and distilled to dryness.

Yield: 1.55 g m.p. 205-210° C.

1-Cyclohexyl-8-fluoro-3-methyl-imidazo(1,5-a)quinoxalin-4-yl-amine 640 mg 4-Chloro-1-cyclohexyl-8-fluoro-3-methyl-imidazo(1,5-a)quinoxaline (2 mmol) and 30 ml 32% aqueous ammonia were heated 7 hours at 130-135° C. After cooling the product was filtered off, washed with water, dried and chromatographed on silica gel with 2% MeOH/$CH_2Cl_2$.

Yield: 410 mg m.p. 275-280° C.

Examples 3-8 were prepared using the same route of synthesis and reaction conditions like described above for example 2:

TABLE 1

Examples 3-8 and 38-41

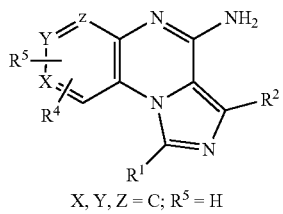

X, Y, Z = C; $R^5$ = H

| Example | $R^1$ | $R^2$ | $R^4$ | m.p. [° C.] |
|---|---|---|---|---|
| 3 | Ethyl | Methyl | H | 192-195 |
| 4 | Propyl | Methyl | H | 187-188 |
| 5 | Ethyl | Methyl | 8-F | 238-239 |
| 6 | Propyl | Methyl | 8-F | 240-243 |
| 7 | Propyl | Methyl | 8-O-Methyl | 201-203 |
| 8 | 2-Chlorphenyl | Methyl | 8-F | 193-197 |
| 38 | Cyclohexyl | Methyl | 8-$OCH_3$ | 211-212 |
| 39 | Propyl | Methyl | 8-Cyclopropylmethoxy | 163-167 |
| 40 | Cyclohexyl | Methyl | 8-Cyclopropylmethoxy | 241-242 |
| 41 | Propyl | Methyl | 8-$OCH_3$ | 175-177 |

Example 9

3,4-Dimethyl-1-propyl-imidazo(1,5-a)quinoxaline

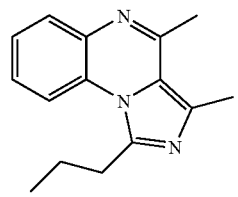

2.6 g 4-Chloro-3-methyl-1-propyl-imidazo(1,5-a)quinoxaline (10 mmol) were dissolved in 50 ml tetrahydrofuran. At room temperature 12 ml 3 M MeMgBr solution in diethylether (36 mmol) was added, followed by 8 hours stirring. After complete reaction, controlled by TLC, 0.5 ml water were added and diethylether was distilled off. The residue was distributed between 100 ml dichloromethane, 25 ml water and 25 ml 10% aqueous ammonia. The organic layer was filtered off, and distilled to dryness. The residue (2.5 g) was chromatographed on silica gel with 5% MeOH/$CH_2Cl_2$.

Yield: 1.65 g m.p.: 107-109° C.

Example 10

8-Chloro-1-cyclohexyl-3,4-dimethyl-imidazo(1,5-a)quinoxaline

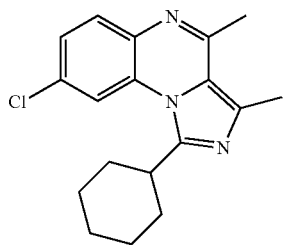

4-Chloro-2-(2-cyclohexyl-4-methyl-imidazol-1-yl)-nitrobenzene 3.75 g 4-Chloro-2-fluoro-nitrobenzene, 3.4 g 2-Cyclohexyl-4-methyl-imidazole, 50 ml acetonitrile and 5 ml triethylamine were heated 6 hours at 60° C. The solvent was distilled off followed by extraction with 100 ml ethylacetate and 2 times 50 ml water. The organic layer was distilled off and the residue chromatographed on silica gel with 5% MeOH/CH$_2$Cl$_2$.

Yield: 3.3 g

4-Chloro-2-(2-cyclohexyl-4-methyl-imidazol-1-yl)-aniline 3.2 g 4-Chloro-2-(2-cyclohexyl-4-methyl-imidazol-1-yl)-nitrobenzene, 50 ml ethanol, and 0.5 g Raney-Nickel were heated in a closed vessel with 10 bar hydrogen at 40-45° C. The catalyst was filtered off and the solvent was removed by distillation.

Yield: 2.8 g

8-Chloro-1-cyclohexyl-3-methyl-5H-imidazo(1,5-a)quinoxalin-4-one 1.45 g 4-Chloro-2-(2-cyclohexyl-4-methyl-imidazol-1-yl)-aniline were stirred in 25 ml toluene. 1.0 g Carbonyldiimidazole was added and the mixture was refluxed for 6 hours. After cooling 25 ml water was added, the product was filtered off, washed with 20 ml water and 25 ml toluene and dried.

Yield: 1.4 g
m.p.: 343-345° C.

4,8-Dichloro-1-cyclohexyl-3-methyl-imidazo(1,5-a)quinoxaline

The synthesis was carried out analogously to intermediate B1.

Yield: 1.2 g
m.p.: 244-248° C.

8-Chloro-1-cyclohexyl-3,4-dimethyl-imidazo(1,5-a)quinoxaline

The synthesis was carried out analogously to example 15.
Yield: 0.55 g
m.p.: 228-234° C.

Examples 11-17 were prepared using the same route of synthesis and reaction conditions like described above for Example 10:

TABLE 2

Examples 11-17

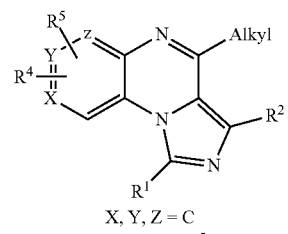

X, Y, Z = C
Alkyl = Methyl, R$^5$ = H

| Example | R$^1$ | R$^2$ | R$^4$ | m.p. [° C.] |
|---|---|---|---|---|
| 11 | Ethyl | Methyl | 8-H | 123-125 |
| 12 | Ethyl | Methyl | 8-F | 139-142 |
| 13 | Propyl | Methyl | 8-F | 140-144 |
| 14 | Cyclohexyl | Methyl | 8-F | 195-200 |
| 15 | 2-Chlorophenyl | Methyl | 8-F | 207-212 |
| 16 | Propyl | Methyl | 8-O-Methyl | 99-101 |
| 17 | Ethyl | Methyl | 8-Piperidin-1-yl | 132-134 |

Compounds of formula (II) where m and n are 0, the bond between A and N is a double bond and R$^3$ is selected from OR$^6$ or SR$^6$ as described above, can be prepared by the treatment of an intermediate of formula (IV) with the corresponding alcohols or mercaptanes HOR$^6$ or HSR$^6$.

Example 18

8-Fluoro-4-methoxy-3-methyl-1-propyl-imidazo(1,5-a)quin-oxaline

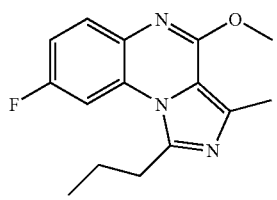

560 mg 4-Chloro-8-fluoro-3-methyl-1-propyl-imidazo(1,5-a)quinoxaline (2 mmol) were dissolved in 10 ml methanol and 500 mg potassium hydroxide were added. The reaction was heated to reflux for 2 hours, cooled, and distributed between 50 ml dichloromethane and 20 ml water. The separated water phase was extracted again with 50 ml dichloromethane. The combined organic layers were washed with 25 ml water and distilled to dryness.

Yield: 0.512 g
m.p.: 158-160° C.

Compounds of formula (II) where m and n are 0, the bond between A and N is a double bond, R$^1$ is a aromatic or heteroaromatic ring (Ar) and R$^3$ is a methyl group can be prepared by the synthesis according to Scheme I.

Scheme 1:

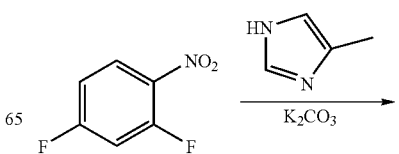

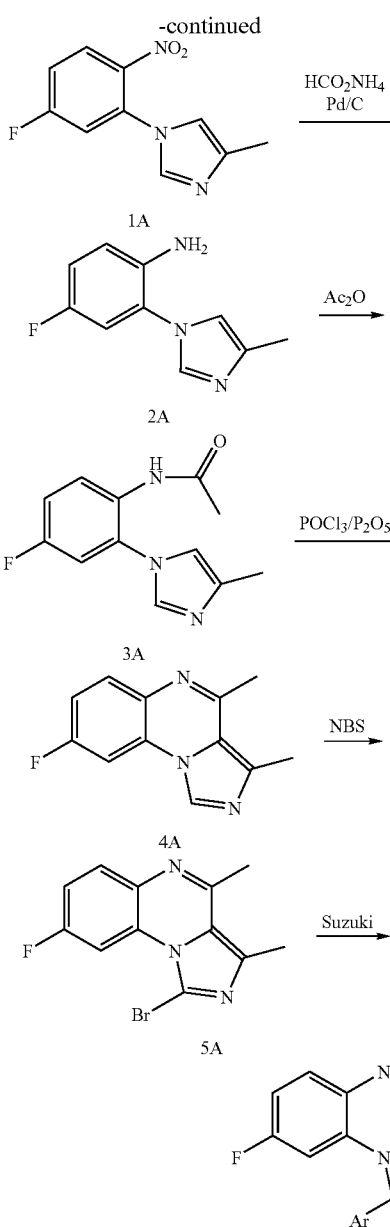

502.7 mmol) provided the product 2A as an off-white solid (18.34 g, 99% yield). EIMS 192.0 [M+H]+.

N-(4-Fluoro-2-(4-methyl-1H-imidazol-1-yl)phenyl) acetamide (3A)

Reaction of intermediate 2A (17.5 g, 91.4 mmol) and acetic anhydride (90 mL, 914 mmol) provided the product 3A as an off-white powder (13.5 g, 64% yield). EIMS 234.1 [M+H]+.

8-Fluoro-3,4-dimethylimidazo[1,5-a]quinoxaline (4A)

Reaction of intermediate 3A (13.4 g, 57.5 mmol), $P_2O_5$ (16.3 g, 115 mmol), and $POCl_3$ (100 mL) provided the product 4A as an off-white powder (1.6 g, 22% yield). EIMS 216.1 [M+H]+.

1-Bromo-8-fluoro-3,4-dimethylimidazo[1,5-a]quinoxaline (5A)

Reaction of intermediate 4A (1.55 g, 7.2 mmol) and NBS (1.92 g, 10.8 mmol) provided the product 5A as an off-white solid (1.87 g, 89% yield). EIMS 293.9 [M+H]+.

General Experimental for Suzuki Coupling

A vial or RB flask containing the mixture of bromide (1 equivalent) 5A, aryl boronic acid (1.5~2 equivalent), $K_2CO_3$ (3 equivalent) and $Pd(PPh_3)_4$ (0.05 equivalent) was vacuumed and refilled with nitrogen, followed by the addition of dioxane and $H_2O$ (reaction concentration 0.05 M, solvent ratio 3:1). The final mixture was stirred at 90° C. for 1 hour and cooled to room temperature. The reaction was quenched with saturated $NH_4Cl$, extracted with ethyl acetate. Organic solution was washed with brine and dried over magnesium sulfate. Column chromatography using 20-50% ethyl acetate in dichloromethane as eluent provided the desired coupling product.

Example 19

1-(2,5-Dichlorophenyl)-8-fluoro-3,4-dimethylimidazo[1,5-a]quinoxaline

Following the general Suzuki coupling procedure, reaction of bromide 5A (75 mg, 0.25 mmol), 2,5-dichlorophenylboronic acid (58 mg, 0.30 mmol), $K_2CO_3$ (105 mg, 0.75 mmol) and $Pd(PPh_3)_4$ (5.8 mg, 0.005 mmol) provided the coupling product as a white powder (23 mg, 25% yield). EIMS 360.0 [M+H]+.

Example 20

1-(3,5-Dichlorophenyl)-8-fluoro-3,4-dimethylimidazo[1,5-a]quinoxaline

Following the general Suzuki coupling procedure, reaction of bromide 5A (75 mg, 0.25 mmol), 3,5-dichlorophenylboronic acid (58 mg, 0.30 mmol), $K_2CO_3$ (105 mg, 0.75 mmol) and $Pd(PPh_3)_4$ (5.8 mg, 0.005 mmol) provided the coupling product as a white powder (70 mg, 78% yield). EIMS 360.0 [M+H]+.

Example 21

1-(3-Chlorophenyl)-8-fluoro-3,4-dimethylimidazo[1,5-a]quinoxaline

Following the general Suzuki coupling procedure, reaction of bromide 5A (75 mg, 0.25 mmol), 3-chlorophenylboronic Synthesis of the Intermediates:

1-(5-Fluoro-2-nitrophenyl)-4-methyl-1H-imidazole (1A)

A mixture of 2,4-difluoro-1-nitrobenzene (50 g, 314 mmol), 4-methyl-1H-imidazole (25.7 g, 314 mmol) and potassium carbonate (100 g, 725 mmol) in dichloromethane (600 mL) was stirred at room temperature for 4 days. The mixture was washed with water then dried over magnesium sulfate. Solvent was removed under reduced pressure and the residue was recrystallized in ethyl acetate to provide product 1A as a yellow solid (35 g, 50% yield). EIMS 221.9 [M+H]+.

4-Fluoro-2-(4-methyl-1H-imidazol-1-yl)aniline (2A)

Reaction of intermediate 1A (20.2 g, 91.4 mmol), 10% Pd/C (5.0 g, 4.57 mmol), and ammonium formate (34.7 g, acid (48 mg, 0.30 mmol), K$_2$CO$_3$ (105 mg, 0.75 mmol) and Pd(PPh$_3$)$_4$ (5.8 mg, 0.005 mmol) provided the coupling product as a white powder (78 mg, 96% yield). EIMS 326.0 [M+H]+.

Example 22

1-(2,4-Difluorophenyl)-8-fluoro-3,4-dimethylimidazo[1,5-a]quinoxaline

Following the general Suzuki coupling procedure, reaction of bromide 5A (75 mg, 0.25 mmol), 2,4-difluorophenylboronic acid (48 mg, 0.30 mmol), K$_2$CO$_3$ (105 mg, 0.75 mmol) and Pd(PPh$_3$)$_4$ (5.8 mg, 0.005 mmol) provided the coupling product as a white powder (41 mg, 50% yield). EIMS 328.0 [M+H]+.

Example 23

8-Fluoro-1-(2-methoxyphenyl)-3,4-dimethylimidazo[1,5-a]quinoxaline

Following the general Suzuki coupling procedure, reaction of bromide 5A (75 mg, 0.25 mmol), 2-methoxyphenylboronic acid (46 mg, 0.30 mmol), K$_2$CO$_3$ (105 mg, 0.75 mmol) and Pd(PPh$_3$)$_4$ (5.8 mg, 0.005 mmol) provided the coupling product as a white powder (72 mg, 90% yield). EIMS 322.1 [M+H]+.

Example 24

8-Fluoro-1-(3-methoxyphenyl)-3,4-dimethylimidazo[1,5-a]quinoxaline

Following the general Suzuki coupling procedure, reaction of bromide 5A (75 mg, 0.25 mmol), 3-methoxyphenylboronic acid (46 mg, 0.30 mmol), K$_2$CO$_3$ (105 mg, 0.75 mmol) and Pd(PPh$_3$)$_4$ (5.8 mg, 0.005 mmol) provided the coupling product as a white powder (40 mg, 50% yield). EIMS 322.1 [M+H]+.

Example 25

8-Fluoro-3,4-dimethyl-1-(2-methylphenyl)imidazo[1,5-a]quinoxaline

Following the general Suzuki coupling procedure, reaction of bromide 5A (75 mg, 0.25 mmol), 2-methylphenylboronic acid (42 mg, 0.30 mmol), K$_2$CO$_3$ (105 mg, 0.75 mmol) and Pd(PPh$_3$)$_4$ (5.8 mg, 0.005 mmol) provided the coupling product as a white powder (65 mg, 86% yield). EIMS 306.1 [M+H]+.

Example 26

8-Fluoro-3,4-dimethyl-1-(3-methylphenyl)imidazo[1,5-a]quinoxaline

Following the general Suzuki coupling procedure, reaction of bromide 5A (75 mg, 0.25 mmol), 3-methylphenylboronic acid (42 mg, 0.30 mmol), K$_2$CO$_3$ (105 mg, 0.75 mmol) and Pd(PPh$_3$)$_4$ (5.8 mg, 0.005 mmol) provided the coupling product as a white powder (70 mg, 92% yield). EIMS 306.1 [M+H]+.

Example 27

8-Fluoro-3,4-dimethyl-1-[2-(trifluoromethyl)phenyl]imidazo[1,5-a]quinoxaline

Following the general Suzuki coupling procedure, reaction of bromide 5A (75 mg, 0.25 mmol), 2-trifluoromethylphenylboronic acid (58 mg, 0.30 mmol), K$_2$CO$_3$ (105 mg, 0.75 mmol) and Pd(PPh$_3$)$_4$ (5.8 mg, 0.005 mmol) provided the coupling product as a white powder (44 mg, 49% yield). EIMS 360.0 [M+H]+.

Example 28

8-Fluoro-3,4-dimethyl-1-[2-(trifluoromethoxy)phenyl]imidazo[1,5-a]quinoxaline

Following the general Suzuki coupling procedure, reaction of bromide 5A (75 mg, 0.25 mmol), 2-trifluoromethoxyphenylboronic acid (62 mg, 0.30 mmol), K$_2$CO$_3$ (105 mg, 0.75 mmol) and Pd(PPh$_3$)$_4$ (5.8 mg, 0.005 mmol) provided the coupling product as a white powder (80 mg, 85% yield). EIMS 376.0 [M+H]+.

Example 29

8-Fluoro-3,4-dimethyl-1-(3-methyl-2-thienyl)imidazo[1,5-a]quinoxaline

Following the general Suzuki coupling procedure, reaction of bromide 5A (75 mg, 0.25 mmol), 3-methyl-2-thienylboronic acid (178 mg, 1.25 mmol), K$_2$CO$_3$ (105 mg, 0.75 mmol) and Pd(PPh$_3$)$_4$ (5.8 mg, 0.005 mmol) provided the coupling product as a white powder (78 mg, 100% yield). EIMS 312.0 [M+H]+.

Example 30

1-(3,5-Dimethylisoxazol-4-yl)-8-fluoro-3,4-dimethylimidazo[1,5-a]quinoxaline

Following the general Suzuki coupling procedure, reaction of bromide 5A (75 mg, 0.25 mmol), 3,5-dimethylisoxazolboronic acid (178 mg, 1.25 mmol), K$_2$CO$_3$ (105 mg, 0.75 mmol) and Pd(PPh$_3$)$_4$ (5.8 mg, 0.005 mmol) provided the coupling product as a white powder (60 mg, 77% yield). EIMS 311.1 [M+H]+.

Examples without substitution or with additional substitution at the benzo-ring were prepared as shown in Scheme 1 using un-substituted or substituted nitrobenzenes as starting materials:

1-Bromo-6-fluoro-8-methoxy-3,4-dimethylimidazo[1,5-a]quinoxaline (6A)

Following the preparation of bromide 5A, 1,3-difluoro-5-methoxy-2-nitrobenzene (see patent: WO 03/075921) was converted to 1-bromo-6-fluoro-8-methoxy-3,4-dimethylimidazo[1,5-a]quinoxaline 6A as an off-white powder. EIMS 324.0 [M+H]+.

Example 31

6-Fluoro-8-methoxy-3,4-dimethyl-1-(2-methylphenyl)-imidazo[1,5-a]quinoxaline

Following the general Suzuki coupling procedure, reaction of bromide 6A (65 mg, 0.2 mmol), 2-methylphenylboronic acid (40 mg, 0.3 mmol), $K_2CO_3$ (82 mg, 0.6 mmol) and $Pd(PPh_3)_4$ (5 mg, 0.004 mmol) provided the coupling product as an off-white powder (20 mg, 30% yield). EIMS 336.1 [M+H]+.

Example 32

6-Fluoro-1-(3-fluoro-2-methylphenyl)-8-methoxy-3,4-dimethylimidazo[1,5-a]quinoxaline Following the general Suzuki coupling procedure, reaction of bromide 6A (65 mg, 0.2 mmol), 3-fluoro-2-methylphenylboronic acid (46 mg, 0.3 mmol), $K_2CO_3$ (82 mg, 0.6 mmol) and $Pd(PPh_3)_4$ (5 mg, 0.004 mmol) provided the coupling product as an off-white powder (30 mg, 43% yield). EIMS 354.1 [M+H]+.

Example 33

1-(2-Chloro-4-fluorophenyl)-6-fluoro-8-methoxy-3,4-dimethylimidazo[1,5-a]quinoxaline Following the general Suzuki coupling procedure, reaction of bromide 6A (65 mg, 0.2 mmol), 2-chloro-4-fluorophenylboronic acid (52 mg, 0.3 mmol), $K_2CO_3$ (82 mg, 0.6 mmol) and $Pd(PPh_3)_4$ (5 mg, 0.004 mmol) provided the coupling product as an off-white powder (15 mg, 20% yield). EIMS 374.1 [M+H]+.

Example 34

4-Fluoro-3-(6-fluoro-8-methoxy-3,4-dimethylimidazo[1,5-a]quinoxalin-1-yl)benzamide Following the general Suzuki coupling procedure, reaction of bromide 6A (65 mg, 0.2 mmol), 2-fluoro-5-carbamoylphenylboronic acid (55 mg, 0.3 mmol), $K_2CO_3$ (82 mg, 0.6 mmol) and $Pd(PPh_3)_4$ (5 mg, 0.004 mmol) provided the coupling product as an off-white powder (8 mg, 11% yield). EIMS 383.1 [M+H]+.

Example 35

1-(2,5-Dichlorophenyl)-3,4-dimethylimidazo[1,5-a]quinoxaline 1-(2,5-Dichlorophenyl)-3,4-dimethylimidazo[1,5-a]quinoxaline was synthesized in a manner similar to 1-(2,5-dichlorophenyl)-8-fluoro-3,4-dimethylimidazo[1,5-a]quinoxaline starting with 2-fluoro-4-chloronitrobenzene. A white solid was recovered (0.04 g) 30% yield. MS (ES) m/z 342.0 [M+1]+

Example 36

3,4-Dimethyl-1-(2-methylphenyl)imidazo[1,5-a]quinoxaline 3,4-Dimethyl-1-(2-methylphenyl)imidazo[1,5-a]quinoxaline was synthesized in a manner similar to 1-(2,5-dichlorophenyl)-8-fluoro-3,4-dimethyl-imidazo[1,5-a]quinoxaline starting with 2-fluoro-4-chloronitrobenzene. A white solid was recovered (0.07 g) 62% yield. MS (ES) m/z 288.1 [M+1]+

Example 37

1-(4-Methoxypyridin-3-yl)-3,4-dimethylimidazo[1,5-a]quinoxaline 1-(4-Methoxypyridin-3-yl)-3,4-dimethylimidazo[1,5-a]quinoxaline was synthesized in a manner similar to compound I-(2,5-dichlorophenyl)-8-fluoro-3,4-dimethylimidazo[1,5-a]quinoxaline starting with 2-fluoro-4-chloronitrobenzene. A white solid was recovered (0.03 g) 25% yield. MS (ES) m/z 305.1 [M+1]+

Examples 38-41 were prepared using the same route of synthesis and reaction conditions as described above for Example 2:

TABLE 3

Examples 38-41

X, Y, Z = C
$R^5$ = H

| Example | $R^1$ | $R^2$ | $R^4$ | m.p. [° C.] |
|---|---|---|---|---|
| 38 | Cyclohexyl | Methyl | 8-OCH₃ | 211-212 |
| 39 | Propyl | Methyl | 8-Cyclopropylmethoxy | 163-167 |
| 40 | Cyclohexyl | Methyl | 8-Cyclopropylmethoxy | 241-242 |
| 41 | Propyl | Methyl | 8-OCH₃ | 175-177 |

Examples 42-53 were prepared using the same route of synthesis and reaction conditions as described above for Example 9:

TABLE 4

Examples 42-53

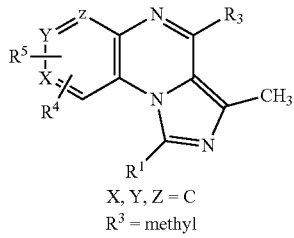

X, Y, Z = C
R³ = methyl

| Example | R¹ | R⁴ | R⁵ | m.p. [° C.] |
|---|---|---|---|---|
| 42 | Propyl | 8-Cyclopropylmethoxy | H | 110-112 |
| 43 | Cyclohexyl | 8-Methoxy | H | 165-169 |
| 44 | Cyclohexyl | 8-Cyclopropylmethoxy | H | 154-157 |
| 45 | Propyl | 8-Methoxy | 6-Methoxy | 185-187 |
| 46 | Propyl | 8-(2,2,2-Trifluoro-ethoxy) | 6-(2,2,2-Trifluoro-ethoxy) | 200-206 |
| 47 | 2-Chlorophenyl | 7-Methoxy | H | 186-188.5 |
| 48 | Propyl | 7-Methoxy | H | 111-117 |
| 50 | 2-Chlorophenyl | 8-Cyclopropylmethoxy | 6-Cyclopropylmethoxy | 180-195 |
| 51 | Cyclohexyl | 8-Methoxy | 6-Methoxy | 219-222 |
| 52 | o-Tolyl | 8-Methoxy | 6-Methoxy | 168-169 |
| 53 | 2-Chlorophenyl | 8-Methoxy | 6-Methoxy | 183-189 |

Example 54

6,8-Dihydroxy-3,4-dimethyl-1-(2-methylphenyl)-imidazo[1,5-a]quinoxaline

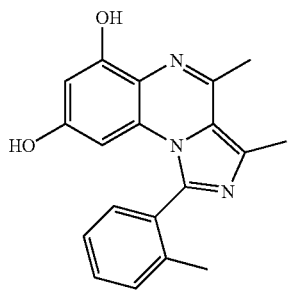

0.3 g 6,8-Dimethoxy-3,4-dimethyl-1-(2-methylphenyl)-imidazo[1,5-a]quinoxaline, 30 mL dichloromethane and 5 mL BBr₃ were heated in a closed vessel for 3 hours at 130° C. After cooling the suspension was given in 250 mL ice-cooled aqueous potassium carbonate solution. After stirring for 30 min at pH 7-9 the precipitate was filtered off, washed with water and purified with silica gel, dichloromethane/methanol 9/1.

Yield: 0.08 g
m.p. >360° C.

Example 55

1-(2-Chlorophenyl)-3,4-dimethyl-7-hydroxy-imidazo(1,5-a)quinoxaline

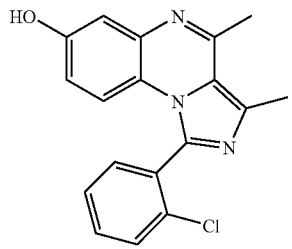

5 g 1-(2-Chlorophenyl)-3,4-dimethyl-7-methoxy-imidazo(1,5-a)quinoxaline, 100 mL dichloromethane and 12 mL BBr₃ were heated in a closed vessel for 3 hours at 110° C. After cooling the suspension was given in 600 mL ice-cooled aqueous potassium carbonate solution. After stirring for 30 min at pH 7-9 the precipitate was filtered off, washed with water and dried.

Yield: 4.52 g
m.p. 314-317° C.

Example 56

6,8-Bis-difluoromethoxy-3,4-dimethyl-1-(2-methylphenyl)-imidazo(1,5-a)quinoxaline

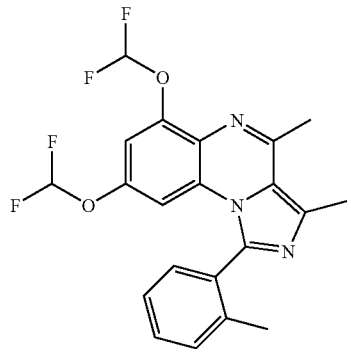

0.8 g 6,8-Dihydroxy-3,4-dimethyl-1-(2-methylphenyl)-imidazo(1,5-a)quinoxaline, 4.06 g Caesium carbonate, 40 mL N,N-dimethylformamide, and 5 mL water were stirred for 10 min followed by addition of 1.92 g Sodium chlorodifluoroacetate. The mixture was heated for 3 h at 120° C., a new portion of 1.92 g Sodium chlorodifluoroacetate was added, followed by heating for 4 h at 130° C. After cooling and stirring with 150 mL water, the precipitate was filtered off, washed with water, dried under reduced pressure and purified with silica gel, dichloromethane/methanol 95/5.

Yield: 0.25 g
m.p. 150-153° C.

Example 57

1-(2-Chloro-phenyl)-7-(2,6-difluorobenzyloxy)-3,4-dimethyl-imidazo(1,5-a)quinoxaline

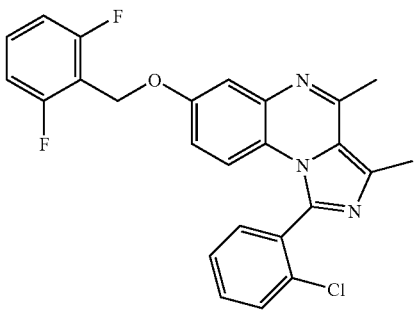

1 g 1-(2-Chloro-phenyl)-3,4-dimethyl-7-hydroxy-imidazo(1,5-a)quinoxaline, 2.24 g Caesium carbonate, 50 mL N,N-dimethylformamide, and 6 mL water were stirred for 10 min followed by addition of 0.83 g 2,6-difluorobenzylbromide. After 3 h stirring at 130° C. the reaction mixture was given into 150 mL water, filtered off, washed with water, dried under reduced pressure, and purified with silica gel, dichloromethane/methanol=95/5.

Yield: 0.97 g
m.p. 211-214° C.

Example 58

1-(2-Chloro-phenyl)-7-(quinolin-2-ylmethoxy)-3,4-dimethyl-imidazo(1,5-a)quinoxaline

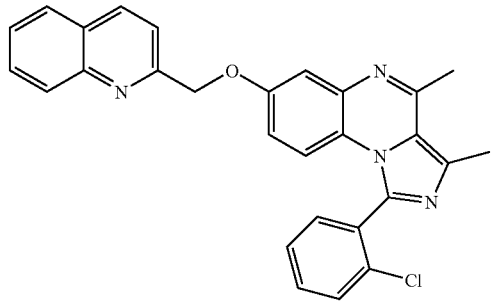

1 g 1-(2-Chloro-phenyl)-3,4-dimethyl-7-hydroxy-imidazo(1,5-a)quinoxaline, 2.24 g Caesium carbonate, 50 mL N,N-dimethylformamide, 6 mL water, and 0.86 g 2-Chloro-methylquinoline hydrochloride were stirred for 3 h at 130° C. The reaction mixture was given into 150 mL water, filtered off, washed with water, dried under reduced pressure, and purified with silica gel, dichloromethane/methanol=95/5.

Yield: 0.98 g
m.p. 162-163.5° C.

The following example is prepared using the same route of synthesis and reaction conditions as described above for Example 58:

Example 49

3,4-Dimethyl-1-propyl-7-(quinolin-2-ylmethoxy)-imidazo(1,5-a)quinoxaline

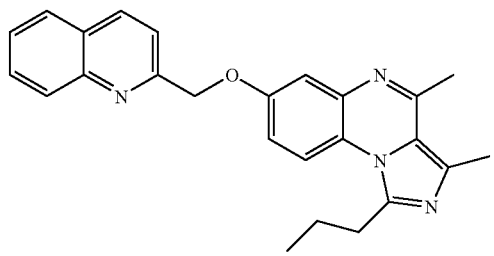

Yield: 25%
m.p. 134-136° C.

Example 59

1-(2-Chloro-phenyl)-3,4-dimethyl-7-(3-nitrobenzyloxy)-imidazo(1,5-a)quinoxaline

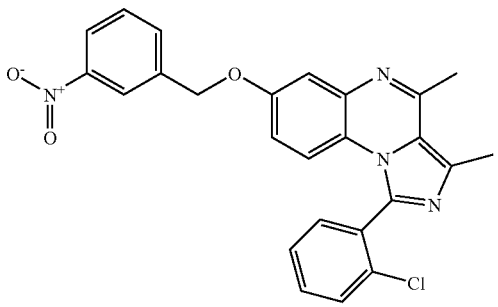

1.5 g 1-(2-Chloro-phenyl)-3,4-dimethyl-7-hydroxy-imidazo(1,5-a)quinoxaline, 3.36 g Caesium carbonate, 80 mL N,N-dimethylformamide, and 9 mL water were stirred for 10 min followed by addition of 1.3 g 3-nitro-benzylbromide. After 3 h stirring at 120° C. the reaction mixture was given into 250 mL water, filtered off, washed with water, dried under reduced pressure.

Yield: 2.1 g m.p. 211-214° C.

Example 60

7-(3-Aminobenzyloxy)-1-(2-chlorophenyl)-3,4-dimethyl-imidazo(1,5-a)quinoxaline

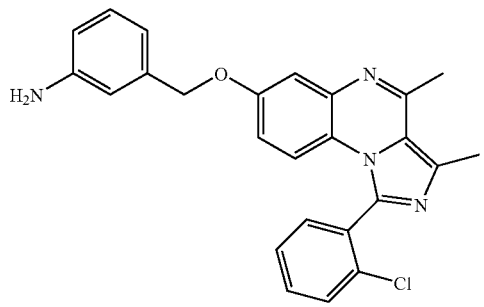

2.0 g 1-(2-Chlorophenyl)-3,4-dimethyl-7-(3-nitrobenzyloxy)-imidazo(1,5-a)quinoxaline was dissolved in 50 mL methanol, 0.4 g Raney Nickel was added followed by drop-wise addition of 2.1 mL hydrazine hydrate. The reaction mixture was stirred 1 h at 40° C. and 10 min at reflux. After cooling the catalyst was filtered off, the solvent was removed by distillation and the residue was re-crystallised from 2-propanol.

Yield: 1.1 g m.p. 168-170° C.

Example 61

N-1-{3-[1-(2-Chlorophenyl)-3,4-dimethyl-imidazo(1,5-a)quinoxalin-7-yloxymethyl]-phenyl}-N'-methyl-urea

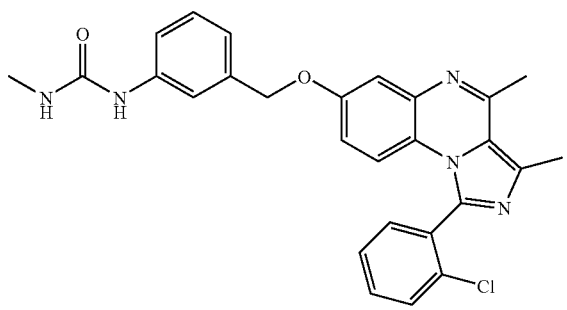

To a suspension of 1.23 g 7-(3-Aminobenzyloxy)-1-(2-chlorophenyl)-3,4-dimethyl-imidazo(1,5-a)quinoxaline in 50 mL acetonitrile and 0.7 mL triethylamine 0.5 g methylaminoformylchloride was added at 0° C. After stirring 1 h at room temperature the solvent was removed by distillation, the residue was stirred for 30 min in 100 mL water, filtered off, and dried under reduced pressure.

Yield: 1.1 g m.p. 136-139° C.

1-Bromo-8-chloro-3,4-dimethylimidazo[1,5-a]quinoxaline (7A)

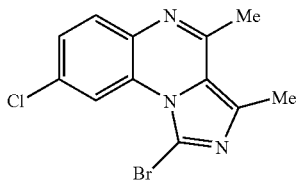

4-Chloro-2-fluoro-1-nitrobenzene was converted to 1-bromo-8-chloro-3,4-dimethylimidazo[1,5-a]quinoxaline (7A) according to Scheme 1, Example 19, and was obtained as an off-white powder. EIMS 309.9 [M+H]+.

Examples 62-69 were prepared according to the general Suzuki coupling procedure for Example 19, using 1-bromo-8-chloro-3,4-dimethylimidazo[1,5-a]quinoxaline (7A).

TABLE 5

Examples 62-69

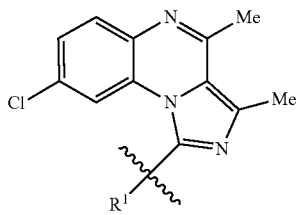

| Example | R[1] | Chemical Name | MS [M + 1]+ |
|---|---|---|---|
| 62 | 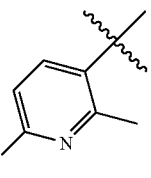 | 8-chloro-1-(6-fluoro-2-methylpyridin-3-yl)-3,4-dimethylimidazo[1,5-a]quinoxaline | 341.1 |
| 63 | 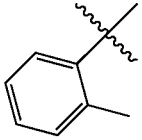 | 8-chloro-3,4-dimethyl-1-(2-methylphenyl)imidazo[1,5-a]quinoxaline | 322.1 |
| 64 |  | 3-(8-chloro-3,4-dimethylimidazo[1,5-a]quinoxalin-1-yl)benzamide | 351.1 |
| 65 | 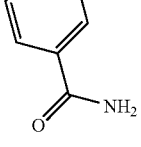 | 8-chloro-3,4-dimethyl-1-(4-methylpyridin-3-yl)imidazo[1,5-a]quinoxaline | 323.1 |

TABLE 5-continued

Examples 62-69

[Structure: 8-chloro-imidazo[1,5-a]quinoxaline core with Me groups and R¹ substituent]

| Example | R¹ | Chemical Name | MS [M + 1]+ |
|---|---|---|---|
| 66 | 3-methylpyridin-4-yl | 8-chloro-3,4-dimethyl-1-(3-methylpyridin-4-yl)imidazo[1,5-a]quinoxaline | 323.1 |
| 67 | 2-chlorophenyl | 8-chloro-1-(2-chlorophenyl)-3,4-dimethylimidazo[1,5-a]quinoxaline | 342 |
| 68 | 2-fluoro-5-carbamoyl-phenyl | 5-(8-chloro-3,4-dimethylimidazo[1,5-a]quinoxalin-1-yl)-2-fluorobenzamide | 369 |
| 69 | 1,3,5-trimethyl-1H-pyrazol-4-yl | 8-chloro-3,4-dimethyl-1-(1,3,5-trimethyl-1H-pyrazol-4-yl)imidazo[1,5-a]quinoxaline | 340.1 |

The symbol " ~ " shows the point where substituent R is attached to the tricyclic ring system.

1-Bromo-6,8-difluoro-3,4-dimethylimidazo[1,5-a]quinoxaline (8A)

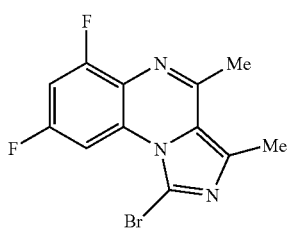

Following the preparation of intermediate 5A, Scheme 1, Example 19, 1,3,5-trifluoro-2-nitrobenzene was converted to 1-bromo-6,8-difluoro-3,4-dimethylimidazo[1,5-a]quinoxaline (8A) as an off-white powder. EIMS 311.9 [M+H]+.

Examples 70-73 were prepared according to the general Suzuki coupling procedure Example 19 using 1-bromo-6,8-difluoro-3,4-dimethylimidazo[1,5-a]quinoxaline (8A). Example 73 6,8-difluoro-1-methoxy-3,4-dimethylimidazo[1,5-a]quinoxaline was obtained from 1-bromo-6,8-difluoro-3,4-dimethylimidazo[1,5-a]quinoxaline (8A) and methanol (stirred for 2 hours at room temperature).

TABLE 6

Examples 70-73

[Structure: 6,8-difluoro-imidazo[1,5-a]quinoxaline core with Me groups and R¹ substituent]

| Example | R¹ | Chemical Name | MS [M + 1]+ |
|---|---|---|---|
| 70 | 2-methylphenyl | 6,8-difluoro-3,4-dimethyl-1-(2-methylphenyl)imidazo[1,5-a]quinoxaline | 324.1 |
| 71 | 4-methylpyridin-3-yl | 6,8-difluoro-3,4-dimethyl-1-(4-methylpyridin-3-yl)imidazo[1,5-a]quinoxaline | 325.1 |
| 72 | 3-methylpyridin-4-yl | 6,8-difluoro-3,4-dimethyl-1-(3-methylpyridin-4-yl)imidazo[1,5-a]quinoxaline | 325.1 |
| 73 | OCH₃ | 6,8-difluoro-1-methoxy-3,4-dimethylimidazo[1,5-a]quinoxaline | 264 |

The symbol " ~ " shows the point where substituent R is attached to the tricyclic ring system.

Examples 74-79 were prepared according to the general Suzuki coupling procedure for Example 19 as shown in Scheme 2, using 1-bromo-6-fluoro-8-methoxy-3,4-dimethylimidazo[1,5-a]quinoxaline (6A) prepared according to WO 03/075921 and Scheme 1, Example 19.

Scheme 2

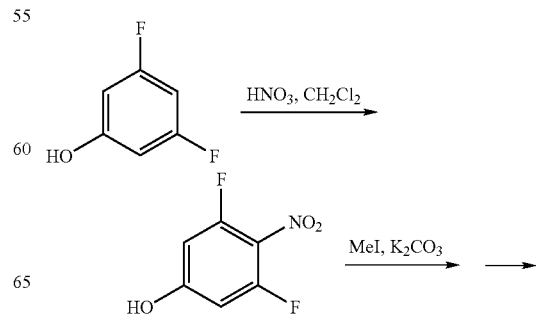

-continued

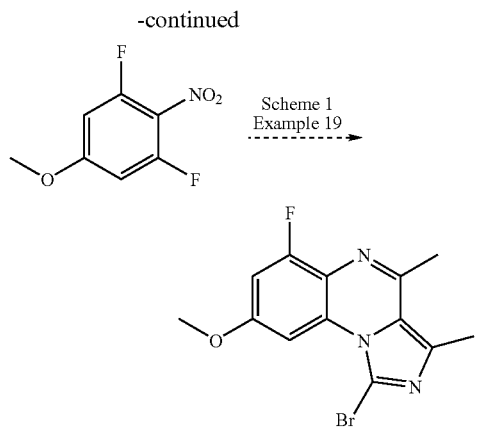

Scheme 1
Example 19

TABLE 7

Examples 74-79

| Example | R¹ | Chemical Name | MS [M + 1]+ |
|---|---|---|---|
| 74 | 3-methylpyridin-4-yl | 6-fluoro-8-methoxy-3,4-dimethyl-1-(3-methylpyridin-4-yl)imidazo[1,5-a]quinoxaline | 337 |
| 75 | 4-methylpyridin-3-yl | 6-fluoro-8-methoxy-3,4-dimethyl-1-(4-methylpyridin-3-yl)imidazo[1,5-a]quinoxaline | 337.1 |
| 76 | 2-methylpyridin-3-yl | 6-fluoro-8-methoxy-3,4-dimethyl-1-(2-methylpyridin-3-yl)imidazo[1,5-a]quinoxaline | 337.1 |
| 77 | 2-chlorophenyl | 1-(2-chlorophenyl)-6-fluoro-8-methoxy-3,4-dimethylimidazo[1,5-a]quinoxaline | 356.1 |
| 78 | 2-fluoro-5-carbamoylphenyl | 2-fluoro-5-(6-fluoro-8-methoxy-3,4-dimethylimidazo[1,5-a]quinoxalin-1-yl)benzamide | 383.1 |
| 79 | 1,3,5-trimethyl-1H-pyrazol-4-yl | 6-fluoro-8-methoxy-3,4-dimethyl-1-(1,3,5-trimethyl-1H-pyrazol-4-yl)imidazo[1,5-a]quinoxaline | 354.1 |

The symbol " ⌇ " shows the point where substituent R is attached to the tricyclic ring system.

Example 76

6-fluoro-8-methoxy-3,4-dimethyl-1-(2-methylpyridin-3-yl)imidazo[1,5-a]quinoxaline ¹H NMR (400 MHz, DMSO) δ ppm 8.72 (m, 1H), 7.94 (m, 1H), 7.48 (m, 1H), 7.02 (dd, 1H), 6.16 (d, 1H), 3.45 (s, 3H), 2.78 (s, 3H), 2.72 (s, 3H), 2.15 (s, 3H).

Example 79

6-fluoro-8-methoxy-3,4-dimethyl-1-(1,3,5-trimethyl-1H-pyrazol-4-yl)imidazo[1,5-a]quinoxaline ¹H NMR (400 MHz, DMSO) δ ppm 7.00 (dd, 1H), 6.80 (d, 1H), 3.78 (s, 3H), 3.56 (s, 3H), 2.75 (s, 3H), 2.68 (s, 3H), 2.05 (s, 3H), 1.88 (s, 3H).

Intermediate 9A: 1-Bromo-8-fluoro-6-methoxy-3,4-dimethylimidazo[1,5-a]quinoxaline

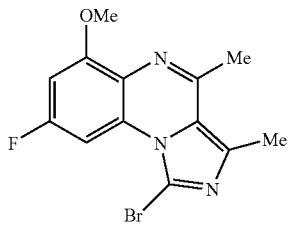

Following the preparation of bromide 5A, Scheme 1, Example 19, 1,5-difluoro-3-methoxy-2-nitrobenzene (see U.S. Patent Application Publication No. 2005176726) was converted to 1-bromo-8-fluoro-6-methoxy-3,4-dimethylimidazo[1,5-a]quinoxaline (9A) as an off-white powder EIMS 324.0 [M+H]+, according to Scheme 3.

Scheme 3

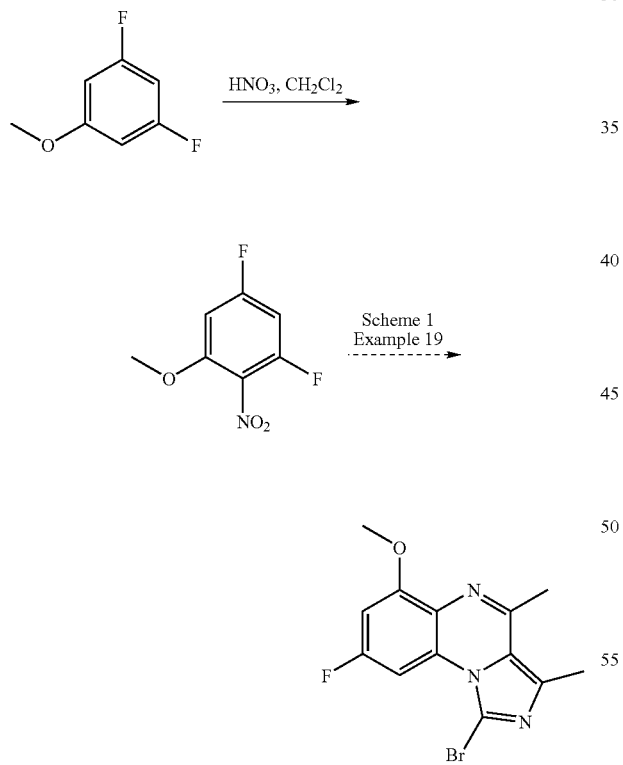

Examples 80-88 were prepared according to the general Suzuki coupling procedure Scheme 1, Example 19, using 1-bromo-8-fluoro-6-methoxy-3,4-dimethylimidazo[1,5-a]quinoxaline (9A).

TABLE 8

Examples 80-88

| Example | R¹ | Chemical Name | MS [M + 1]+ |
|---|---|---|---|
| 80 | 4-methoxypyridin-3-yl | 8-fluoro-6-methoxy-1-(4-methoxypyridin-3-yl)-3,4-dimethylimidazo[1,5-a]quinoxaline | 353.1 |
| 81 | 4-methylpyridin-3-yl | 8-fluoro-6-methoxy-3,4-dimethyl-1-(4-methylpyridin-3-yl)imidazo[1,5-a]quinoxaline | 337.1 |
| 82 | 3-methylpyridin-4-yl | 8-fluoro-6-methoxy-3,4-dimethyl-1-(3-methylpyridin-4-yl)imidazo[1,5-a]quinoxaline | 337.1 |
| 83 | 2-methylpyridin-3-yl | 8-fluoro-6-methoxy-3,4-dimethyl-1-(2-methylpyridin-3-yl)imidazo[1,5-a]quinoxaline | 337.1 |
| 84 | 2-methylphenyl | 8-fluoro-6-methoxy-3,4-dimethyl-1-(2-methylphenyl)imidazo[1,5-a]quinoxaline | 336.1 |
| 85 | 2-chlorophenyl | 1-(2-chlorophenyl)-8-fluoro-6-methoxy-3,4-dimethylimidazo[1,5-a]quinoxaline | 356.1 |
| 86 | 2-fluoro-5-carbamoylphenyl | 2-fluoro-5-(8-fluoro-6-methoxy-3,4-dimethylimidazo[1,5-a]quinoxalin-1-yl)benzamide | 383.1 |

TABLE 8-continued

Examples 80-88

[Structure: tricyclic imidazo[1,5-a]quinoxaline core with OMe, F, Me, Me substituents and R¹ position]

| Example | R¹ | Chemical Name | MS [M + 1]+ |
|---|---|---|---|
| 87 | [2,4-dimethylthiazol-5-yl group] | 1-(2,4-dimethyl-1,3-thiazol-5-yl)-8-fluoro-6-methoxy-3,4-dimethylimidazo[1,5-a]quinoxaline | 357.1 |
| 88 | [1,3,5-trimethylpyrazol-4-yl group] | 8-fluoro-6-methoxy-3,4-dimethyl-1-(1,3,5-trimethyl-1H-pyrazol-4-yl)imidazo[1,5-a]quinoxaline | 354.1 |

The symbol " ⌇ " shows the point where substituent R is attached to the tricyclic ring system.

Compound 8-fluoro-6-methoxy-3,4-dimethyl-1-(3-methylpyridin-4-yl)imidazo[1,5-a]quinoxaline (Example 82) was also prepared to according to Scheme 4.

Scheme 4

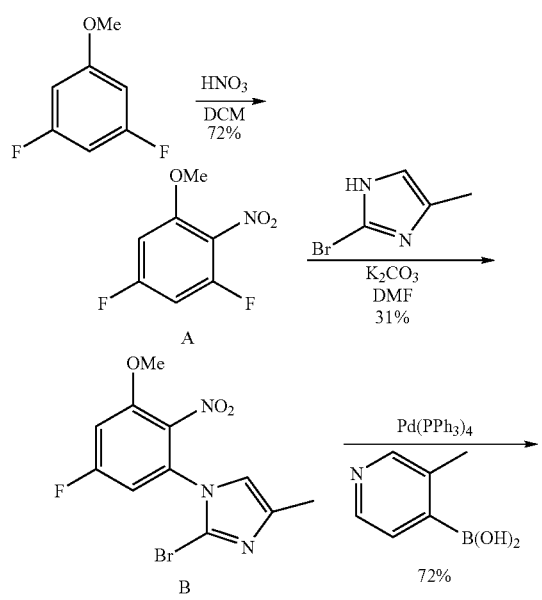

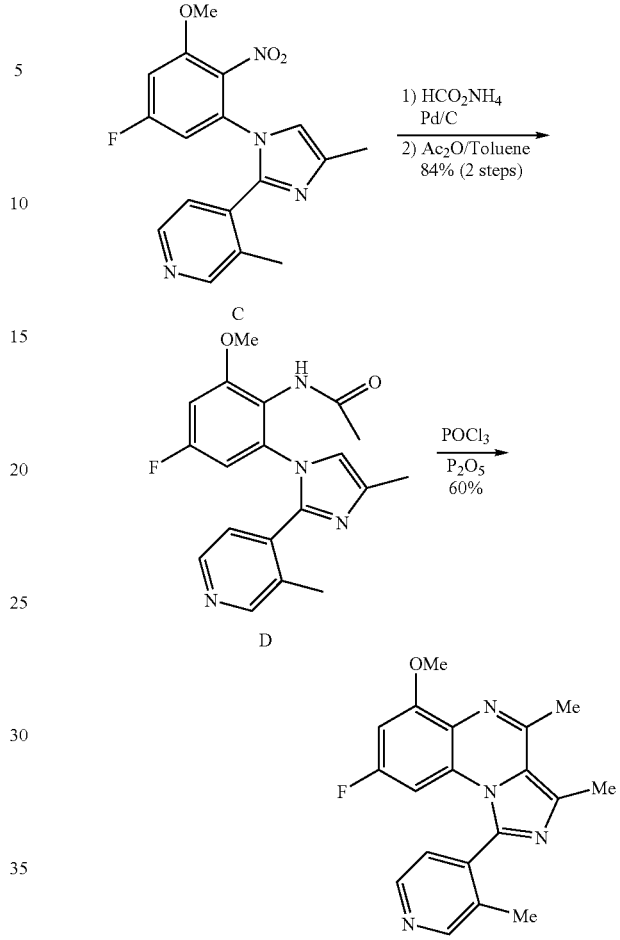

1,5-difluoro-3-methoxy-2-nitrobenzene (A)

To a solution of 3,5-difluoroanisole (30 g, 208 mmol) in 260 mL dichloromethane was added HNO₃ (>90% fuming, 60 mL) dropwise at 0° C. The resulting solution was stirred at 0° C. for 3 hours, then washed water. The aqueous phase was extracted with dichloromethane. The organic phase was washed with brine, dried over magnesium sulfate and condensed on a rotavap. The residue was recrystallized in hexane and ethyl acetate to provide 28.5 g (72% yield) of 1,5-difluoro-3-methoxy-2-nitrobenzene as an off-white powder. $^1$H NMR (400 MHz, DMSO) δ ppm 7.20 (m, 2H), 3.91 (s, 3H).

2-bromo-1-(5-fluoro-3-methoxy-2-nitrophenyl)-4-methyl-1H-imidazole (B)

A mixture of 1,5-difluoro-3-methoxy-2-nitrobenzene (9 g, 47.6 mmol), 2-bromo-4-methylimidazole (7.7 g, 47.6 mmol) and potassium carbonate (14.5 g, 104.7 mmol) in 240 mL DMF was stirred at room temperature overnight. The majority of solvent was removed by rotavap and the residue was diluted with ethyl acetate and washed with water. The aqueous phase was extracted with ethyl acetate and the combined organic phase was washed with water, brined, dried over magnesium sulfate. Condensation and purification using 5-10% ethyl acetate in dichloromethane as eluent provided 4.8 g (31% yield) of 2-bromo-1-(5-fluoro-3-methoxy-2-nitrophenyl)-4-methyl-1H-imidazole as a yellow solid. $^1$H NMR (400 MHz, DMSO) δ ppm 7.60 (dd, 1H), 7.38 (dd, 1H), 7.21 (s, 1H), 3.98 (s, 3H), 2.09 (s, 3H). EIMS 330.0 [M+H]+.

4-(1-(5-fluoro-3-methoxy-2-nitrophenyl)-4-methyl-1H-imidazol-2-yl)-3-methylpyridine (C)

A mixture of bromide intermediate 2-bromo-1-(5-fluoro-3-methoxy-2-nitrophenyl)-4-methyl-1H-imidazole (2.45 g, 7.4 mmol), 3-picoline-4-boronic acid (1.52 g, 11.1 mmol), $K_2CO_3$ (3.06 g, 22.2 mmol) and Pd(PPh$_3$)$_4$ (420 mg, 0.37 mmol) in a 250 mL flask was vacuumed and flushed with nitrogen, followed by the addition of p-dioxane (120 mL) and water (40 mL). The final mixture was stirred at 90° C. for 8 hours, then cooled to room temperature. The reaction was quenched with NH$_4$Cl solution, extracted with ethyl acetate. Combined organic layer was washed with brine then dried over magnesium sulfate. Column chromatography using 50% ethyl acetate in dichloromethane followed by 4-8% MeOH in dichloromethane as eluents provided 1.83 g (72% yield) of 4-(1-(5-fluoro-3-methoxy-2-nitrophenyl)-4-methyl-1H-imidazol-2-yl)-3-methylpyridine as a yellow solid. $^1$H NMR (400 MHz, DMSO) δ ppm 8.49 (s, 1H), 8.26 (d, 1H), 7.44 (dd, 1H), 7.23 (dd, 1H), 7.21 (s, 1H), 6.94 (d, 1H), 3.89 (s, 3H), 2.31 (s, 3H), 2.18 (s, 3H). EIMS 343.1 [M+H]+.

N-(4-fluoro-2-methoxy-6-(4-methyl-2-(3-methylpyridin-4-yl)-1H-imidazol-1-yl)phenyl)acetamide (D)

Step 1: To a mixture of 4-(1-(5-fluoro-3-methoxy-2-nitrophenyl)-4-methyl-1H-imidazol-2-yl)-3-methylpyridine (1.83 g, 5.3 mmol) and 10% Pd/C (300 mg, 0.265 mmol) was added 30 mL THF, followed by addition of 30 mL MeOH under nitrogen atmosphere. HCO$_2$NH$_4$ (2.0 g, 29.15 mmol) was added to the mixture and the final mixture was stirred at 50° C. for 2 hours. The reaction was filtered through celite pad and the solvent was removed under vacuum. TLC indicated reaction was incompleted and the residue was subjected to the same condition and stirred at 50° C. for another 4 hours. Now the reaction was completed and clean based on TLC. The same workup as above provided an offwhite solid which was used as is.

Step 2: To the crude material from step 1 was added 45 mL toluene, followed by addition of 5 mL Ac$_2$O (53 mmol). The resulting mixture was stirred at 80° C. for 4 hours and cooled to room temperature. The reaction was quenched with sodium bicarbonate solution and extracted with dichloromethane (3×). Condensation and column purification using 3-8% methanol in dichloromethane as eluent provided 1.58 g (84% yield over 2 steps) of N-(4-fluoro-2-methoxy-6-(4-methyl-2-(3-methylpyridin-4-yl)-1H-imidazol-1-yl)phenyl)acetamide as an off-white foam. $^1$H NMR (400 MHz, DMSO) δ ppm 9.06 (s, 1H), 8.44 (s, 1H), 8.15 (d, 1H), 7.05-6.95 (m, 3H), 6.38 (dd, 1H), 3.78 (s, 3H), 2.35 (s, 3H), 2.15 (s, 3H), 1.82 (s, 3H). EIMS 355.1 [M+H]+.

Example 82

8-Fluoro-6-methoxy-3,4-dimethyl-1-(3-methylpyridin-4-yl)imidazo[1,5-a]quinoxaline To a mixture of intermediate N-(4-fluoro-2-methoxy-6-(4-methyl-2-(3-methylpyridin-4-yl)-1H-imidazol-1-yl)phenyl)acetamide (1.58 g, 4.46 mmol) and P$_2$O$_5$ (3.16 g, 22.3 mmol) was added 60 mL of POCl$_3$ under nitrogen. The resulting mixture was stirred at 120° C. for 6 hours and cooled to room temperature. Majority of solvent was removed under vacuum and the residue was diluted with ethyl acetate. The mixture was transferred very carefully into iced-50% NaOH solution. The mixture was stirred for 10 minutes (make sure pH>7) and extracted with ethyl acetate (3×). Condensation and column purification using 4-8% MeOH in dichloromethane as eluent provided 880 mg (60% yield) of 8-fluoro-6-methoxy-3,4-dimethyl-1-(3-methylpyridin-4-yl)imidazo[1,5-a]quinoxaline as an offwhite powder. $^1$H NMR (400 MHz, DMSO) δ ppm 8.68 (s, 1H), 8.60 (d, 1H), 7.48 (d, 1H), 7.00 (dd, 1H), 6.16 (dd, 1H), 3.88 (s, 3H), 2.75 (s, 3H), 2.69 (s, 3H), 1.98 (s, 3H). EIMS 337.1 [M+H]+.

Example 83

8-Fluoro-6-methoxy-3,4-dimethyl-1-(2-methylpyridin-3-yl)imidazo[1,5-a]quinoxaline $^1$H NMR (400 MHz, DMSO) δ ppm 8.72 (m, 1H), 7.92 (m, 1H), 7.46 (m, 1H), 7.02 (dd, 1H), 6.08 (dd, 1H), 3.91 (s, 3H), 2.77 (s, 3H), 2.72 (s, 3H), 2.14 (s, 3H).

Example 84

8-Fluoro-6-methoxy-3,4-dimethyl-1-o-tolylimidazo[1,5-a]quinoxaline $^1$H NMR (400 MHz, DMSO) δ ppm 7.58 (m, 1H), 7.48 (m, 1H), 7.41 (m, 2H), 6.96 (dd, 1H), 6.12 (dd, 1H), 3.89 (s, 3H), 2.76 (s, 3H), 2.71 (s, 3H), 1.93 (s, 3H).

Example 85

1-(2-Chlorophenyl)-8-fluoro-6-methoxy-3,4-dimethylimidazo[1,5-a]quinoxaline $^1$H NMR (400 MHz, DMSO) δ ppm 7.68 (m, 3H), 7.59 (m, 1H), 6.96 (dd, 1H), 6.10 (dd, 1H), 3.88 (s, 3H), 2.75 (s, 3H), 2.69 (s, 3H).

Example 87

5-(8-Fluoro-6-methoxy-3,4-dimethylimidazo[1,5-a]quinoxalin-1-yl)-2,4-dimethylthiazole $^1$H NMR (400 MHz, DMSO) δ ppm 7.02 (dd, 1H), 6.58 (dd, 1H), 3.92 (s, 3H), 2.75 (s, 3H), 2.74 (s, 3H), 2.70 (s, 3H), 2.04 (s, 3H).

Example 88

8-fluoro-6-methoxy-3,4-dimethyl-1-(1,3,5-trimethyl-1H-pyrazol-4-yl)imidazo[1,5-a]quinoxaline $^1$H NMR (400 MHz, DMSO) δ ppm 6.98 (dd, 1H), 6.80 (dd, 1H), 3.92 (s, 3H), 3.78 (s, 3H), 2.75 (s, 3H), 2.68 (s, 3H), 2.08 (s, 3H), 1.86 (s, 3H).

Examples 89-93 were prepared according to scheme 5 using the corresponding bromide or iodide as alkylating agents.

Example 93, 6-(difluoromethoxy)-8-fluoro-3,4-dimethyl-1-(2-methylphenyl)imidazo[1,5-a]quinoxaline, was prepared using sodium chlorodifluoroacetate as an alkylating agent.

Scheme 5

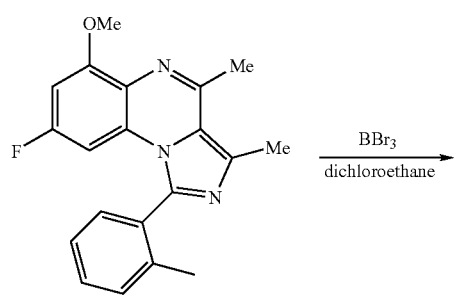

BBr₃
dichloroethane
→

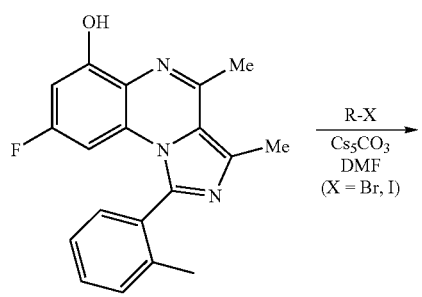

R-X
Cs₅CO₃
DMF
(X = Br, I)
→

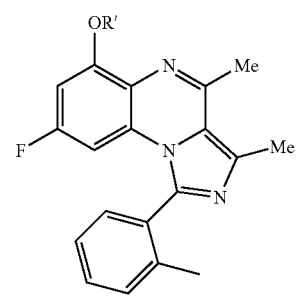

TABLE 9

Examples 89-93

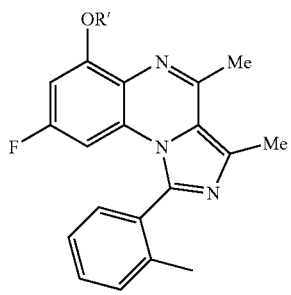

| Example | R' | Chemical Name | MS [M + 1]+ |
|---|---|---|---|
| 89 | H | 8-fluoro-3,4-dimethyl-1-(2-methylphenyl)imidazo[1,5-a]quinoxalin-6-ol | 322.1 |
| 90 | ⌇⟨cyclopropylmethyl⟩ | 6-(cyclopropylmethoxy)-8-fluoro-3,4-dimethyl-1-(2-methylphenyl)imidazo[1,5-a]quinoxaline | 376.1 |
| 91 | CF₃CH₂ | 8-fluoro-3,4-dimethyl-1-(2-methylphenyl)-6-(2,2,2-trifluoroethoxy)imidazo[1,5-a]quinoxaline | 404.1 |

TABLE 9-continued

Examples 89-93

| Example | R' | Chemical Name | MS [M + 1]+ |
|---|---|---|---|
| 92 | CH₃CH₂ | 6-ethoxy-8-fluoro-3,4-dimethyl-1-(2-methylphenyl)imidazo[1,5-a]quinoxaline | 350.1 |
| 93 | CHF₂ | 6-(difluoromethoxy)-8-fluoro-3,4-dimethyl-1-(2-methylphenyl)imidazo[1,5-a]quinoxaline | 372.1 |

The symbol " ⌇ " shows the point where substituent R is attached to the tricyclic ring system.

Examples 94-96 were prepared according to Scheme 6.

Scheme 6

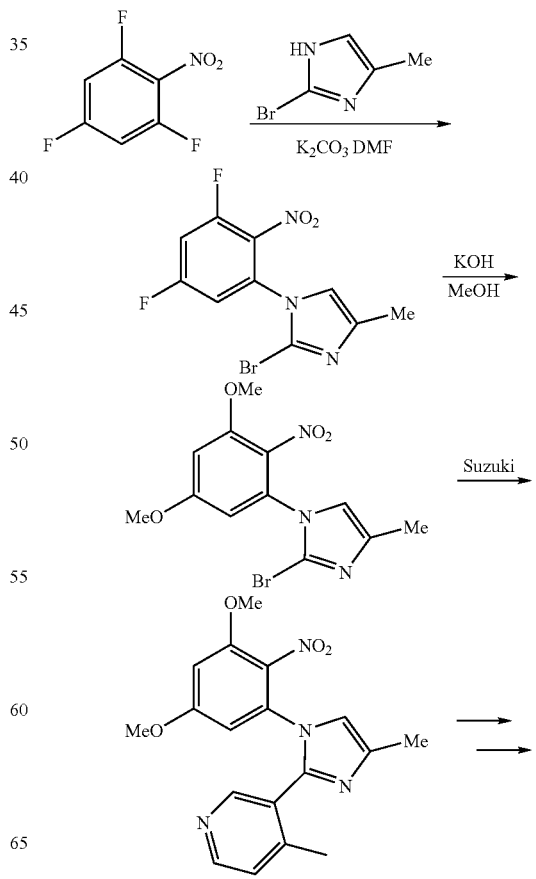

-continued

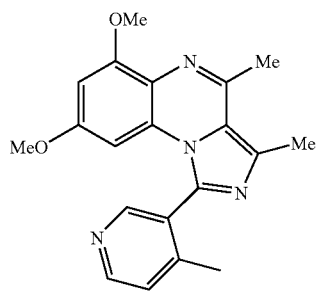

2-Bromo-1-(3,5-difluoro-2-nitrophenyl)-4-methyl-1H-imidazole

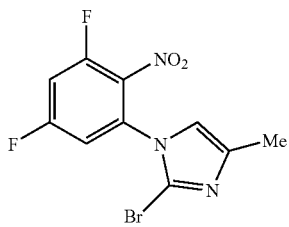

A mixture of 1,3,5-trifluoro-2-nitrobenzene (2.2 mL, 18.6 mmol), 2-bromo-4-methylimidazole (3 g, 18.6 mmol) and $K_2CO_3$ (5.66 g, 41 mmol) in 80 mL DMF was stirred at room temperature overnight. The mixture was diluted with ethyl acetate and washed with water. Standard work up procedure followed by column purification using 10% ethyl acetate in dichloromethane as eluent provided 3.18 g (54% yield) of the product as a yellow powder. EIMS 317.9 [M+H]+.

2-Bromo-1-(3,5-dimethoxy-2-nitrophenyl)-4-methyl-1H-imidazole

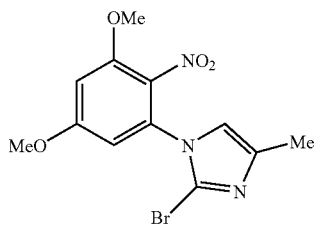

To a solution of 2-bromo-1-(3,5-difluoro-2-nitrophenyl)-4-methyl-1H-imidazole (2.98 g, 9.4 mmol) in 40 mL MeOH was added freshly powdered KOH (2.5 g, 44.6 mmol) at room temperature under nitrogen. The resulting mixture was stirred at 55° C. for 2 hours, cooled to room temperature, diluted with dichloromethane and poured into water. Standard work up and condensation on rotavap provided 3.35 g (100% yield) of the product as an offwhite solid. EIMS 342.0 [M+H]+.

3-(1-(3,5-Dimethoxy-2-nitrophenyl)-4-methyl-1H-imidazol-2-yl)-4-methylpyridine

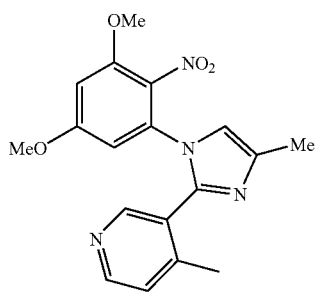

Following the general Suzuki coupling procedure, reaction of 2-bromo-1-(3,5-dimethoxy-2-nitrophenyl)-4-methyl-1H-imidazole (1.1 g, 3.2 mmol), 4-methyl-3-pyridylboronic acid (876 mg, 6.4 mmol), $K_2CO_3$ (1.32 g, 9.6 mmol) and $Pd(PPh_3)_4$ (186 mg, 0.161 mmol) provided 788 mg (69% yield) of the desired product as an off white powder. EIMS 355.1 [M+H]+.

3-(1-(3,5-Dimethoxy-2-nitrophenyl)-4-methyl-1H-imidazol-2-yl)-4-methylpyridine was converted to compound 6,8-dimethoxy-3,4-dimethyl-1-(4-methylpyridin-3-yl)imidazo[1,5-a]quinoxaline (Example 94) in a similar manner to the synthesis of Compound 8-fluoro-6-methoxy-3,4-dimethyl-1-(3-methylpyridin-4-yl)imidazo[1,5-a]quinoxaline (Example 82) from intermediate C.

TABLE 10

Examples 94-96

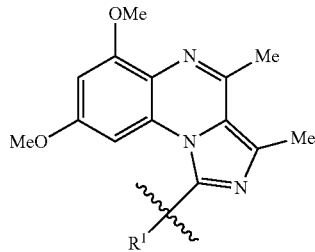

| Example | R¹ | Chemical Name | MS [M + 1]+ |
|---|---|---|---|
| 94 | 4-methylpyridin-3-yl | 6,8-dimethoxy-3,4-dimethyl-1-(4-methylpyridin-3-yl)imidazo[1,5-a]quinoxaline | 349.1 |
| 95 | 3-methylpyridin-4-yl | 6,8-dimethoxy-3,4-dimethyl-1-(3-methylpyridin-4-yl)imidazo[1,5-a]quinoxaline | 349.1 |
| 96 | 2-methylpyridin-3-yl | 6,8-dimethoxy-3,4-dimethyl-1-(2-methylpyridin-3-yl)imidazo[1,5-a]quinoxaline | 349.1 |

The symbol " ⌇ " shows the point where substituent R is attached to the tricyclic ring system.

Example 94

6,8-dimethoxy-3,4-dimethyl-1-(4-methylpyridin-3-yl)imidazo[1,5-a]quinoxaline $^1$H NMR (400 MHz, DMSO) δ ppm 8.66 (d, 1H), 8.60 (s, 1H), 7.51 (d, 1H), 6.60 (d, 1H), 6.00 (d, 1H), 3.87 (s, 3H), 3.36 (s, 3H), 2.74 (s, 3H), 2.71 (s, 3H), 2.01 (s, 3H).

Example 95

6,8-dimethoxy-3,4-dimethyl-1-(3-methylpyridin-4-yl)imidazo[1,5-a]quinoxaline $^1$H NMR (400 MHz, DMSO) δ ppm 8.69 (s, 1H), 8.61 (d, 1H), 7.50 (d, 1H), 6.62 (d, 1H), 6.01 (d, 1H), 3.88 (s, 3H), 3.34 (s, 3H), 2.75 (s, 3H), 2.71 (s, 3H), 1.99 (s, 3H).

Example 97

4-(6-methoxy-3,4-dimethyl-1-(3-methylpyridin-4-yl)imidazo[1,5-a]quinoxalin-8-yl)morpholine

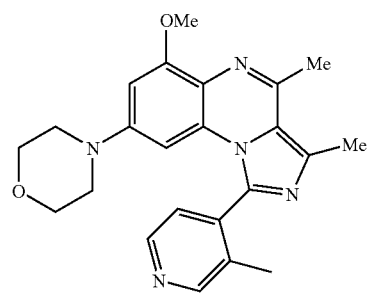

Following the synthetic sequence for the synthesis of Example 94, 4-(3,5-difluoro-4-nitrophenyl)morpholine (see: WO 2005/087754) was converted to Example 97 as a light yellow powder. EIMS 404.2 [M+H]+.

Example 98

4-(6-methoxy-3,4-dimethyl-1-(2-methylpyridin-3-yl)imidazo[1,5-a]quinoxalin-8-yl)morpholine

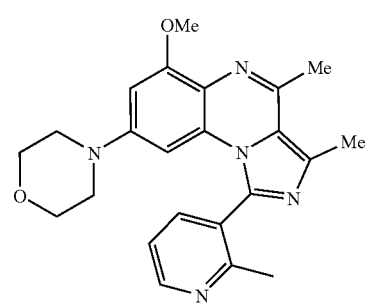

Following the synthetic sequence for the synthesis of Example 94, 4-(3,5-difluoro-4-nitrophenyl)morpholine (see: WO 2005087754) was converted to Example 98 as a light yellow powder. EIMS 404.2 [M+H]+.

Example 99

3,4-dimethyl-1-(3-methyl-2-thienyl)imidazo[1,5-a]quinoxaline

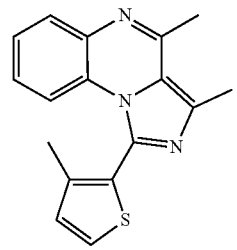

Compound was made according to Example 37. A white solid was recovered (0.007 g) 6% yield. MS (ES) m/z 294.1 [M+1]$^+$

Example 100

1-(3,5-dimethylisoxazol-4-yl)-3,4-dimethylimidazo[1,5-a]quinoxaline

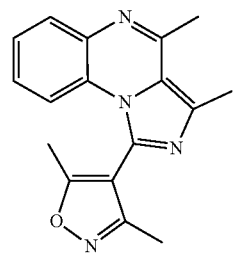

Compound was made according to Example 37. A white solid was recovered (0.01 g) 8% yield. MS (ES) m/z 293.1 [M+1]$^+$

Example 101

3-(3,4-dimethylimidazo[1,5-a]quinoxalin-1-yl)benzamide

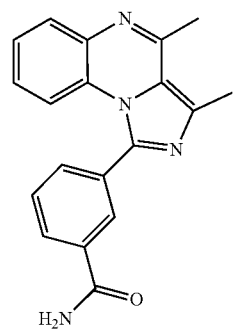

Compound was made according to Example 37. A white solid was recovered (0.07 g) 56% yield. MS (ES) m/z 317.1 [M+1]$^+$

Example 102

3-(3,4-dimethylimidazo[1,5-a]quinoxalin-1-yl)-4-fluorobenzamide

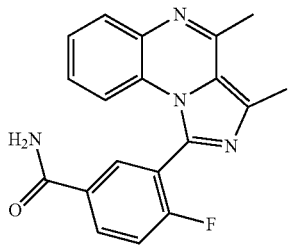

Compound was made according to Example 37. A white solid was recovered (0.016 g) 12% yield. MS (ES) m/z 335.1 [M+1]+

Example 103

1-(6-fluoro-2-methylpyridin-3-yl)-3,4-dimethylimidazo[1,5-a]quinoxaline

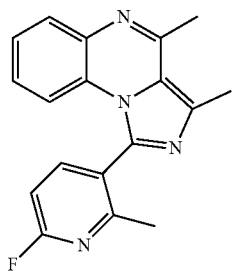

Compound was made according to Example 37. A white solid was recovered (0.04 g) 33% yield. MS (ES) m/z 307.1 [M+1]+

Example 104

3,4-dimethyl-1-(4-methylpyridin-3-yl)imidazo[1,5-a]quinoxaline

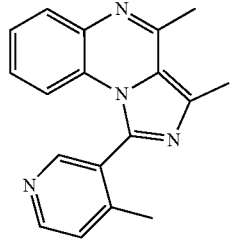

Compound was made according to Example 37. A white solid was recovered (0.06 g) 53% yield. MS (ES) m/z 289.2 [M+1]+

Examples 105-115 were made according to the procedure given in scheme 1 using 2-fluoro-4-methoxy-nitrobenzene and the appropriate boronic acid or pinnacle boronate.

TABLE 11

Examples 105-115

| Example | R¹ | Name | MS (ES) m/z [M + 1]+ |
|---|---|---|---|
| 105 | 2-chloro-4-fluorophenyl | 1-(2-chloro-4-fluorophenyl)-8-methoxy-3,4-dimethylimidazo[1,5-a]quinoxaline | 356.1 |
| 106 | 4-chloro-2-(trifluoromethyl)phenyl | 1-[4-chloro-2-(trifluoromethyl)phenyl]-8-methoxy-3,4-dimethylimidazo[1,5-a]quinoxaline | 406.0 |
| 107 | 5-chloro-2-methylphenyl | 1-(5-chloro-2-methylphenyl)-8-methoxy-3,4-dimethylimidazo[1,5-a]quinoxaline | 352.1 |
| 108 | 4-fluoro-2-methylphenyl | 1-(4-fluoro-2-methylphenyl)-8-methoxy-3,4-dimethylimidazo[1,5-a]quinoxaline | 336.1 |
| 109 | 3-fluoro-2-methylphenyl | 1-(3-fluoro-2-methylphenyl)-8-methoxy-3,4-dimethylimidazo[1,5-a]quinoxaline | 336.1 |
| 110 | 4-methoxypyridin-3-yl | 8-methoxy-1-(4-methoxypyridin-3-yl)-3,4-dimethylimidazo[1,5-a]quinoxaline | 335.1 |
| 111 | 4-methylpyridin-3-yl | 8-methoxy-3,4-dimethyl-1-(4-methylpyridin-3-yl)imidazo[1,5-a]quinoxaline | 319.1 |
| 112 | 3-carbamoylphenyl | 3-(8-methoxy-3,4-dimethylimidazo[1,5-a]quinoxalin-1-yl)benzamide | 347.1 |
| 113 | 6-fluoro-2-methylpyridin-3-yl | 1-(6-fluoro-2-methylpyridin-3-yl)-8-methoxy-3,4-dimethylimidazo[1,5-a]quinoxaline | 337.1 |
| 114 | 4-fluoro-3-carbamoylphenyl | 4-fluoro-3-(8-methoxy-3,4-dimethylimidazo[1,5-a]quinoxalin-1-yl)benzamide | 365.1 |

TABLE 11-continued

Examples 105-115

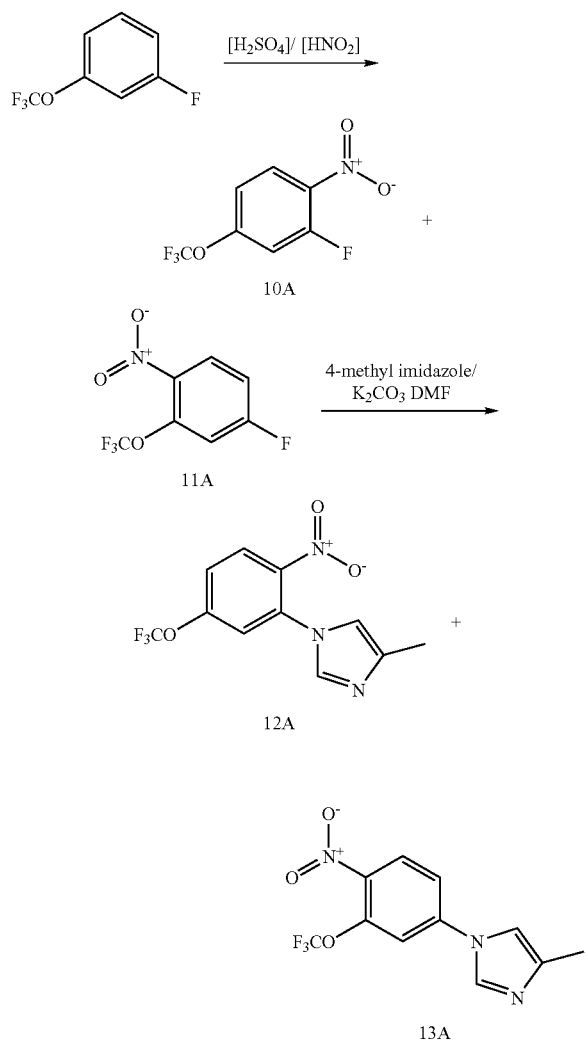

| Example | R¹ | Name | MS (ES) m/z [M + 1]⁺ |
|---|---|---|---|
| 115 | (2-methylphenyl) * | 8-methoxy-3,4-dimethyl-1-(2-methylphenyl)imidazo[1,5-a]quinoxaline | 318.1 |

The symbol "*" shows the point where substituent R is attached to the tricyclic ring system.

Method A

Scheme 7 shows a synthetic method that was used in the preparation of Intermediates 10A, 11A, 12A, and 13A.

Step 1. Intermediates 10A and 11A 10A) 2-Fluoro-1-nitro-4-trifluoromethoxy-benzene 11A) 4-Fluoro-1-nitro-2-trifluoromethoxy-benzene To 1-fluoro-3-trifluoromethoxybenzene (1 mL) was added concentrated sulfuric acid (1 mL) at 0° C. To the cold solution was added dropwise (0.7 mL) of a solution made from concentrated nitric acid (1 mL) and concentrated sulfuric acid (1 mL). The reaction was slowly allowed to warm to room temperature then poured onto ice and extracted with ether. The organic layer was separated and washed with sodium hydroxide 1N, then brined and dried over magnesium sulfate. The solvent was removed under reduce pressure at room temperature. A pale yellow oil (1 g) was recovered and used without further purification.

Step 2. Intermediates 12A and 13A 12A) 4-Methyl-1-(2-nitro-5-trifluoromethoxy-phenyl)-1H-imidazole 13A) 4-Methyl-1-(4-nitro-3-trifluoromethoxy-phenyl)-1H-imidazole The crude product from step 1, Method A, (1 g, 4.4 mmol) was dissolved in DMF (8 mL). To this was added 4-methyl imidazole (0.36 g, 0.44 mmol) followed by potassium carbonate (1.2 g, 0.88 mmol). The reaction was let stir at room temperature for 16 hrs then poured into water and extracted with ethyl acetate. The organic layer was separated and washed with water then brined, dried over magnesium sulfate and filtered. The solvent was removed under reduced pressure and the cruder purified by flash chromatography on silica gel in ethyl acetate. A yellow solid (0.3 g) was recovered as intermediate 12A, Method A. MS (ES) m/z 288.0 [M+1]⁺

Examples 116-120 were made according to the procedure given in scheme 1 (Example 19) using 4-methyl-1-(2-nitro-5-trifluoromethoxy-phenyl)-1H-imidazole (intermediate 12A, method A) and the appropriate boronic acid or pinnacle boronate.

TABLE 12

Examples 116-120

| Example | R | Name | MS (ES) m/z [M + 1]⁺ |
|---|---|---|---|
| 116 | 4-methylpyridin-3-yl * | 3,4-dimethyl-1-(4-methylpyridin-3-yl)-8-(trifluoromethoxy)imidazo[1,5-a]quinoxaline | 373.1 |
| 117 | 6-fluoro-2-methylpyridin-3-yl * | 1-(6-fluoro-2-methylpyridin-3-yl)-3,4-dimethyl-8-(trifluoromethoxy)imidazo[1,5-a]quinoxaline | 391.1 |

TABLE 12-continued

Examples 116-120

| Example | R | Name | MS (ES) m/z [M + 1]+ |
|---|---|---|---|
| 118 | (2-methylphenyl)* | 3,4-dimethyl-1-(2-methylphenyl)-8-(trifluoromethoxy)imidazo[1,5-a]quinoxaline | 372.1 |
| 119 | (3-methylpyridin-4-yl)* | 3,4-dimethyl-1-(3-methylpyridin-4-yl)-8-(trifluoromethoxy)imidazo[1,5-a]quinoxaline | 373.1 |
| 120 | H₂NOC-phenyl* | 3-[3,4-dimethyl-8-(trifluoromethoxy)imidazo[1,5-a]quinoxalin-1-yl]benzamide | 401.1 |

The symbol "*" shows the point where substituent R is attached to the tricyclic ring system.

Method B

Intermediate 14A

2-Methyl-3-(4,4,5,5-tetramethyl-[1,3,2]dioxaborolan-2-yl)-pyridine

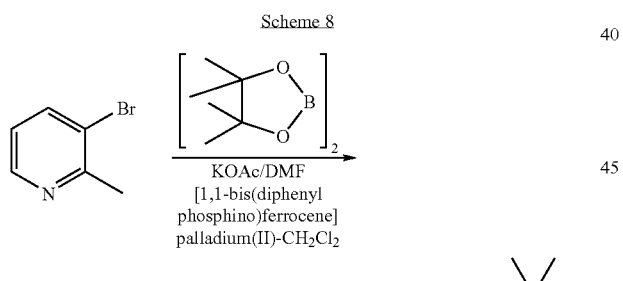

Scheme 8

3-Bromo-2-pinnacol (1 g, 5.8 mmol) was dissolved in DMF (20 mL). To this was added potassium acetate (2 g, 20.3 mmol) followed by 4,4,5,5,4',4',5',5'-Octamethyl-[2,2']bi[[1,3,2]dioxaborolanyl] (1.9 g, 7.5 mmol) and [1,1-bis(diphenylphosphino)ferrocene]palladium(II)bis methylene chloride (0.47 g, 10% mol). The reaction was heated to 80° C. for 16 hrs then poured into water and extracted with ethyl acetate. The organic layer was separated and brined then dried over magnesium Examples 121-125 were made according to the procedure given in scheme 1 (Example 19) using 2-fluoro-4-trifluoromethyl nitrobenzene and the appropriate boronic acid or pinnacle boronate (method B, intermediate 14A).

TABLE 13

Examples 121-125

| Example | R | Name | MS (ES) m/z [M + 1]+ |
|---|---|---|---|
| 121 | (4-methylpyridin-3-yl)* | 3,4-dimethyl-1-(4-methylpyridin-3-yl)-8-(trifluoromethyl)imidazo[1,5-a]quinoxaline | 357.1 |
| 122 | (3-methylpyridin-4-yl)* | 3,4-dimethyl-1-(3-methylpyridin-4-yl)-8-(trifluoromethyl)imidazo[1,5-a]quinoxaline | 357.1 |
| 123 | (4-methoxypyridin-3-yl)*, OMe | 1-(4-methoxypyridin-3-yl)-3,4-dimethyl-8-(trifluoromethyl)imidazo[1,5-a]quinoxaline | 373.1 |
| 124 | (2-methylpyridin-3-yl)* | 3,4-dimethyl-1-(2-methylpyridin-3-yl)-8-(trifluoromethyl)imidazo[1,5-a]quinoxaline | 357.1 |
| 125 | (2-methylphenyl)* | 3,4-dimethyl-1-(2-methylphenyl)-8-(trifluoromethyl)imidazo[1,5-a]quinoxaline | 356.1 |

The symbol "*" shows the point where substituent R is attached to the tricyclic ring system.

Method C

Scheme 9 shows a synthetic method that was used in the preparation of Intermediate 2C.

Intermediate 1C:
1-Chloro-5-fluoro-2-methoxy-4-nitro-benzene

Scheme 9

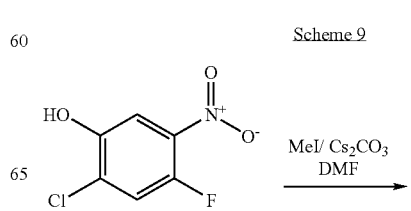

MeI/ Cs₂CO₃
DMF

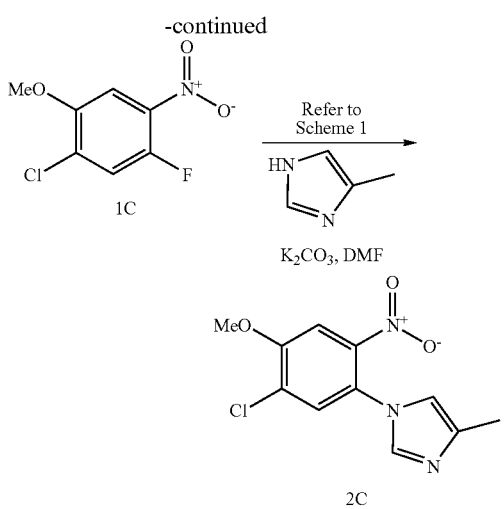

1-chloro-5-fluoro-2-hydroxy-nitro-benzene (0.5 g, 2.6 mmol) was dissolved in DMF (5 mL). To this was added methyl iodide (0.4 mL, 5.2 mmol) followed by cesium carbonate (1.2 g, 3.9 mmol). The reaction was let stir for 2 hrs at room temperature then poured into water and extracted with ethyl acetate. The organic layer was separated then washed with dilute sodium carbonate solution, water, brined and dried over magnesium sulfate then filtered. The solvent removed under reduced pressure. A pale yellow solid (0.43 g) was recovered without further purification MS (ES) m/z 205.0 [M+1]$^+$ Intermediate 3C: 4-Chloro-5-methoxy-2-(4-methyl-imidazol-1-yl)-phenylamine

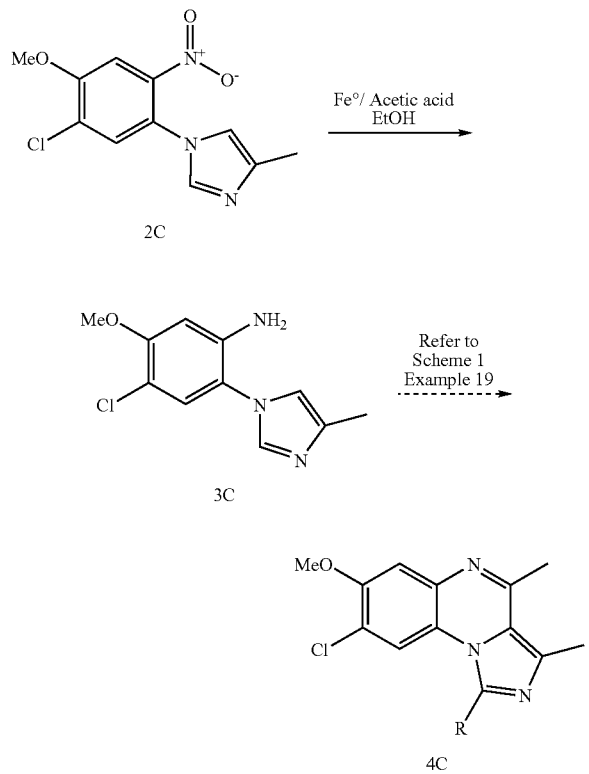

1-(5-Chloro-4-methoxy-2-nitro-phenyl)-4-methyl-1H-imidazole (1.0 g, 3.7 mmol) (intermediate 2C, method C) was dissolved in a solution containing ethanol and acetic acid (5 mL) each. To this was added iron powder (1.25 g, 18.5 mmol). The reaction was heated to 100° C. for 1 hr then filtered thru celite and washed with ethyl acetate. The organic layer was then washed with water, dilute potassium carbonate solution, brined and dried over magnesium sulfate. The extract was then filtered and the solvent removed under reduced pressure. A white solid (0.78 g) was recovered without further purification MS (ES) m/z 238.1 [M+1]$^+$ Examples 126-131 were made according to the procedure given in method C using 1-chloro-5-fluoro-2-methoxy-4-nitro-benzene (intermediate 1C, method C) and the appropriate boronic acid or pinnacle boronate (method B, intermediate 14A).

TABLE 14

Examples 126-131

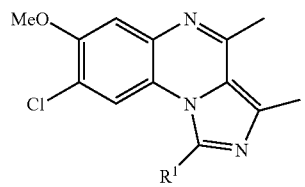

| Example | R¹ | Chemical Name | MS (ES) m/z [M + 1]$^+$ |
|---|---|---|---|
| 126 | (2-methylphenyl)* | 8-chloro-7-methoxy-3,4-dimethyl-1-(2-methylphenyl)imidazo[1,5-a]quinoxaline | 352.1 |
| 127 | (3-methylpyridin-4-yl)* | 8-chloro-7-methoxy-3,4-dimethyl-1-(3-methylpyridin-4-yl)imidazo[1,5-a]quinoxaline | 353.0 |
| 128 | (4-methylpyridin-3-yl)* | 8-chloro-7-methoxy-3,4-dimethyl-1-(4-methylpyridin-3-yl)imidazo[1,5-a]quinoxaline | 353.0 |
| 129 | (2-chlorophenyl)* | 8-chloro-1-(2-chlorophenyl)-7-methoxy-3,4-dimethylimidazo[1,5-a]quinoxaline | 372.1 |
| 130 | (2-methylpyridin-3-yl)* | 8-chloro-7-methoxy-3,4-dimethyl-1-(2-methylpyridin-3-yl)imidazo[1,5-a]quinoxaline | 353.1 |
| 131 | (1,3,5-trimethyl-1H-pyrazol-4-yl)* | 8-chloro-7-methoxy-3,4-dimethyl-1-(1,3,5-trimethyl-1H-pyrazol-4-yl)imidazo[1,5-a]quinoxaline | 370.1 |

The symbol "*" shows the point where substituent R is attached to the tricyclic ring system.

Example 132

8-Chloro-7-ethoxy-3,4-dimethyl-1-(2-methylphenyl)imidazo[1,5-a]quinoxaline

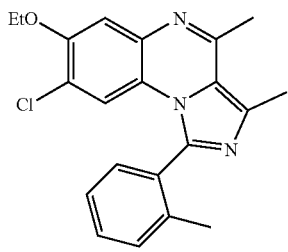

Method F

Scheme 11 shows a synthetic method that was used in the preparation of compounds of Example 132.

Scheme 11

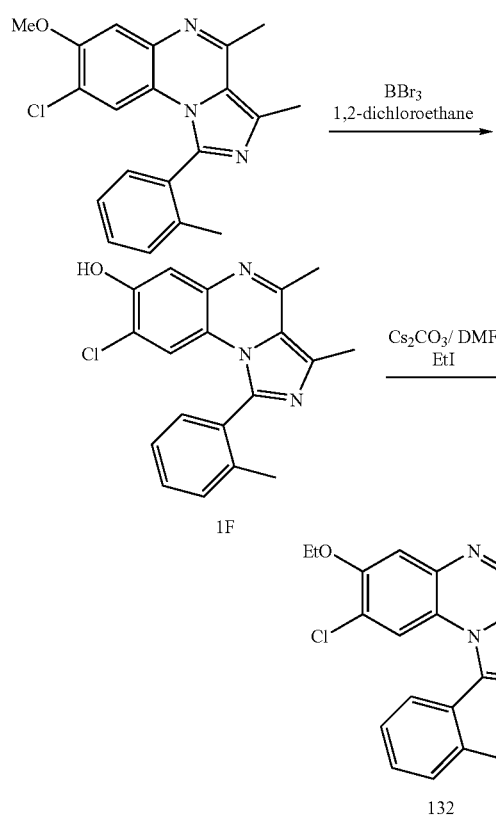

Intermediate 1F: 8-Chloro-3,4-dimethyl-1-o-tolyl-imidazo[1,5-a]quinoxalin-7-ol

Example 27 (0.39 g, 1.1 mmol) was suspended in a dichloroethane (5 mL). To this was then added boron tribromide (1.0 mL), 10 mmol). The reaction was heated to 60° C. for 1 hr. poured into water, neutralized with solid sodium bicarbonate and extracted with ethyl acetate. The organic layer was separated then brined, dried over magnesium sulfate and filtered. The solvent was removed under reduced pressure and the crude purified by flash chromatography on silica gel in ethyl acetate. A yellow solid (0.03 g) was recovered. MS (ES) m/z 338.0 [M+1]$^+$

Example 132

Intermediate 1F, method F (0.03 g, 0.08 mmol) was dissolved in DMF (5 mL). To this was added ethyl iodide (0.1 mL, 0.9 mmol) followed by cesium carbonate (0.06 g, 0.16 mmol). The reaction was let stir for 16 hrs at room temperature then poured into water and extracted with ethyl acetate. The organic layer was separated then washed with water, brined and dried over magnesium sulfate and filtered. The solvent was removed under reduced pressure. Crude purified by flash chromatography on silica gel in 1:1 hexane/ethyl acetate. A pale yellow solid (0.015 g) was recovered without further purification MS (ES) m/z 366.1 [M+1]$^+$

Example 133

6-Methoxy-3,4-dimethyl-1-(2-methylphenyl)imidazo[1,5-a]quinoxaline

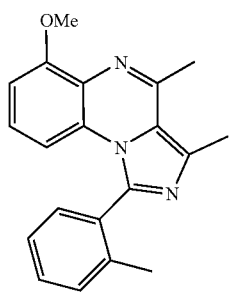

Method D

Scheme 12 shows a synthetic method that was used in the preparation of compounds of Example 133.

Scheme 12

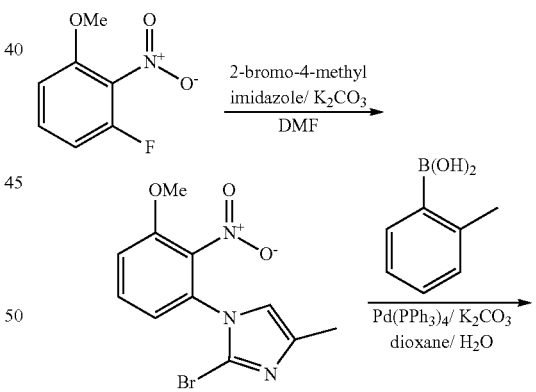

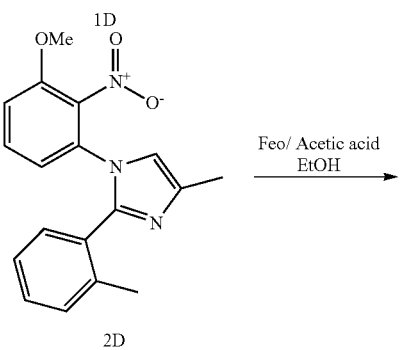

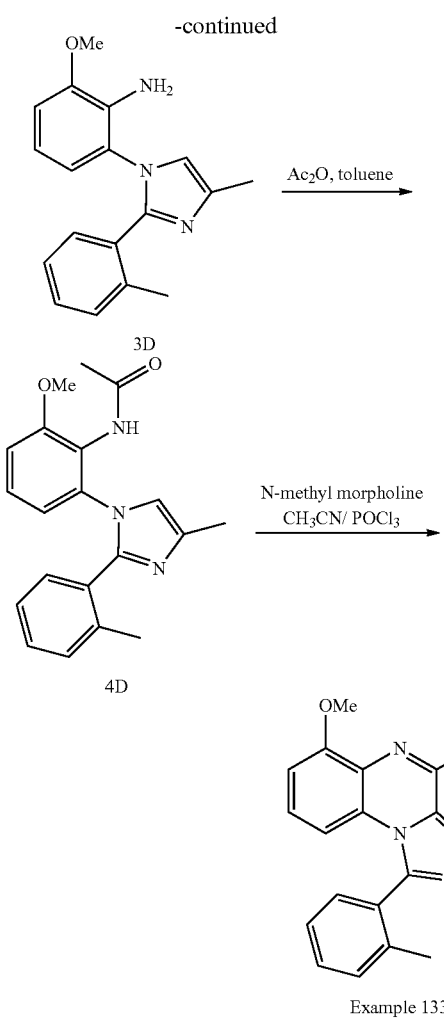

Example 133

Intermediate 1D: 2-Bromo-1-(3-methoxy-2-nitro-phenyl)-4-methyl-1H-imidazole 2-bromo-4-methyl imidazole (3.7 g, 23.4 mmol) and 2-fluoro-6-methoxy-nitrobenzene were dissolved in DMF (80 mL). To this was then added potassium carbonate (6.3 g, 46.8 mmol). The reaction was heated to 90° C. for 16 hrs then poured into water and extracted with ethyl acetate. The organic layer was separated and washed with water then brined, dried over magnesium sulfate and filtered. The solvent was removed under reduced pressure and the crude purified by flash chromatography on silica gel in 20:1 ethyl acetate/methylene chloride. A tan solid (2.6 g) was recovered. MS (ES) m/z 311.9 [M+1]+

Intermediate 2D: 1-(3-Methoxy-2-nitro-phenyl)-4-methyl-2-o-tolyl-1H-imidazole

Intermediate 1D, method D (0.6 g, 1.9 mmol) and O-tolyl phenyl boronic acid (0.56 g, 3.8 mmol) were dissolved in a solution containing 1,4-dioxane (16 mL) and water (4 mL). To this was then added potassium carbonate (0.56 g, 3.8 mmol). Argon was bubbled into the reaction for 3 min and (triphenylphosphine) palladium (0) (0.1 g, 5% mol) added. The reaction was sealed then heated to 115° C. for 16 hrs, poured into water and extracted with ethyl acetate. The organic layer was separated and washed with water then brined, dried over magnesium sulfate and filtered. The solvent was removed under reduced pressure and the crude purified by flash chromatography on silica gel in 10:1 ethyl acetate/methylene chloride. A white solid (0.5 g) was recovered. MS (ES) m/z 324.1 [M+1]+

Example 133

Intermediate 4D, method D (0.15 g, 0.43 mmol) was suspended in a acetonitrile (1.5 mL). To this was then added phosphorous oxychloride (0.1 mL, 1.0 mmol). The reaction was heated to 85° C. for 3 hrs, poured into aqueous sodium hydroxide (1N) and extracted with ethyl acetate. The organic layer was separated and washed with water then brined, dried over magnesium sulfate and filtered. The solvent was removed under reduced pressure and the crude purified by flash chromatography on silica gel in 10:1 ethyl acetate/hexane. A white solid (0.7 g) was recovered. MS (ES) m/z 318.1 [M+1]+

Examples 134-144 were prepared according to Example 19.

Intermediate 5A (1-bromo-8-fluoro-3,4-dimethylimidazo[1,5-a]quinoxaline) of Scheme 1 was coupled with the corresponding boronic acids or boronic acid pinacol esters under palladium catalyzed conditions.

TABLE 15

Examples 134-144

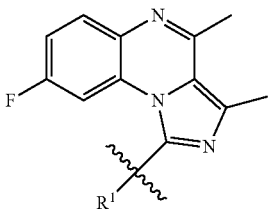

| Example | R¹ | Chemical Name | MS [M + H]+ |
|---|---|---|---|
| 134 | ![R1 structure] | 3-(8-fluoro-3,4-dimethylimidazo[1,5-a]quinoxalin-1-yl)-4-methylbenzamide | 349.1 |
| 135 | ![R1 structure] | 2-fluoro-5-(8-fluoro-3,4-dimethylimidazo[1,5-a]quinoxalin-1-yl)benzamide | 353.1 |

TABLE 15-continued

Examples 134-144

| Example | R¹ | Chemical Name | MS [M + H]⁺ |
|---|---|---|---|
| 136 | 3-fluoro-5-substituted benzamide (with F, C(O)NH₂) | 3-fluoro-5-(8-fluoro-3,4-dimethylimidazo[1,5-a]quinoxalin-1-yl)benzamide | 353.1 |
| 137 | 4-fluoro-3-substituted benzamide (with F, C(O)NH₂) | 4-fluoro-3-(8-fluoro-3,4-dimethylimidazo[1,5-a]quinoxalin-1-yl)benzamide | 353.1 |
| 138 | 2-methylphenyl | 8-fluoro-3,4-dimethyl-1-(2-methylphenyl)imidazo[1,5-a]quinoxaline | 306.1 |
| 139 | 6-fluoro-2-methylpyridin-3-yl | 8-fluoro-1-(6-fluoro-2-methylpyridin-3-yl)-3,4-dimethylimidazo[1,5-a]quinoxaline | 325.1 |
| 140 | 4-methoxypyridin-3-yl | 8-fluoro-1-(4-methoxypyridin-3-yl)-3,4-dimethylimidazo[1,5-a]quinoxaline | 323.1 |
| 141 | 4-methylpyridin-3-yl | 8-fluoro-3,4-dimethyl-1-(4-methylpyridin-3-yl)imidazo[1,5-a]quinoxaline | 307.1 |
| 142 | 3-methylpyridin-4-yl | 8-fluoro-3,4-dimethyl-1-(3-methylpyridin-4-yl)imidazo[1,5-a]quinoxaline | 307.1 |
| 143 | pyridin-4-yl | 8-fluoro-3,4-dimethyl-1-pyridin-4-ylimidazo[1,5-a]quinoxaline | 293.1 |
| 144 | pyridin-3-yl | 8-fluoro-3,4-dimethyl-1-pyridin-3-ylimidazo[1,5-a]quinoxaline | 293.1 |

The symbol " ⌇ " shows the point where substituent R is attached to the tricyclic ring system.

Example A

Inhibition of PDE10

Method A

Phosphodiesterase isoenzyme 10 (PDE10) activity was determined in preparations of rat, pig and guinea pig striatum respectively. Striatum from male Wistar rats (180-200 g), male hybrid pigs (150 kg) and male guinea pigs (CRL (HA), 500 g) respectively were collected and frozen at −70° C.

At the day of preparation 0.5 g striatum was homogenised in 10 ml 50 mM Tris/Mg-buffer at 4° C. and centrifuged for one hour at 100000 g. The supernatant is called the cytosolic fraction and was removed and stored on ice. The pellet was resuspended in the same buffer, but containing 1% Triton and incubated for 45 min at 4° C. Both fractions were independently applied onto a 5 ml Hi Trap™ QHP column at the Äkta-FPLC. After washing the columns the bound PDE protein was eluted with an increasing sodium chloride gradient (0 mM-500 mM sodium chloride) in 50 mM Tris/Mg-buffer at 4° C. for the cytosolic fraction and in the presence of 1% Triton for the membrane fraction. The eluted and collected fractions were tested with 100 nM [³H]-cAMP for PDE10-activity in the presence and without a specific PDE-inhibitor at a concentration, were a 100% inhibition is expected. The fractions with PDE10-activity were pooled and frozen in aliquots until use at −20° C.

PDE10 activity was determined in a one step procedure in microtiter plates. The reaction mixture of 100 µl contained 50 mM Tris-HCl/5 mM MgCl₂ buffer (pH=7.4) (Sigma, Deisenhofen, Germany; Merck, Darmstadt, Germany) 0.1 µM [³H]-cAMP (Amersham, Buckinghamshire, UK) and the enzyme. Nonspecific activity was tested without the enzyme. The reaction was initiated by addition of the substrate solution and was carried out at 37° C. for 30 minutes. Enzymatic activity was stopped by addition of 25 μl YSi-SPA-beads (Amersham-Pharmacia). One hour later the mixture was measured in a liquid scintillation counter for microtiter plates (Microbeta Trilux). To pipette the incubation mixture a robot Biomek (Fa. Beckman) is used. The determined Km-values for the substrate cAMP is 78 nM for PDE10 from rat striatum, 88 nM for pig striatum and 66.7 nM for guinea pig striatum respectively. cGMP is the second substrate for PDE10. The Km values are 1800 nM, 2200 nM and 1700 nM for PDE10 from these species. For the test with cGMP 500 nM of this substrate was used. The optimal amount of enzyme in the assay has been determined and optimised for each enzyme preparation and substrate separately before using the enzyme in compound testing. For determination of $IC_{50}$ values the Hill-plot, 2-parameter-model, was used. Specific inhibitors of other PDE-subtypes do not inhibit the PDE10 preparation significantly. Papaverine was used as the most common PDE10 inhibitor and inhibits the PDE10 with IC50 values of 142 nM, 110 nM and 77 nM for PDE10 from striatum of rat, pig and guinea pig respectively.

Method B

Phosphodiesterase isoenzyme 10 (PDE10) activity was determined in preparations of human recombinant PDE10A and PDE10 from pig striatum respectively.

The DNA of PDE10A1 (AB 020593, 2340 bp) was synthesized and cloned into the vector pCR4.TOPO (Entelechon GmbH, Regensburg, Germany). The gene was than inserted into a baculovirus vector, ligated with the baculovirus DNA. The enzyme-protein was expressed in SF21-cells. The enzyme was isolated from these cells by harvesting the cells by a centrifugation at 200 g to collect the cells. The cells were resuspended in 50 mM Tris-HCl/5 mM $MgCl_2$ buffer (pH=7.4) and lysed by a sonication of the cells. The cytosolic PDE10A was obtained by a centrifugation at 48000 g for 1 h in the supernatant and stored at −70° C.

Striatum from male hybrid pigs (150 kg) were collected and frozen at −70° C. At the day of preparation 0.5 g striatum was homogenised in 10 ml 50 mM Tris/Mg-buffer at 4° C. and centrifuged for one hour at 100000 g. The supernatant was removed and the pellet was resuspended in the same buffer, but containing 1% Triton and incubated for 45 min at 4° C. The membrane fraction was applied onto a 5 ml Hi Trap™ QHP column at the Äkta-FPLC. After washing the column the bound PDE protein was eluted with an increasing sodium chloride gradient (0 mM-500 mM sodium chloride) in 50 mM Tris/Mg-buffer at 4° C. in the presence of 1% Triton. The eluted and collected fractions were tested with 100 nM [3H]-cAMP for PDE10-activity in the presence and without a specific PDE-inhibitor at a concentration, were a 100% inhibition is expected. The fractions with PDE10-activity were pooled and frozen in aliquots until use at −20° C.

PDE10 activity was determined in a one step procedure in microtiterplates. The reaction mixture of 100 μl contained 50 mM Tris-HCl/5 mM MgCl2 buffer (pH=7.4) (Sigma, Deisenhofen, Germany; Merck, Darmstadt, Germany) 0.1 μM [3H]-cAMP (Amersham, Buckinghamshire, UK) and the enzyme. Nonspecific activity was tested without the enzyme. The reaction was initiated by addition of the substrate solution and was carried out at 37° C. for 30 minutes. Enzymatic activity was stopped by addition of 25 μl YSi-SPA-beads (Amersham-Pharmacia). One hour later the mixture was measured in a liquid scintillation counter for microtiterplates (Microbeta Trilux). To pipette the incubation mixture a robot Biomek (Fa. Beckman) is used. The determined Km-values for the substrate cAMP is 88 nM for pig striatum and 130 nM for human recombinant PDE10A respectively. The optimal amount of enzyme in the assay has been determined and optimised for each enzyme preparation before using the enzyme in compound testing. For determination of IC50 values the Hill-plot, 2-parameter-model, was used. Specific inhibitors of other PDE-Subtypes do not inhibit the PDE10 preparation significantly. Papaverine was used as the most common PDE10 inhibitor and inhibits the PDE10 with IC50 values of 89 nM and 103 nM for PDE10 from human recombinant PDE10A and PDE10 from striatum of pig respectively.

The compounds according to this invention are potent inhibitors of the PDE10 with $IC_{50}$ values <1 μM.

The compounds of the invention show significant antipsychotic effects on the MK-801-induced hyperactivity and stereotyped sniffing, an animal model of psychosis.

Test Procedure:

Female Wistar rats (Crl: (WI) BR, Charles River, Sulzfeld, Germany) weighing 150 to 180 g were used for the MK-801-induced psychosis. Animals were housed under standard conditions in groups of five on a 12 h light/dark cycle (light on at 0600 h) with ad libitum access to food (Pellets, ssniff M/R 15, Spezialdiät GmbH, Soest/Westfalen) and water. MK-801 (dizocilpine, MW 337.37) was obtained by Tocris, distributed by Biotrend Chemikalien GmbH, Koöln, Germany.

Preparation of Compounds:

Compounds were freshly suspended in 0.5% hydroxyethylcellulose so that an administration volume of 0.5 ml/100 g was reached for each substance and dose. Hydroxyethylcellulose was solved in distilled water.

MK-801 was dissolved in saline so that an administration volume of 0.5 ml/100 g was reached. The suspensions and solutions were placed on a magnetic stirrer before and during dosing procedures.

The behaviour induced by the NMDA antagonist MK-801 is generally accepted as a rat model of psychosis. MK-801 induces stereotyped sniffing, hyperactivity and ataxia in rats after intraperitoneal administration.

Locomotor activity of the rats was recorded by the MotiTest Apparatus (TSE, Bad Homburg, Germany). The test area consisted of a squared arena (45×45 cm) with protective plexiglass walls (20 cm of height) where rats could freely move. Horizontal movements were recorded by 32 infrared photocells arranged along the bottom of each wall of the arena. The activity [sec] was measured by the computer program "ActiMot" (TSE, Bad Homburg, Germany).

Stereotyped sniffing was scored by the experimenter every five minutes for one hour (12 intervals) according to the method described by Andiné et al. (1999). The scores of the 12 intervals were summed up at the end of the recording time.

| Score | stereotyped sniffing |
|-------|---------------------|
| 0 | no stereotyped sniffing |
| 1 | discontinuous sniffing (free interval >5 s) |
| 2 | continuous sniffing |

The day of experiment the female rats were placed in the laboratory and receive the test compound or vehicle at the appropriate time prior to test. MK-801 0.1 mg/kg was intraperitoneally administered 10 minutes prior to test.

At the beginning of the test the rats were placed in the centre of the squared arena of the MotiTest apparatus. Behaviour of the rats was recorded for one hour. After each run animals were removed and the boxes thoroughly cleaned and dried.

Statistics:

Results were analysed by one way analysis of variance (ANOVA). Tukey test was used for individual comparison. $P \leq 0.05$ was regarded as significant.

Following p.o. or i.p. administration the compounds according to this invention demonstrate in vivo activity in this model at doses $\leq 30$ mg/kg.

Example B

Compound Data

The compounds of the invention are potent inhibitors of PDE10. A substance is considered to effectively inhibit PDE10 if it has an $IC_{50}$ of less than 10 μM, e.g., less than 1 μM. $IC_{50}$ values for select compounds are provided in Table 16 below, where "+" indicates that the $IC_{50}$ value is less than or equal to 10 nM; "++" indicates that the $IC_{50}$ value is between 10-100 nM; and "+++" indicates that the $IC_{50}$ value is equal to or greater than 100 nM.

TABLE 16

PDE 10 inhibition IC50 data for select Examples

| Example | PDE10 pig | PDE10A human |
|---|---|---|
| B1 |  | ++ |
| B2 | ++ |  |
| B3 | ++ |  |
| B4 | ++ |  |
| B5 | ++ |  |
| B6 | ++ |  |
| B7 | ++ |  |
| B8 | + |  |
| B9 | +++ |  |
| B10 | ++ |  |
| B11 |  | ++ |
| B12 |  | ++ |
| B13 |  | +++ |
| B14 | +++ | +++ |
| B15 |  | ++ |
| B16 |  |  |
| 1 | +++ |  |
| 2 | ++ |  |
| 3 | +++ |  |
| 4 | +++ |  |
| 5 | +++ |  |
| 6 | ++ |  |
| 7 |  | ++ |
| 8 | + |  |
| 38 |  | ++ |
| 39 |  | ++ |
| 40 | ++ | +++ |
| 41 | ++ | ++ |
| 9 | ++ |  |
| 10 | ++ |  |
| 11 | +++ |  |
| 12 | +++ |  |
| 13 | ++ |  |
| 14 | ++ |  |
| 15 | + | ++ |
| 16 |  | ++ |
| 17 | ++ |  |
| 18 | ++ |  |
| 19 | ++ |  |
| 20 | ++ |  |
| 21 | ++ |  |
| 22 | ++ |  |
| 23 | ++ |  |
| 24 | + |  |
| 25 | + | ++ |
| 26 | ++ |  |
| 27 | ++ |  |
| 28 | ++ | +++ |
| 29 | ++ | ++ |
| 30 | +++ |  |
| 31 |  | + |
| 32 |  | + |
| 33 |  | + |
| 34 |  |  |
| 35 |  |  |
| 36 |  |  |
| 37 |  |  |
| 42 | ++ | ++ |
| 43 |  | ++ |
| 44 | ++ | +++ |
| 45 | + | + |
| 46 |  | +++ |
| 47 | + | ++ |
| 48 |  | ++ |
| 49 | + | + |
| 50 | + | + |
| 51 | + | + |
| 52 | + | + |
| 53 | + | + |
| 54 | + | ++ |
| 55 | ++ | ++ |
| 56 | + | + |
| 57 | + | ++ |
| 58 | + | + |
| 59 | + | ++ |
| 60 | + | ++ |
| 61 | + | ++ |
| 62 |  | ++ |
| 63 |  | + |
| 64 |  | + |
| 65 |  | ++ |
| 66 |  | ++ |
| 67 |  | + |
| 68 |  | ++ |
| 69 |  | ++ |
| 70 |  | + |
| 71 |  | ++ |
| 72 |  | ++ |
| 73 |  | +++ |
| 74 |  | + |
| 75 |  |  |
| 76 |  | + |
| 77 |  | + |
| 78 |  | + |
| 79 |  | + |
| 80 |  | + |
| 81 |  | + |
| 82 |  | + |
| 83 |  | + |
| 84 |  | + |
| 85 |  | + |
| 86 |  | + (pig) |
| 87 |  | + |
| 88 |  | + |
| 89 |  | ++ |
| 90 |  | +++ |
| 91 |  | ++ |
| 92 |  | + |
| 93 |  | + |
| 94 |  | + |
| 95 |  | + |
| 96 |  |  |
| 97 |  |  |
| 98 |  |  |
| 99 |  | ++ |
| 100 |  | +++ |
| 101 |  | ++ |
| 102 |  | ++ |
| 103 |  | ++ |
| 104 |  | +++ |
| 105 |  | + |

TABLE 16-continued

PDE 10 inhibition IC50 data for select Examples

| Example | PDE10 inhibition IC50 [nM] | |
|---|---|---|
| | PDE10 pig | PDE10A human |
| 106 | | ++ |
| 107 | | + |
| 108 | | ++ |
| 109 | | + |
| 110 | | ++ |
| 111 | | ++ |
| 112 | | + |
| 113 | | ++ |
| 114 | | + |
| 115 | | + |
| 116 | | ++ |
| 117 | | ++ |
| 118 | | + |
| 119 | | + |
| 120 | | + |
| 121 | | ++ |
| 122 | | + |
| 123 | | ++ |
| 124 | | + |
| 125 | | ++ |
| 126 | | + |
| 127 | | + |
| 128 | | ++ |
| 129 | | + |
| 130 | | + |
| 131 | | + |
| 132 | | ++ |
| 133 | | + |
| 134 | | ++ |
| 135 | | ++ |
| 136 | | ++ |
| 137 | | ++ |
| 138 | | ++ |
| 139 | | +++ |
| 140 | | +++ |
| 141 | | +++ |
| 142 | | ++ |
| 143 | | +++ |
| 144 | | +++ |

Various modifications of the invention, in addition to those described herein, will be apparent to those skilled in the art from the foregoing description. Such modifications are also intended to fall within the scope of the appended claims. Each reference, including all patents, patent applications, and journal literature, cited in the present application is incorporated herein by reference in its entirety.

What is claimed is:

1. A compound of formula (IIa)

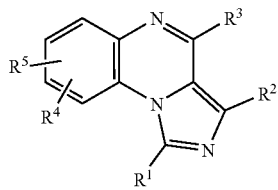

(IIa)

wherein $R^1$ is:
a saturated, monounsaturated or polyunsaturated carbocyclic ring system with 3 to 8 ring atoms or a heterocyclic ring system with 5 to 15 ring atoms containing at least one heteroatom selected from N, N-oxide, O, and S, wherein each ring system is optionally mono- or polysubstituted with halo, amino, $C_{1-3}$ alkylamino, di-$C_{1-3}$ alkylamino, nitro, $C_{1-3}$ alkyl, O—$C_{1-3}$ alkyl, $CF_3$, $OCF_3$, COOH, $CONH_2$, $CONHR^7$, $CON(R^7)_2$, or a cyclic radical;

wherein $R^7$ is in each case independently $C_{1-6}$ alkyl, $C_{2-6}$ alkenyl, $C_{2-6}$ alkynyl, $C_{3-6}$ cycloalkyl, phenyl, or a heterocyclic ring system with 5 to 6 ring atoms containing at least one heteroatom selected from N, N-oxide, O, and S, each optionally mono- or polysubstituted with halo, OH, O—$C_{1-3}$ alkyl, or a cyclic radical, or two $R^7$ in group $CON(R^7)_2$, together with the nitrogen atom to which they are attached, form a saturated or unsaturated five-, six- or seven-membered ring which contains up to 3 heteroatoms selected from N, N-oxide, S, and O, optionally mono- or polysubstituted with halo, $C_{1-3}$ alkyl, O—$C_{1-3}$ alkyl, or aryl-$C_{1-5}$ alkyl, wherein aryl is phenyl, optionally mono- or polysubstituted with halo, nitro, $C_{1-3}$ alkyl, O—$C_{1-3}$ alkyl, or a cyclic radical;

wherein $R^2$ is $C_{1-6}$ alkyl;

$R^3$ is $C_{1-5}$ alkyl;

wherein $R^4$ and $R^5$ are in each case independently selected from:
H,
halo,
a cyclic radical,
$R^9$,
OH or $OR^9$,
NH(C=O)—$C_{1-3}$ alkyl optionally mono- or polysubstituted with halo, OH, O—$C_{1-3}$ alkyl, or a cyclic radical,
$NH_2$, $NHR^9$, and $NR^9R^{10}$; and wherein $R^9$ and $R^{10}$ are independently selected from
a cyclic radical,
$C_{1-6}$ alkyl or $C_{3-6}$ cyclo(hetero)alkyl, optionally mono- or polysubstituted with halo, OH, O—$C_{1-3}$ alkyl, or a cyclic radical,
aryl-$C_{1-5}$ alkyl wherein aryl is phenyl, optionally mono- or polysubstituted with halo, amino, $C_{1-3}$ alkylamino, di-$C_{1-3}$ alkylamino, nitro, $C_{1-3}$ alkyl, OH, O—$C_{1-3}$ alkyl, NH(CO)NHCH$_3$, or a cyclic radical,
or $R^9$ and $R^{10}$, together with the nitrogen atom to which they are attached, form a saturated or unsaturated five-, six- or seven-membered ring which contains up to 3 heteroatoms selected from N, N-oxide, S, and O, optionally mono- or polysubstituted with halo, amino, $C_{1-3}$ alkylamino, di-$C_{1-3}$ alkylamino, $C_{1-3}$ alkyl, O—$C_{1-3}$ alkyl, or aryl-$C_{1-5}$ alkyl, wherein aryl is phenyl, optionally mono- or polysubstituted with halo, amino, $C_{1-3}$ alkylamino, di-$C_{1-3}$ alkylamino, nitro, $C_{1-3}$ alkyl, O—$C_{1-3}$ alkyl, or a cyclic radical;

or a pharmaceutically acceptable salt thereof.

2. The compound of claim 1, or a pharmaceutically acceptable salt thereof, wherein $R^1$ is a saturated, monounsaturated or polyunsaturated carbocyclic ring system with 3 to 8 ring atoms, optionally mono- or polysubstituted with halo, amino, $C_{1-3}$ alkylamino, di-$C_{1-3}$ alkylamino, nitro, $C_{1-3}$ alkyl, O—$C_{1-3}$ alkyl, $CF_3$, $OCF_3$, COOH, $CONH_2$, $CONHR^7$, $CON(R^7)_2$, or a cyclic radical.

3. The compound of claim 2, or a pharmaceutically acceptable salt thereof, wherein $R^1$ is a saturated carbocyclic ring system with 3 to 8 ring atoms.

4. The compound of claim 3, or a pharmaceutically acceptable salt thereof, wherein $R^1$ is cyclohexyl.

5. The compound of claim 2, or a pharmaceutically acceptable salt thereof, wherein $R^1$ is a polyunsaturated carbocyclic ring system with 3 to 8 ring atoms, optionally mono- or polysubstituted with halo, amino, $C_{1-3}$ alkylamino, di-$C_{1-3}$ alkylamino, nitro, $C_{1-3}$ alkyl, O—$C_{1-3}$ alkyl, $CF_3$, $OCF_3$, COOH, $CONH_2$, $CONHR^7$, $CON(R^7)_2$, or a cyclic radical.

6. The compound of claim 5, or a pharmaceutically acceptable salt thereof, wherein $R^1$ is phenyl optionally mono- or polysubstituted with halo, $C_{1-3}$ alkyl, $O$—$C_{1-3}$ alkyl, $CF_3$, $OCF_3$, COOH, $CONH_2$, $CONHR^7$, or $CON(R^7)_2$.

7. The compound of claim 6, or a pharmaceutically acceptable salt thereof, wherein $R^1$ is phenyl optionally mono- or polysubstituted with halo.

8. The compound of claim 7, or a pharmaceutically acceptable salt thereof, wherein $R^1$ is phenyl mono-substituted with chloro.

9. The compound of claim 6, or a pharmaceutically acceptable salt thereof, herein $R^1$ is phenyl optionally mono- or polysubstituted with $C_{1-3}$ alkyl.

10. The compound of claim 9, or a pharmaceutically acceptable salt thereof, wherein $R^1$ is phenyl mono-substituted with methyl.

11. The compound of claim 10, or a pharmaceutically acceptable salt thereof, wherein $R^1$ is 2-methylphenyl.

12. The compound of claim 1, or a pharmaceutically acceptable salt thereof, wherein $R^1$ is a saturated, monounsaturated or polyunsaturated heterocyclic ring system with 5 to 15 ring atoms containing at least one heteroatom selected from N,N-oxide, O, and S, optionally mono- or polysubstituted with halo, amino, $C_{1-3}$ alkylamino, di-$C_{1-3}$ alkylamino, nitro, $C_{1-3}$ alkyl, $O$—$C_{1-3}$ alkyl, $CF_3$, COOH, $CONH_2$, $CONHR^7$, $CON(R^7)_2$, or a cyclic radical.

13. The compound of claim 12, or a pharmaceutically acceptable salt thereof, wherein $R^1$ is a polyunsaturated heterocyclic ring system with 5 to 7 ring atoms containing at least one heteroatom selected from N,N-oxide, O, and S, optionally mono- or polysubstituted with halo, $C_{1-3}$ alkyl, $O$—$C_{1-3}$ alkyl, $CONH_2$, $CONHR^7$, or $CON(R^7)_2$.

14. The compound of claim 13, or a pharmaceutically acceptable salt thereof, wherein $R^1$ is a polyunsaturated heterocyclic ring system with 5 ring atoms containing at least one heteroatom selected from N,N-oxide, O, and S, optionally mono- or polysubstituted with halo, $C_{1-3}$ alkyl, $O$—$C_{1-3}$ alkyl, $CONH_2$, $CONHR^7$, or $CON(R^7)_2$.

15. The compound of claim 14, or a pharmaceutically acceptable salt thereof, wherein $R^1$ is a polyunsaturated heterocyclic ring system with 5 ring atoms containing at least one heteroatom selected from N,N-oxide, O, and S, optionally mono- or polysubstituted with $C_{1-3}$ alkyl.

16. The compound of claim 15, or a pharmaceutically acceptable salt thereof, wherein $R^1$ is thienyl or isoxazolyl optionally mono- or polysubstituted with $C_{1-3}$ alkyl.

17. The compound of claim 15, or a pharmaceutically acceptable salt thereof, wherein $R^1$ is a polyunsaturated heterocyclic ring system with 5 ring atoms containing 1 to 3 nitrogen atoms, optionally mono- or polysubstituted with $C_{1-3}$ alkyl.

18. The compound of claim 17, or a pharmaceutically acceptable salt thereof, wherein $R^1$ is a polyunsaturated heterocyclic ring system with 5 ring atoms containing 1 to 3 nitrogen atoms, optionally mono- or polysubstituted with methyl.

19. The compound of claim 18, or a pharmaceutically acceptable salt thereof, wherein $R^1$ is pyrazolyl, optionally mono- or polysubstituted with methyl.

20. The compound of claim 19, or a pharmaceutically acceptable salt thereof, wherein $R^1$ is pyrazolyl polysubstituted with methyl.

21. The compound of claim 20, or a pharmaceutically acceptable salt thereof, wherein $R^1$ is 1,3,5-trimethyl-1H-pyrazol-4-yl.

22. The compound of claim 13, or a pharmaceutically acceptable salt thereof, wherein $R^1$ is a polyunsaturated heterocyclic ring system with 6 ring atoms containing at least one heteroatom selected from N,N-oxide, O, and S, optionally mono- or polysubstituted with halo, $C_{1-3}$ alkyl, $O$—$C_{1-3}$ alkyl, $CONH_2$, $CONHR^7$, or $CON(R^7)_2$.

23. The compound of claim 22, or a pharmaceutically acceptable salt thereof, wherein $R^1$ is a polyunsaturated heterocyclic ring system with 6 ring atoms containing 1 to 3 nitrogen atoms, optionally mono- or polysubstituted with halo, $C_{1-3}$ alkyl, $O$—$C_{1-3}$ alkyl, $CONH_2$, $CONHR^7$, or $CON(R^7)_2$.

24. The compound of claim 23, or a pharmaceutically acceptable salt thereof, wherein $R^1$ is a polyunsaturated heterocyclic ring system with 6 ring atoms containing 1 to 3 nitrogen atoms, optionally mono- or polysubstituted with $C_{1-3}$ alkyl.

25. The compound of claim 24, or a pharmaceutically acceptable salt thereof, wherein $R^1$ is a polyunsaturated heterocyclic ring system with 6 ring atoms containing 1 to 3 nitrogen atoms, optionally mono- or polysubstituted with methyl.

26. The compound of claim 25, or a pharmaceutically acceptable salt thereof, wherein $R^1$ is pyridinyl, optionally mono- or polysubstituted with methyl.

27. The compound of claim 26, or a pharmaceutically acceptable salt thereof, wherein $R^1$ is pyridinyl mono-substituted with methyl.

28. The compound of claim 27, or a pharmaceutically acceptable salt thereof, wherein $R^1$ is 3-methylpyridin-4-yl.

29. The compound of claim 27, or a pharmaceutically acceptable salt thereof, wherein $R^1$ is 2-methylpyridin-3-yl or 4-methylpyridin-3-yl.

30. The compound of claim 1, or a pharmaceutically acceptable salt thereof, wherein $R^2$ is methyl.

31. The compound of claim 1, or a pharmaceutically acceptable salt thereof, wherein $R^3$ is $C_{1-5}$ alkyl.

32. The compound of claim 31, or a pharmaceutically acceptable salt thereof, wherein $R^3$ is methyl.

33. The compound of claim 1, or a pharmaceutically acceptable salt thereof, wherein $R^4$ and $R^5$ are independently selected from H, halo, a cyclic radical, $C_{1-6}$ alkyl, and $O$—$C_{1-6}$ alkyl, wherein $C_{1-6}$ alkyl and $O$—$C_{1-6}$ alkyl are optionally mono- or polysubstituted with halo, OH, $O$—$C_{1-3}$ alkyl, or a cyclic radical.

34. The compound of claim 33, or a pharmaceutically acceptable salt thereof, wherein $R^4$ and $R^5$ are independently selected from H, halo, a cyclic radical, $C_{1-3}$ alkyl, and $O$—$C_{1-3}$ alkyl, wherein $C_{1-3}$ alkyl and $O$—$C_{1-3}$ alkyl are optionally mono- or polysubstituted with halo or a cyclic radical.

35. The compound of claim 34, or a pharmaceutically acceptable salt thereof, wherein one of $R^4$ and $R^5$ is $O$—$C_{1-3}$ alkyl, and the other of $R^4$ and $R^5$ is H, halo, $C_{1-3}$ alkyl or $O$—$C_{1-3}$ alkyl, wherein $O$—$C_{1-3}$ alkyl are optionally polysubstituted with halo.

36. The compound of claim 35, or a pharmaceutically acceptable salt thereof, wherein one of $R^4$ and $R^5$ is $OCF_3$, and the other of $R^4$ and $R^5$ is H.

37. The compound of claim 34, or a pharmaceutically acceptable salt thereof, wherein one of $R^4$ and $R^5$ is $C_{1-3}$ alkyl, and the other of $R^4$ and $R^5$ is H, halo, $C_{1-3}$ alkyl or $O$—$C_{1-3}$ alkyl, wherein $C_{1-3}$ alkyl and $O$—$C_{1-3}$ alkyl are polysubstituted with halo.

38. The compound of claim 37, or a pharmaceutically acceptable salt thereof, wherein one of $R^4$ and $R^5$ is $CF_3$, and the other of $R^4$ and $R^5$ is H.

39. The compound of claim 34, or a pharmaceutically acceptable salt thereof, wherein one of $R^4$ and $R^5$ is O—$C_{1-3}$ alkyl, and the other of $R^4$ and $R^5$ is halo or O—$C_{1-3}$ alkyl.

40. The compound of claim 39, or a pharmaceutically acceptable salt thereof, wherein one of $R^4$ and $R^5$ is $OCH_3$, and the other of $R^4$ and $R^5$ is fluoro.

41. The compound of claim 39, or a pharmaceutically acceptable salt thereof, wherein both $R^4$ and $R^5$ are $OCH_3$.

42. The compound of claim 1, or a pharmaceutically acceptable salt thereof, wherein the compound has formula (IIb)

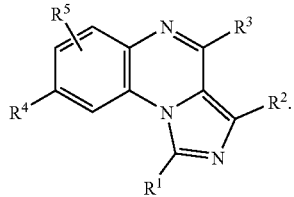

(IIb)

43. The compound of claim 1, or a pharmaceutically acceptable salt thereof, wherein the compound has formula (IIc)

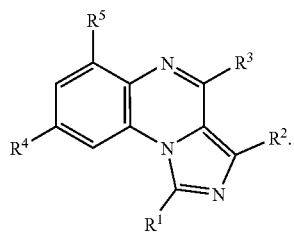

(IIc)

44. The compound of claim 43, or a pharmaceutically acceptable salt thereof, wherein $R^4$ is $OCF_3$ or $CF_3$, and $R^5$ is H.

45. The compound of claim 43, or a pharmaceutically acceptable salt thereof, wherein $R^4$ is $OCH_3$, and $R^5$ is fluoro or $OCH_3$.

46. The compound of claim 43, or a pharmaceutically acceptable salt thereof, wherein $R^4$ is F, and $R^5$ is $OCH_3$.

47. The compound of claim 43, or a pharmaceutically acceptable salt thereof, wherein $R^4$ is F, and $R^5$ is H.

48. The compound of claim 1 selected from:
8-Chloro-1-cyclohexyl-3,4-dimethyl-imidazo(1,5-a)quinoxaline;
1-Cyclohexyl-3,4-dimethyl-8-fluoro-imidazo(1,5-a)quinoxaline;
1-(2-Chlorphenyl)-3,4-dimethyl-8-fluoro-imidazo(1,5-a)quinoxaline;
1-(2,5-Dichlorophenyl)-8-fluoro-3,4-dimethylimidazo[1,5-a]quinoxaline;
1-(3,5-Dichlorophenyl)-8-fluoro-3,4-dimethylimidazo[1,5-a]quinoxaline;
1-(3-Chlorophenyl)-8-fluoro-3,4-dimethylimidazo[1,5-a]quinoxaline;
1-(2,4-Difluorophenyl)-8-fluoro-3,4-dimethylimidazo[1,5-a]quinoxaline;
8-Fluoro-1-(2-methoxyphenyl)-3,4-dimethylimidazo[1,5-a]quinoxaline;
8-Fluoro-1-(3-methoxyphenyl)-3,4-dimethylimidazo[1,5-a]quinoxaline;
8-Fluoro-3,4-dimethyl-1-(2-methylphenyl)imidazo[1,5-a]quinoxaline;
8-Fluoro-3,4-dimethyl-1-(3-methylphenyl)imidazo[1,5-a]quinoxaline;
8-Fluoro-3,4-dimethyl-1-[2-(trifluoromethyl)phenyl]imidazo[1,5-a]quinoxaline;
8-Fluoro-3,4-dimethyl-1-[2-(trifluoromethoxy)phenyl]imidazo[1,5-a]quinoxaline;
8-Fluoro-3,4-dimethyl-1-(3-methyl-2-thienyl)imidazo[1,5-a]quinoxaline;
1-(3,5-Dimethylisoxazol-4-yl)-8-fluoro-3,4-dimethylimidazo[1,5-a]quinoxaline;
6-Fluoro-8-methoxy-3,4-dimethyl-1-(2-methylphenyl)-imidazo[1,5-a]quinoxaline;
6-Fluoro-1-(3-fluoro-2-methylphenyl)-8-methoxy-3,4-dimethylimidazo[1,5-a]quinoxaline;
1-(2-Chloro-4-fluorophenyl)-6-fluoro-8-methoxy-3,4-dimethylimidazo[1,5-a]quinoxaline;
4-Fluoro-3-(6-fluoro-8-methoxy-3,4-dimethylimidazo[1,5-a]quinoxalin-1-yl)benzamide;
1-(2,5-Dichlorophenyl)-3,4-dimethylimidazo[1,5-α]quinoxaline;
3,4-Dimethyl-1-(2-methylphenyl)imidazo[1,5-α]quinoxaline;
1-(4-Methoxypyridin-3-yl)-3,4-dimethylimidazo[1,5-α]quinoxaline;
1-Cyclohexyl-8-methoxy-3,4-dimethyl-imidazo[1,5-a]quinoxaline;
1-Cyclohexyl-8-cyclopropylmethoxy-3,4-dimethyl-imidazo[1,5-a]quinoxaline;
1-(2-Chloro-phenyl)-7-methoxy-3,4-dimethyl-imidazo[1,5-a]quinoxaline;
1-(2-Chloro-phenyl)-6,8-bis-cyclopropylmethoxy-3,4-dimethyl-imidazo[1,5-a]quinoxaline;
1-Cyclohexyl-6,8-dimethoxy-3,4-dimethyl-imidazo[1,5-a]quinoxaline;
6,8-Dimethoxy-3,4-dimethyl-1-o-tolyl-imidazo[1,5-a]quinoxaline;
1-(2-Chloro-phenyl)-6,8-dimethoxy-3,4-dimethyl-imidazo[1,5-a]quinoxaline;
3,4-Dimethyl-1-o-tolyl-imidazo[1,5-a]quinoxaline-6,8-diol;
1-(2-Chloro-phenyl)-3,4-dimethyl-imidazo[1,5-a]quinoxalin-7-ol;
6,8-Bis-difluoromethoxy-3,4-dimethyl-1-o-tolyl-imidazo quinoxaline;
1-(2-Chloro-phenyl)-7-(2,6-difluoro-benzyloxy)-3,4-dimethyl-imidazo[1,5-a]quinoxaline;
1-(2-Chloro-phenyl)-3,4-dimethyl-7-(quinolin-2-ylmethoxy)-imidazo[1,5-a]quinoxaline;
1-(2-Chloro-phenyl)-3,4-dimethyl-7-(3-nitro-benzyloxy)-imidazo[1,5-a]quinoxaline;
3-[1-(2-Chloro-phenyl)-3,4-dimethyl-imidazo[1,5-a]quinoxalin-7-yloxymethyl]-phenylamine; and
1-{3-[1-(2-Chloro-phenyl)-3,4-dimethyl-imidazo[1,5-a]quinoxalin-7-yloxymethyl]-phenyl}-3-methyl-urea;
or a pharmaceutically acceptable salt thereof.

49. The compound of claim 1 selected from:
8-chloro-1-(6-fluoro-2-methylpyridin-3-yl)-3,4-dimethylimidazo[1,5-a]quinoxaline;
8-chloro-3,4-dimethyl-1-(2-methylphenyl)imidazo[1,5-a]quinoxaline;
3-(8-chloro-3,4-dimethylimidazo[1,5-a]quinoxalin-1-yl)benzamide;
8-chloro-3,4-dimethyl-1-(4-methylpyridin-3-yl)imidazo[1,5-a]quinoxaline;
8-chloro-3,4-dimethyl-1-(3-methylpyridin-4-yl)imidazo[1,5-a]quinoxaline;

8-chloro-1-(2-chlorophenyl)-3,4-dimethylimidazo[1,5-a]quinoxaline;
5-(8-chloro-3,4-dimethylimidazo[1,5-a]quinoxalin-1-yl)-2-fluorobenzamide;
8-chloro-3,4-dimethyl-1-(1,3,5-trimethyl-1H-pyrazol-4-yl)imidazo[1,5-a]quinoxaline;
6,8-difluoro-3,4-dimethyl-1-(2-methylphenyl)imidazo[1,5-a]quinoxaline;
6,8-difluoro-3,4-dimethyl-1-(4-methylpyridin-3-yl)imidazo[1,5-a]quinoxaline;
6,8-difluoro-3,4-dimethyl-1-(3-methylpyridin-4-yl)imidazo[1,5-a]quinoxaline;
6-fluoro-8-methoxy-3,4-dimethyl-1-(3-methylpyridin-4-yl)imidazo[1,5-a]quinoxaline;
6-fluoro-8-methoxy-3,4-dimethyl-1-(4-methylpyridin-3-yl)imidazo[1,5-a]quinoxaline;
6-fluoro-8-methoxy-3,4-dimethyl-1-(2-methylpyridin-3-yl)imidazo[1,5-a]quinoxaline;
1-(2-chlorophenyl)-6-fluoro-8-methoxy-3,4-dimethylimidazo[1,5-a]quinoxaline;
2-fluoro-5-(6-fluoro-8-methoxy-3,4-dimethylimidazo[1,5-a]quinoxalin-1-yl)benzamide;
6-fluoro-8-methoxy-3,4-dimethyl-1-(1,3,5-trimethyl-1H-pyrazol-4-yl)imidazo[1,5-a]quinoxaline;
8-fluoro-6-methoxy-1-(4-methoxypyridin-3-yl)-3,4-dimethylimidazo[1,5-a]quinoxaline;
8-fluoro-6-methoxy-3,4-dimethyl-1-(4-methylpyridin-3-yl)imidazo[1,5-a]quinoxaline;
8-fluoro-6-methoxy-3,4-dimethyl-1-(3-methylpyridin-4-yl)imidazo[1,5-a]quinoxaline;
8-fluoro-6-methoxy-3,4-dimethyl-1-(2-methylpyridin-3-yl)imidazo[1,5-a]quinoxaline;
8-fluoro-6-methoxy-3,4-dimethyl-1-(2-methylphenyl)imidazo[1,5-a]quinoxaline;
1-(2-chlorophenyl)-8-fluoro-6-methoxy-3,4-dimethylimidazo[1,5-a]quinoxaline;
2-fluoro-5-(8-fluoro-6-methoxy-3,4-dimethylimidazo[1,5-a]quinoxalin-1-yl)benzamide;
1-(2,4-dimethyl-1,3-thiazol-5-yl)-8-fluoro-6-methoxy-3,4-dimethylimidazo[1,5-a]quinoxaline;
8-fluoro-6-methoxy-3,4-dimethyl-1-(1,3,5-trimethyl-1H-pyrazol-4-yl)imidazo[1,5-a]quinoxaline;
8-fluoro-3,4-dimethyl-1-(2-methylphenyl)imidazo[1,5-a]quinoxalin-6-ol;
6-(cyclopropylmethoxy)-8-fluoro-3,4-dimethyl-1-(2-methylphenyl)imidazo[1,5-a]quinoxaline;
8-fluoro-3,4-dimethyl-1-(2-methylphenyl)-6-(2,2,2-trifluoroethoxy)imidazo[1,5-a]quinoxaline;
6-ethoxy-8-fluoro-3,4-dimethyl-1-(2-methylphenyl)imidazo[1,5-a]quinoxaline;
6-(difluoromethoxy)-8-fluoro-3,4-dimethyl-1-(2-methylphenyl)imidazo[1,5-a]quinoxaline;
6,8-dimethoxy-3,4-dimethyl-1-(4-methylpyridin-3-yl)imidazo[1,5-a]quinoxaline;
6,8-dimethoxy-3,4-dimethyl-1-(3-methylpyridin-4-yl)imidazo[1,5-a]quinoxaline;
6,8-dimethoxy-3,4-dimethyl-1-(2-methylpyridin-3-yl)imidazo[1,5-a]quinoxaline;
4-(6-methoxy-3,4-dimethyl-1-(3-methylpyridin-4-yl)imidazo[1,5-a]quinoxalin-8-yl)morpholine;
4-(6-methoxy-3,4-dimethyl-1-(3-methylpyridin-3-yl)imidazo[1,5-a]quinoxalin-8-yl)morpholine;
3,4-dimethyl-1-(3-methyl-2-thienyl)imidazo[1,5-a]quinoxaline;
1-(3,5-dimethylisoxazol-4-yl)-3,4-dimethylimidazo[1,5-a]quinoxaline;
3-(3,4-dimethylimidazo[1,5-a]quinoxalin-1-yl)benzamide;
3-(3,4-dimethylimidazo[1,5-a]quinoxalin-1-yl)-4-fluorobenzamide;
1-(6-fluoro-2-methylpyridin-3-yl)-3,4-dimethylimidazo[1,5-a]quinoxaline;
3,4-dimethyl-1-(4-methylpyridin-3-yl)imidazo[1,5-a]quinoxaline;
1-(2-chloro-4-fluorophenyl)-8-methoxy-3,4-dimethylimidazo[1,5-a]quinoxaline;
1-[4-chloro-2-(trifluoromethyl)phenyl]-8-methoxy-3,4-dimethylimidazo[1,5-a]quinoxaline;
1-(5-chloro-2-methylphenyl)-8-methoxy-3,4-dimethylimidazo[1,5-a]quinoxaline;
1-(4-fluoro-2-methylphenyl)-8-methoxy-3,4-dimethylimidazo[1,5-a]quinoxaline;
1-(3-fluoro-2-methylphenyl)-8-methoxy-3,4-dimethylimidazo[1,5-a]quinoxaline;
8-methoxy-1-(4-methoxypyridin-3-yl)-3,4-dimethylimidazo[1,5-a]quinoxaline;
8-methoxy-3,4-dimethyl-1-(4-methylpyridin-3-yl)imidazo[1,5-a]quinoxaline;
3-(8-methoxy-3,4-dimethylimidazo[1,5-a]quinoxalin-1-yl)benzamide;
1-(6-fluoro-2-methylpyridin-3-yl)-8-methoxy-3,4-dimethylimidazo[1,5-a]quinoxaline;
4-fluoro-3-(8-methoxy-3,4-dimethylimidazo[1,5-a]quinoxalin-1-yl)benzamide;
8-methoxy-3,4-dimethyl-1-(2-methylphenyl)imidazo[1,5-a]quinoxaline;
3,4-dimethyl-1-(4-methylpyridin-3-yl)-8-(trifluoromethoxy)imidazo[1,5-a]quinoxaline;
1-(6-fluoro-2-methylpyridin-3-yl)-3,4-dimethyl-8-(trifluoromethoxy)imidazo[1,5-a]quinoxaline;
3,4-dimethyl-1-(2-methylphenyl)-8-(trifluoromethoxy)imidazo[1,5-a]quinoxaline;
3,4-dimethyl-1-(3-methylpyridin-4-yl)-8-(trifluoromethoxy)imidazo[1,5-a]quinoxaline;
3-[3,4-dimethyl-8-(trifluoromethoxy)imidazo[1,5-a]quinoxalin-1-yl]benzamide;
3,4-dimethyl-1-(4-methylpyridin-3-yl)-8-(trifluoromethyl)imidazo[1,5-a]quinoxaline;
3,4-dimethyl-1-(3-methylpyridin-4-yl)-8-(trifluoromethyl)imidazo[1,5-a]quinoxaline;
1-(4-methoxypyridin-3-yl)-3,4-dimethyl-8-(trifluoromethyl)imidazo[1,5-a]quinoxaline;
3,4-dimethyl-1-(2-methylpyridin-3-yl)-8-(trifluoromethyl)imidazo[1,5-a]quinoxaline;
3,4-dimethyl-1-(2-methylphenyl)-8-(trifluoromethyl)imidazo[1,5-a]quinoxaline;
8-chloro-7-methoxy-3,4-dimethyl-1-(2-methylphenyl)imidazo[1,5-a]quinoxaline;
8-chloro-7-methoxy-3,4-dimethyl-1-(3-methylpyridin-4-yl)imidazo[1,5-a]quinoxaline;
8-chloro-7-methoxy-3,4-dimethyl-1-(4-methylpyridin-3-yl)imidazo[1,5-a]quinoxaline;
8-chloro-1-(2-chlorophenyl)-7-methoxy-3,4-dimethylimidazo[1,5-a]quinoxaline;
8-chloro-7-methoxy-3,4-dimethyl-1-(2-methylpyridin-3-yl)imidazo[1,5-a]quinoxaline;
8-chloro-7-methoxy-3,4-dimethyl-1-(1,3,5-trimethyl-1H-pyrazol-4-yl)imidazo[1,5-a]quinoxaline;
8-chloro-7-ethoxy-3,4-dimethyl-1-(2-methylphenyl)imidazo[1,5-a]quinoxaline;
6-methoxy-3,4-dimethyl-1-(2-methylphenyl)imidazo[1,5-a]quinoxaline;

3-(8-fluoro-3,4-dimethylimidazo[1,5-a]quinoxalin-1-yl)-4-methylbenzamide;

2-fluoro-5-(8-fluoro-3,4-dimethylimidazo[1,5-a]quinoxalin-1-yl)benzamide;

3-fluoro-5-(8-fluoro-3,4-dimethylimidazo[1,5-a]quinoxalin-1-yl)benzamide;

4-fluoro-3-(8-fluoro-3,4-dimethylimidazo[1,5-a]quinoxalin-1-yl)benzamide;

8-fluoro-3,4-dimethyl-1-(2-methylphenyl)imidazo[1,5-a]quinoxaline;

8-fluoro-1-(6-fluoro-2-methylpyridin-3-yl)-3,4-dimethylimidazo[1,5-a]quinoxaline;

8-fluoro-1-(4-methoxypyridin-3-yl)-3,4-dimethylimidazo[1,5-a]quinoxaline;

8-fluoro-3,4-dimethyl-1-(4-methylpyridin-3-yl)imidazo[1,5-a]quinoxaline;

8-fluoro-3,4-dimethyl-1-(3-methylpyridin-4-yl)imidazo[1,5-a]quinoxaline;

8-fluoro-3,4-dimethyl-1-pyridin-4-ylimidazo[1,5-a]quinoxaline; and 8-fluoro-3,4-dimethyl-1-pyridin-3-ylimidazo[1,5-a]quinoxaline;

or a pharmaceutically acceptable salt thereof.

50. A pharmaceutical composition comprising as an active agent a compound of claim 1, or a pharmaceutically acceptable salt thereof, optionally together with a pharmaceutically acceptable carrier.

* * * * *